(12) United States Patent
Hayes et al.

(10) Patent No.: US 9,187,730 B2
(45) Date of Patent: Nov. 17, 2015

(54) EQUINE RHINITIS VACCINE

(75) Inventors: Phillip Wayne Hayes, Maurice, IA (US); Kristina J. Hennessy, Leawood, KS (US); Laurent Viel, Rockwood (CA); Andres Diaz-Mendez, Dundas (CA)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 330 days.

(21) Appl. No.: 13/417,855

(22) Filed: Mar. 12, 2012

(65) Prior Publication Data

US 2012/0237543 A1    Sep. 20, 2012

Related U.S. Application Data

(60) Provisional application No. 61/510,226, filed on Jul. 21, 2011, provisional application No. 61/452,390, filed on Mar. 14, 2011.

(51) Int. Cl.

| | |
|---|---|
| *A61K 39/125* | (2006.01) |
| *A61K 39/145* | (2006.01) |
| *A61K 39/245* | (2006.01) |
| *C12N 7/00* | (2006.01) |
| *C07K 14/00* | (2006.01) |
| *C07K 14/005* | (2006.01) |
| *C07K 14/08* | (2006.01) |
| *C07K 14/095* | (2006.01) |
| *A61K 35/12* | (2015.01) |
| *A61K 35/66* | (2015.01) |
| *A61K 35/76* | (2015.01) |
| *A61K 39/12* | (2006.01) |
| *A61K 39/00* | (2006.01) |

(52) U.S. Cl.
CPC .............. *C12N 7/00* (2013.01); *A61K 2039/505* (2013.01); *A61K 2039/5254* (2013.01); *C12N 2770/32034* (2013.01); *C12N 2770/32734* (2013.01)

(58) Field of Classification Search
None
See application file for complete search history.

(56) References Cited

U.S. PATENT DOCUMENTS

| | | | |
|---|---|---|---|
| 6,171,592 B1 | 1/2001 | Studdert et al. | |
| 6,235,282 B1 | 5/2001 | Riviere et al. | |
| 6,531,136 B1 | 3/2003 | Studdert et al. | |
| 6,812,219 B2 | 11/2004 | LaColla et al. | |

(Continued)

FOREIGN PATENT DOCUMENTS

| | | |
|---|---|---|
| WO | 9722701 A1 | 6/1997 |
| WO | 0009702 A1 | 2/2000 |

(Continued)

OTHER PUBLICATIONS

Whitehouse, BBC News World Edition article, 2002; 2002Whitehouse_BBCnewsWorldEdition.pdf; downloaded Jan. 14, 2014.*

(Continued)

*Primary Examiner* — Zachariah Lucas
*Assistant Examiner* — Stuart W Snyder
(74) *Attorney, Agent, or Firm* — Michael P. Morris; Joyce L. Morrison

(57) ABSTRACT

The disclosure provides for immunogenic compositions against Equine Rhinitis Virus, particularly Equine Rhinitis A and B Virus, and methods for their use and preparation. The immunogenic compositions, in alternate embodiments, also include other equine pathogens.

45 Claims, 9 Drawing Sheets

(56) References Cited

U.S. PATENT DOCUMENTS

| | | | |
|---|---|---|---|
| 6,878,372 | B2 | 4/2005 | Monath et al. |
| 7,101,861 | B2 | 9/2006 | Sommadossi et al. |
| 7,105,493 | B2 | 9/2006 | Sommadossi et al. |
| 7,148,206 | B2 | 12/2006 | Sommadossi et al. |
| 7,153,513 | B2 | 12/2006 | Chu |
| 7,163,929 | B2 | 1/2007 | Sommadossi et al. |
| 7,227,011 | B2 | 6/2007 | Chang |
| 7,244,430 | B2 | 7/2007 | Throsby et al. |
| 7,384,642 | B2 | 6/2008 | Minke et al. |
| 7,425,336 | B2 | 9/2008 | Minke et al. |
| 7,425,437 | B2 | 9/2008 | UytdeHaag et al. |
| 7,445,787 | B2 | 11/2008 | Chu |
| 7,455,842 | B2 | 11/2008 | Yamshchikov |
| 7,459,163 | B2 | 12/2008 | Yamshchikov |
| 7,468,187 | B2 | 12/2008 | Yoon et al. |
| 7,482,017 | B2 | 1/2009 | Barrett et al. |
| 7,507,415 | B2 | 3/2009 | Arroyo et al. |
| 7,556,812 | B2 | 7/2009 | Tangy et al. |
| 7,585,621 | B2 | 9/2009 | Beall et al. |
| 7,601,502 | B2 | 10/2009 | van de Zande |
| 7,722,884 | B2 | 5/2010 | Shields et al. |
| 7,959,929 | B2 | 6/2011 | Crawford et al. |
| 8,133,712 | B2 | 3/2012 | Sterner et al. |
| 2003/0091595 | A1 | 5/2003 | Chu |
| 2003/0104008 | A1 | 6/2003 | Loosmore et al. |
| 2003/0148261 | A1 | 8/2003 | Fikrig et al. |
| 2008/0279891 | A1 | 11/2008 | Johnston et al. |
| 2009/0130146 | A1 | 5/2009 | Broeker |
| 2010/0285063 | A1 | 11/2010 | Cho et al. |
| 2011/0159033 | A1 | 6/2011 | Hennessy et al. |
| 2012/0237543 | A1 | 9/2012 | Hayes et al. |
| 2014/0328877 | A1 | 11/2014 | Hennessy et al. |

FOREIGN PATENT DOCUMENTS

| | | | |
|---|---|---|---|
| WO | 02067899 | A1 | 9/2002 |
| WO | 02088177 | A1 | 11/2002 |
| WO | 03061555 | A2 | 7/2003 |
| WO | 2007002470 | A2 | 1/2007 |
| WO | 2007051763 | A1 | 5/2007 |
| WO | 2010025469 | A1 | 3/2010 |
| WO | 2012125525 | A2 | 9/2012 |

OTHER PUBLICATIONS

Horsington, et al. Identification of mixed equine rhinitis B virus infections leading to further insight on the relationship between genotype, serotype and acid stability phenotype. Virus Res. 2011; 155: 506-511.*

Minke, et al. Equine viral vaccines: the past, present and future. Vet. Res. 2004; 35:425-443.*

Black, et al. Sequence variation divides Equine rhinitis B virus into three distinct phylogenetic groups that correlate with serotype and acid stability. J. Gen. Virol. 2005; 86: 2323-2332.*

Heldens, et al. Is there a benefit from an early booster vaccination in the control of equine influenza? Vet. J. 2007; 174: 592-598.*

Heldens, et al. Veterinary vaccine development from an industrial perspective. Vet. J. 2008; 178(1): 7-20.*

Offit and Jew, Addressing Parents' Concerns: Do Vaccines Contain Harmful Preservatives, Adjuvants, Additives, or Residuals? Pediatrics, 2003; 112(6): 1394-1397.*

Black et al., "Formerly unclassified, acid-stable equine picornaviruses are a third equine rhinitis B virus serotype in the genus Erbovirus". Journal of General Virology, vol. 87, 2006, pp. 3023-3027.

International Search Report and Written Opinion for PCT/US2012/028706 mailed on Jan. 10, 2013.

Van Hoof, J. "Manufacturing Issues Related to Combining Different Antigens: An Industry Perspective". Clinical Infectious Diseases, Suppl. 4, vol. 33, 2001, p. S346-S350.

"Scientific Discussion". EMEA, 2008, pp. 1-17.

Anderson et al., "Isolation of West Nile Virus from Mosquitoes, Crows and a Cooper's Hawk in Connecticut". Science, vol. 286, Dec. 1999, pp. 2331-2333.

Arroyo et al., "ChimerVax-West Nile Virus Live-Attenuated Vaccine: Preclinical Evaluation of Safety, Immogenicity, and Efficacy". Journal of Virology, vol. 78, No. 22, Nov. 2004, pp. 12497-12507.

Dauphin et al., "West Nile Virus: Recent Trends in Diagnosis and Vaccine Development". Vaccine, vol. 25, 2007, pp. 5563-5576.

Hall et al., "West Nile Virus Vaccines". Expert Opinion on Biological Therapy, vol. 4, No. 8, 2004, pp. 1295-1305.

Lustig et al., "A Live Attenuated West Nile Virus Strain as a Potential Veterinary Vaccine". Viral Immunology, vol. 13, No. 4, 2000, pp. 401-410.

Monath et al., "West Nile Virus Vaccine". Current Drug Targets-Infectious Disorders, vol. 1, No. 1, 2001, pp. 37-50.

Moudy et al., "A Newly Emergent Genotype of West Nile Virus is transmitted Earlier and More Efficiently by Culex Mosquitoes". The American Journal of Tropical Medicine and Hygiene, vol. 77, No. 2, 2007, pp. 365-370.

Bryant et al., "Antigenic and genetic variations in European and North American equine influenza virus strains (H3N8) isolated from 2006 to 2007". Veterinary Microbiology, vol. 138, 2009, pp. 41-52.

Davis et al., "Phylogenetic analysis of North American West Nile virus isolates, 2001-2004: Evidence for the emergence of a dominant genotype". Virology, vol. 342, 2005, pp. 252-265.

Ebel et al., "Genetic and Phenotypic Variation of West Nile Virus in New York, 2000-2003" American Journal of Tropical Medicine and Hygiene, vol. 71, No. 4, 2004, pp. 493-500.

Eckels et al., "Formalin-Inactivated Whole Virus and Recombinant Subunit Flavivirus Vaccines". Advances in Virus Research, vol. 61, 2003, pp. 395-418.

Hilgers et al., "Alkyl-esters of polyacrylic acid as vaccine adjuvants". Vaccine, vol. 16, No. 16, 1998, pp. 1575-1581.

Imam et al., "Challenge of Hamsters With Japanese B, St. Louis and Murray Valley Encephalitis Viruses After Immunization by West Nile Infection Plus Specific Vaccine". The Journal of Immunology, vol. 79, 1957, pp. 243-252.

Konishi et al., "Dengue tetravalet DNA vaccine inducing neutralizing antibody and anamnestic responses to four serotypes in mice". Vaccine, vol. 24, 2006, pp. 2200-2207.

Price et al., "Live and Inactivated Vaccines of Group B Arboviruses: Role of Neutralizing Antibody and Serum Protective Factor". Nature, vol. 222, Jun. 1969, pp. 1294-1295.

Snapinn et al., "Declining Growth Rate of West Nile Virus in North America". Journal of Virology, vol. 81, No. 5, Mar. 2007, pp. 2531-2534.

Steele et al., "Pathology of Fatal West Nile Virus Infections in Native and Exotic Birds during the 1999 Outbreak in New York City, New York". Veterinary Pathology, vol. 37, 2000, pp. 208-224.

"West Nile Innovator + EWT"., Ft. Dodge Material Safety Data Sheet, Fort Dodge Animal Health—A Division of Wyeth Corporation, Jan. 23, 2004, pp. 1-5.

"West Nile Innovator + VEWT"., Fort Dodge Material Safety Data Sheet, Fort Dodge Animal Health, Apr. 10, 2007, pp. 1-6.

Blood-Horse Staff, "Fort Dodge Releases West Nile DNA Vaccine"., BloodHorse.com, Jul. 19, 2005, 1 page. [Accessed at http://www.bloodhorse.com/horse-racing/articles/29112/fort-dodge-releases-west-nile- . . . on Apr. 9, 2013.].

Cohen, Bettina, "The Golden Age of Horse Health". BloodHorse.com, Nov. 22, 2004, 4 pages. [Accessed at: http://www.bloodhorse.com/horse-racing/articles/25516/the-golden-age-of-horse-healt . . . on Apr. 8, 2013.].

Kramer et al., "West Nile virus"., The Lancet Neurology, vol. 6, 2007, pp. 171-181.

Lanciotti et al., "Origin of the West Nile Virus Responsible for the Outbreak of Encephalitis in the Northeastern United States". Science, vol. 286, No. 17, Dec. 1999, pp. 2333-2337. [Accessed at www.sciencemag.org on Dec. 20, 2010].

Minke et al., "Equine viral vaccines: the past, the present and future". Veterinary Research, vol. 35, 2004, pp. 425-443.

Wilson, J.H., "Vaccine Efficacy and Controversies". American Asssociation of Equine Practitioners Annual Proceedings, vol. 51, 2005, pp. 409-420.

(56) References Cited

OTHER PUBLICATIONS

Black et al., "Prevalence of serum neutralising antibody to equine rhinitis A virus (ERAV), equine rhinitis B virus 1 (ERBV1) and ERBV2". Veterinary Microbiology, vol. 119, 2007, pp. 65-71.

Burrows, R., "Equine Rhinoviruses". Proceedings of the 2nd International Conference of Equine Infectious Diseases, Paris, 1969, pp. 154-164.

Burrows, R., Equine Rhinovirus and Adenovirus Infections. Proceedings of the 24th Annual Convention of the American Association of Equine Practicitioners, 1979, pp. 299-306.

Campbell et al., "Immunogenicity of Equine Herpesvirus Type 1 (EHV1) and Equine Rhinovirus Type 1 (ERhV1) following inactivation by Betapropiolactone (BPL) and Ultraviolet (UV) Light". Veterinary Microbiology, vol. 7, No. 6, Dec. 1982, pp. 535-544.

Diaz-Mendez et al., "Surveillance of equine respiratory viruses in Ontario". The Canadian Journal of Veterinary Research, vol. 74, Jan. 2010, pp. 271-278.

Dynon et al., "Detection of viruses in nasal swab samples from horses with acute, febrile, respiratory disease using virus isolation, polymerase chain reaction and serology". Australian Veterinary Journal, vol. 85, Nos. 1 & 2, Jan.-Feb. 2007, pp. 46-50.

Dynon et al., "Identification of equine herpesvirus 3 (equine coital exanthema virus), equine gammaherpesviruses 2 and 5, equine adenoviruses 1 and 2, equine arteritis virus and equine rhinitis A virus by polymerase chain reaction". Australian Veterinary Journal, vol. 79, No. 10, Oct. 2001, pp. 695-702.

Groppelli et al., "Cell Entry of the Aphthovirus Equine Rhinitis A Virus Is Dependent on Endosome Acidification". Journal of Virology, vol. 84, No. 12, Jun. 2010, pp. 6235-6240.

Hartley et al., "Equine rhinitis A virus: structural proteins and immune response". Journal of General Virology, vol. 82, 2001, pp. 1725-1728.

Holmes et al., "Equine Rhinovirus Infection—Serologic Evidence of Infection in Selected United States Horse Populations". Equine Infectious Diseases IV, Proceedings of the 4th International Conference, The Journal of Equine Medicine and Surgery Supplement, 1978, pp. 315-319.

Klaey et al., "Field case study of equine rhinovirus 1 infection: clinical signs and clinicopathology". Equine Veterinary Journal, vol. 30, No. 3, 1998, pp. 267-269.

Kriegshäuser et al., "Prevalence of neutralizing antibodies to Equine rhinitis A and B virus in horses and man". Veterinary Microbiology, vol. 106, Nos. 3-4, Apr. 2005, pp. 293-296.

Li et al., "Identification of noncytopathic equine rhinovirus 1 as a cause of acute febrile respiratory disease in horses". Journal of Clinical Microbiology, vol. 35, No. 4, Apr. 1997, pp. 937-943.

Melgar et al., "A Technique for the Detection of Antibodies Against Equine Rhinovirus Using Complement Mediated Haemolysis in Agarose Gels". Veterinary Microbiology, vol. 5, 1980, pp. 155-159.

Paillot et al., "Equine Herpes Virus-1: Virus, Immunity and Vaccines". The Open Veterinary Science Journal, vol. 2, Jan. 2008, pp. 68-91.

Paillot et al., "Vaccination against equine influenza: Quid novi?". Vaccine, vol. 24, 2006, pp. 4047-4061.

Plummer et al., "Studies on an Equine Respiratory Virus". The Veterinary Record, vol. 74, No. 36, Sep. 8, 1962, pp. 967-970.

Plummer, G. "Virology: An Equine Respiratory Virus with Enterovirus Properties". Nature, vol. 195, No. 4840, Aug. 4, 1962, pp. 519-520.

Powell et al., "Respiratory Viral Infections among Thoroughbred Horses in Training during 1972". Equine Veterinary Journal, vol. 6, No. 1, Jan. 1974, pp. 19-24.

Quinlivan et al., "Real-time RT-PCR for the detection and quantitative analysis of equine rhinitis viruses". Equine Veterinary Journal, vol. 42, No. 2, 2010, pp. 98-104.

Spier et al., "Multivalent Vaccines: Prospects and Challenges*". Folia Microbiologica, vol. 42, No. 2, 1997, pp. 105-112.

Steck et al., "Equine Rhinoviruses: New Serotypes". Equine Infectious Diseases IV, Chapter 36, 1978, pp. 321-328.

Wutz et al., "Equine rhinovirus serotypes 1 and 2: relationship to each other and to aphthoviruses and cardioviruses". Journal of General Virology, vol. 77, 1996, pp. 1719-1730.

Malkinson et al., "Use of Live and Inactivated Vaccines in the Control of West Nile Fever in Domestic Geese". Annals of the New York Academy of Sciences, 2001, pp. 255-261.

Wang et al., "Immunization of Mice Again West Nile Virus with Recombinant Envelope Protein".The Journal of Immunology, vol. 167, 2001, pp. 5273-5277.

\* cited by examiner

Proportion of virus positive across time

Proportion of buffy coat positive across time

SN Titers Across Time

Mean Nasal Scores Across Time

Mean Ocular Scores Across Time

FIG. 6

ClustalW alignment of equine rhinitis A virus (ERAV) isolates showing nucleotide insertions (bold) and deletions (shading) of the 5' UTR.

```
PERV-1      ACTTTTA-GGAGATGACCAAACGCAGTAACCGCAAGCAATTGCCTGTAGCGTCAGTAAAA  111
ERAV/ON/05  ATGCCTGTAGCGTCAGTAAAACGCGGTAAACATAGCGT-TTGACTGTAGCGTCAGTAAAA  119
              *    * **       *     ****** ****  *  *  *** ************

PERV-1      CGCAATA--CACAAGAT-TTGAGCCTGTAGCGTCAGTAAAACGCTGCAACCACAAGCTAT  168
ERAV/ON/05  CGCAACAACCATACGCTGTTGTGCCTGTAGCGTCAGTAAAACGCGGCAAACGCAAGC-AT  178
            ***** *    *   * *   ******************** * *** *  **** **

PERV-1      TGACTGTAGCGTCAGTAAAACGCAA---------------ACATTCTTGTGGCGCTGCGTA  215
ERAV/ON/05  TAACTGTAGCGTCAGTAAAACGCAACAACCATACGCTAATGTGCCTGAGCGTCAGTAAA  238
            * ***********************               *   **  * **  *  *

PERV-1      -GCGCTCA---AGTGCAGAGCTTCCCGGCTTTAAGGGTTACTGCTCGTAATGAGAGCACAT  272
ERAV/ON/05  CGCATACAGCAAACCAGAGCTTCCCGGCTTTAAGGGTTACTGCTCGTAATGAGAGCACTT  298
             ***  **    *  ********************************* * ********

PERV-1      GACATTTGCCAAGATTCCTGGCAATTGTCACGGGAGAGAGGAGCCCGTTCTCGGGCAC  332
ERAV/ON/05  GGCAATTGTCAGGATTCCTGGTGGTTGTCACGGGAGAGAGGAGCCCGTTTTCGGGCAC  358
            *  * **** ** ********   *************************  *******

PERV-1      TTTCTCTCAAACAATGTTGGCGCGCCTCGGCGCGCCCCCCTTTTCAGCCCCCTGTCA  392
ERAV/ON/05  TGTTCCCAACAAACATTTGTGCGCTCGGCGCACCCCGCT   CAGCCCCTGTCA  413
              *    ***  ***   *  ***  ******* ****      ********* **
```

Total clinical score means from control, infected, and re-infected groups

Body temperature means from control, infected, and re-infected groups.

FIG. 9

Titers to equine rhinitis A virus (ERAV) and equine rhinitis B virus (ERBV) in control, infected, and re-infected groups. The virus neutralization test (VN) was used to measure antibody titers on serum samples.

| Control Group | | | | | Infected Group | | | | | Re-infected Group | | | | |
|---|---|---|---|---|---|---|---|---|---|---|---|---|---|---|
| | ERAV | ERBV | AE2 | EHV 1/4 | | ERAV | ERBV | AE2 | EHV 1/4 | | ERAV | ERBV | AE2 | EHV 1/4 |
| Pony #1 | | | | | Pony #5 | | | | | Pony #9 | | | | |
| Day 0 | <1:2 | 1:8 | ND | | Day 0 | <1:2 | 1:12 | ND | | Day 0 | 1:1536 | 1:48 | ND | |
| Day 7 | <1:2 | 1:24 | ND | NT | Day 7 | 1:512 | 1:8 | ND | NT | Day 7 | 1:1024 | 1:96 | ND | NT |
| Day 14 | <1:2 | 1:32 | ND | NT | Day 14 | 1:1536 | 1:8 | ND | NT | Day 14 | 1:1536 | 1:64 | ND | NT |
| Day 21 | <1:2 | 1:8 | ND | | Day 21 | 1:1536 | 1:16 | ND | | Day 21 | 1:1536 | 1:48 | ND | |
| Pony #2 | | | | | Pony #6 | | | | | Pony #10 | | | | |
| Day 0 | <1:2 | 1:24 | ND | | Day 0 | <1:2 | 1:32 | ND | | Day 0 | 1:1024 | 1:64 | ND | |
| Day 7 | <1:2 | 1:32 | ND | NT | Day 7 | 1:256 | 1:24 | ND | NT | Day 7 | 1:12288 | 1:24 | ND | NT |
| Day 14 | <1:2 | 1:32 | ND | NT | Day 14 | 1:2048 | 1:16 | ND | NT | Day 14 | 1:1536 | 1:64 | ND | NT |
| Day 21 | <1:2 | 1:24 | ND | | Day 21 | 1:2048 | 1:12 | ND | | Day 21 | 1:32768 | 1:44 | ND | |
| Pony #3 | | | | | Pony #7 | | | | | Pony #11 | | | | |
| Day 0 | <1:2 | 1:12 | ND | | Day 0 | <1:2 | 1:4 | ND | | Day 0 | 1:1536 | 1:24 | ND | |
| Day 7 | <1:2 | 1:16 | ND | NT | Day 7 | 1:64 | 1:4 | ND | NT | Day 7 | 1:1536 | 1:16 | ND | NT |
| Day 14 | <1:2 | 1:44 | ND | NT | Day 14 | 1:3072 | 1:3 | ND | NT | Day 14 | 1:2048 | 1:24 | ND | NT |
| Day 21 | <1:2 | 1:24 | ND | | Day 21 | 1:1536 | 1:16 | ND | | Day 21 | 1:1536 | 1:24 | ND | |
| Pony #4 | | | | | Pony #8 | | | | | Pony #12 | | | | |
| Day 0 | <1:2 | 1:16 | ND | | Day 0 | <1:2 | 1:12 | ND | | Day 0 | 1:3072 | 1:4 | ND | |
| Day 7 | <1:2 | 1:32 | ND | NT | Day 7 | 1:256 | 1:16 | ND | NT | Day 7 | 1:12288 | 1:16 | ND | NT |
| Day 14 | <1:2 | 1:44 | ND | NT | Day 14 | 1:2048 | 1:16 | ND | NT | Day 14 | 1:2048 | 1:24 | ND | NT |
| Day 21 | <1:2 | 1:24 | ND | | Day 21 | 1:2048 | 1:16 | ND | | Day 21 | 1:4096 | 1:16 | ND | |

ERAV  Equine rhinitis A virus (virus neutralization test)
ERBV  Equine rhinitis B virus (virus neutralization test)
AE2   Equine influenza 2 (H3N8) (haemagglutinin inhibition test)
EHV 1/4  Equine herpesvirus 1 & 4 (virus neutralization test)
ND    Not detectable (single radial haemolysis test)
NT    Not tested

EQUINE RHINITIS VACCINE

SEQUENCE LISTING

The instant application contains a Sequence Listing which has been submitted in ASCII format via EFS-Web and is hereby incorporated by reference in its entirety. Said ASCII copy, created on Jan. 26, 2012, is named 10-0144-SEQ.txt and is 33,714 bytes in size.

BACKGROUND OF THE INVENTION

Equine viral respiratory infections are commonly associated with movement of horses and annually respiratory outbreaks are reported throughout the world. Equine Influenza 2 (AE2-H3N8), Equine Herpesvirus 1 and 4 (EHV1/4), and Equine Rhinitis A and B Viruses (ERAV and ERBV, respectively) are among the most important viruses isolated from the upper respiratory tract during respiratory outbreaks.

In particular, ERAV has been reported in acute febrile respiratory disease in horses (Li et al., J. Clin. Microbiol. 35:937-943; 1997, incorporated by reference). Similarly, a recent study in Ontario found ERBV and ERAV to be highly prevalent in the horse population (Diaz-Mendez et al., The Canadian Journal of Veterinary Research 74:271-278; 2010, incorporated by reference). Clinical signs of ERAV infection are non-specific and difficult to differentiate from other respiratory viral infections, including equine influenza and herpes virus infections. Non-cytopathic strains of this virus have been identified in equine respiratory outbreaks (Li et al., J. Clin. Microbiol. 35:937-943; 1997) making its diagnosis challenging. Moreover, ERAV and ERBV, being single stranded RNA viruses, have the potential for mutation, rendering the ability of the immune system to protect an animal against disease caused by a given ERAV/ERBV strain unclear.

A need exists for methods and medicaments for preventing respiratory diseases or for reducing the incidence or lessening the severity of clinical symptoms associated with such diseases, including those associated with Equine Rhinitis A and B Viruses.

BRIEF SUMMARY OF THE INVENTION

The inventors have determined that immunogenic compositions comprising one or more strains of inactivated or live, attenuated ERAV, which when live and active and unattenuated are virulent (i.e., at least 50%, 60%, 70%, 80%, 90% or even 100% of seronegative horses, when purposely exposed to the virus, present with observable respiratory disease, particularly nasal and/or ocular discharge), can be grown to high titers in culture to yield a vaccine that is able to induce high titers of serum antibodies against ERAV when administered, for example, to an equine, for example resulting in a serum titer of at least 1:112, and preferably, at least 1:200, 1:500, 1:750 or 1:1000. In addition, the strains grow well in culture and are highly efficient to produce, for example, to a titer of at least $10^6$ TCID$_{50}$/mL, more preferably at least $10^7$ TCID$_{50}$/mL, $10^8$ TCID$_{50}$/mL, or even $10^9$ TCID$_{50}$/mL. Similarly, compositions comprising one or more strains of inactivated ERBV, which when live and active and not attenuated are also virulent (as defined above for ERAV), were also found to grow well in culture, to a titer of at least $10^6$ TCID$_{50}$/mL, more preferably $10^7$ TCID$_{50}$/mL, $10^8$ TCID$_{50}$/mL or even $10^9$ TCID$_{50}$/mL, to be highly efficient to produce, and to induce high titers of serum antibodies in animals following immunization, for example, resulting in a serum titer of at least 1:120 and preferably at least 1:200, 1:500, 1:750 or 1:1000. Both the ERAV and ERBV compositions, and combinations thereof, are capable of reducing the duration, severity, and incidence of disease in an animal such as a horse that has been immunized with the compositions and subsequently challenged.

Accordingly, the present invention provides an immunogenic composition comprising one or more strains of inactivated or live, attenuated ERAV or ERBV, wherein the ERAV strain or the ERBV strain, prior to inactivation or attenuation, causes detectable respiratory disease in at least 50% of seronegative horses exposed to the strain, or grows in cell culture to $10^6$ TCID$_{50}$/mL or higher, or, when used as a vaccine in equines at a dose of $10^6$ TCID$_{50}$ or higher results in a serum titer of at least 1:112.

In certain embodiments, the strain, when alive and unattenuated, causes detectable respiratory disease (e.g., detectable ocular and/or nasal discharge) in at least 50%, 60%, 70%, 80%, 90% or even 100% of seronegative horses upon exposure to the strain.

The strain can be grown in cell culture to a titer of at least $10^6$ TCID$_{50}$/mL, more preferably $10^7$ TCID$_{50}$/mL, $10^8$ TCID$_{50}$/mL, or even $10^9$ TCID$_{50}$/mL. Administration of an immunogenic composition containing the strain results in a serum titer of at least 1:120 and preferably at least 1:200, 1:500, 1:750 or 1:1000.

In the immunogenic compositions of the invention, the one or more strains of ERAV or ERBV preferably include ERAV/ON/05 (ATCC Accession No. PTA-11828) and/or ERBV strain 07-103042 (ATCC Accession PTA-11829). In addition, the immunogenic compositions of the invention contain at least an ERAV strain which comprises a genomic sequence whose reverse transcript has greater than 95% identity to SEQ ID NO: 2 or encodes a polyprotein with an amino acid sequence with greater than 95% identity to SEQ ID NO: 3, wherein said ERAV strain, when not inactivated, is active to infect and replicate in host cells. The immunogenic composition of the invention may also include an ERAV strain which comprises a genomic sequence whose reverse transcript has a nucleotide sequence comprising SEQ ID NO: 2 or encodes a polyprotein with an amino acid sequence of SEQ ID NO: 3.

The immunogenic compositions of the invention may also include an ERBV strain which comprises a genomic sequence whose reverse transcript has greater than 95% identity to the reverse transcript of the genomic sequence of the ERBV strain having ATCC Accession no. PTA-11829 or encodes a polyprotein with an amino acid sequence with greater than 95% identity to the polyprotein encoded by the genome of the ERBV strain having ATCC Accession no. PTA-11829, wherein said ERBV strain, when not inactivated, is active to infect and replicate in host cells. The ERBV strain may also comprise a genomic sequence that is the genomic sequence of the ERBV strain having ATCC Accession no. PTA-11829 or encodes a polyprotein that has the amino acid sequence of the polyprotein encoded by the genome of the ERBV strain having ATCC Accession no. PTA-11829.

In a specific embodiment, the immunogenic composition of the invention comprises Equine Rhinitis A Virus (ERAV) and Equine Rhinitis B Virus (ERBV), wherein the ERAV strain is ERAV/ON/05 and the ERBV strain has ATCC Accession No. PTA-11829.

In addition, the invention further includes multivalent immunogenic compositions comprising inactivated or live attenuated viruses or antigens from viruses other than ERAV or ERBV that cause disease in Equidae. In particular, the invention provides immunogenic compositions comprising, in addition to inactivated or live, attenuated ERAV and/or ERBV, at least one antigen or one inactivated or live, attenuated strain of Equine Herpes Virus (EHV), and, in particular embodiments, the EHV is selected from the group consisting of EHV-1 and EHV-4, and a combination thereof, more specifically, the Equine Herpes Virus is selected from the group consisting of EHV-1, EHV-4, strains deposited with the American Type Culture Collection (ATCC), located at 10801 University Boulevard, Manassas, Va. 20110-2209 on Sep. 23, 2008, under the provisions of the Budapest Treaty, under accession Nos. PTA-9525 and PTA-9526, and a combination thereof.

The invention further provides immunogenic composition, which, in addition to the inactivate or live, attenuated strain of ERAV and/or ERBV, at least one inactivated or live, attenuated strain of or at least one antigen of Equine Influenza Virus. In specific embodiments, the Equine Influenza Virus is selected from the group consisting of Clade 1 viruses, Clade 2 viruses, Influenza A/South Africa/2003, Influenza A/equine-2/Ohio/03, Influenza A/equine-2/New Market/2/93, Influenza A/equine-2/Kentucky/95, Influenza A/equine-2/Richmond/1/2007, strains deposited with the American Type Culture Collection (ATCC), located at 10801 University Boulevard, Manassas, Va. 20110-2209, on Sep. 23, 2008, under the provisions of the Budapest Treaty, under accession Nos. PTA-9522, PTA-9523, and PTA-9524, and combinations thereof. The immunogenic compositions may include, in addition to inactivated or live, attenuated ERAV and/or ERBV, at least one antigen or one inactivated or live, attenuated strain of Equine Herpes Virus and at least one antigen or one inactivated or live, attenuated strain of Equine Influenza Virus.

The immunogenic compositions of the invention may include, in addition to inactivated or live, attenuated ERAV and/or ERBV, at least one inactivated or live, attenuated virus or at least one antigen of one or more strains selected from the group consisting of West Nile Virus, Eastern Equine Encephalomyelitis Virus, Western Equine Encephalomyelitis Virus, Venezuelan Equine Encephalomyelitis Virus, and Tetanus Toxoid, and combinations thereof. Alternatively, the immunogenic composition, in addition to inactivated or live, attenuated ERAV and/or ERBV, comprises one or more inactivated or live, attenuated strains of or antigens of strains of Eastern Equine Encephalomyelitis, Western Equine Encephalomyelitis, Venezuelan Equine Encephalomyelitis Virus, and Tetanus Toxoid. In specific embodiments, the West Nile Virus is one of the strains selected from the group consisting of Horse Origin 2005, deposited with the American Type Culture Collection (ATCC), located at 10801 University Boulevard Manassas, Va. 20110-2209, on Sep. 23, 2008, under the provisions of the Budapest Treaty, under accession number PTA-9409; NAEE159, deposited at the United States Department of Agriculture Isolate under accession number 405330; NY2002Nassau; NY2002Clinton; NY2002Queens; GA20021; GA20022; TX20021; TX20022; IN2002; NY2003Albany; NY2003Suffolk; NY2003Chatauqua; CO20031; CO20032; TX2003; TX2003Harris4; TX2003Harris6; TX2003Harris7; TX2003Harris10; AZ2004; and TX2004Harris4; and combination thereof. In immunogenic compositions comprising Western Equine Encephalomyelitis Virus, the strain may be the strain deposited with the American Type Culture Collection (ATCC), located at 10801 University Boulevard Manassas, Va. 20110-2209 on Aug. 14, 2008, under the provisions of the Budapest Treaty, under accession number PTA-9410. In compositions comprising Venezuelan Equine Encephalomyelitis Virus, the strain may be the strain deposited with the American Type Culture Collection (ATCC), located at 10801 University Boulevard, Manassas, Va. 20110-2209, on Aug. 14, 2008, under the provisions of the Budapest Treaty, under accession number PTA-9411. In immunogenic compositions comprising Eastern Equine Encephalomyelitis Virus, the strain may be the strain deposited with the American Type Culture Collection (ATCC), located at 10801 University Boulevard, Manassas, Va. 20110-2209, on Aug. 14, 2008, under the provisions of the Budapest Treaty, under accession number PTA-9412. And, in immunogenic compositions comprising Equine Herpes Virus, the strain may be selected from the group consisting of the strains deposited with the American Type Culture Collection (ATCC), located at 10801 University Boulevard, Manassas, Va. 20110-2209, on Sep. 23, 2008, under the provisions of the Budapest Treaty, under accession Nos. PTA-9525 or PTA-9526, and combinations thereof.

In specific embodiments, one or more of the strains in the immunogenic composition are present in an amount from about $10^{2.0}$ TCID$_{50}$/mL, to about $10^{10.0}$ TCID$_{50}$/mL per dose. The composition may further include a suitable pharmaceutical carrier, such as a diluent, adjuvant, antimicrobial agent, preservative, inactivating agent, or combination thereof. In particular embodiments, the immunogenic composition comprises an adjuvant, specifically, HRA-5.

The invention further provides methods for reducing the incidence or lessening the severity of clinical symptoms associated with or caused by Equine Rhinitis A Virus or Equine Rhinitis B Virus in an animal or a herd of animals comprising the step of administering an immunogenic composition that comprises one or more strains of inactivated or live, attenuated ERAV or ERBV, wherein the ERAV strain or the ERBV strain, prior to inactivation or attenuation, causes detectable respiratory disease in at least 50% of seronegative horses exposed to the strain, or grows in cell culture to $10^6$ TCID$_{50}$/mL or higher, or, when used as a vaccine in equines at a dose of $10^6$ TCID$_{50}$ or higher results in a serum titer of at least 1:112. In particular, the one or more strains of ERAV or ERBV preferably include ERAV/ON/05 (ATCC Accession No. PTA-11828) and/or ERBV strain 07-103042 (ATCC Accession PTA-11829). In addition, the ERAV strain may comprise a genomic sequence whose reverse transcript has greater than 95% identity to SEQ ID NO: 2 or encodes a polyprotein with an amino acid sequence with greater than 95% identity to SEQ ID NO: 3, wherein said ERAV strain, when not inactivated or attenuated, is active to infect and replicate in host cells, or the ERAV strain comprises a genomic sequence whose reverse transcript has a nucleotide sequence comprising SEQ ID NO: 2 or encodes a polyprotein with an amino acid sequence of SEQ ID NO: 3. In addition, or alternatively, the ERBV strain may comprise a genomic sequence whose reverse transcript has greater than 95% identity to the reverse transcript of the genomic sequence of the ERBV strain having ATCC Accession no. PTA-11829 or encodes a polyprotein with an amino acid sequence with greater than 95% identity to the polyprotein encoded by the genome of the ERBV strain having ATCC Accession no. PTA-11829, wherein said ERBV strain, when not inactivated or attenuated, is active to infect and replicate in host cells. The ERBV strain may also comprise a genomic sequence that is the genomic sequence of the ERBV strain having ATCC Accession no. PTA-11829 or encodes a polyprotein that has the amino acid sequence of the polyprotein encoded by the genome of the ERBV strain having ATCC Accession no. PTA-11829.

In addition to providing methods for reducing the incidence or lessening the severity of clinical symptoms associated with or caused by ERAV or ERBV in an animal or a herd of animals, the methods of the invention may further reduce the incidence or lessening the severity of clinical symptoms associated with or caused by one or more of the pathogens selected from the group consisting of West Nile Virus, Eastern Equine Encephalomyelitis Virus, Western Equine Encephalomyelitis Virus, Venezuelan Equine Encephalomyelitis Virus, and *Clostridium tetani* in an animal or a herd of animals by administering an immunogenic composition of the invention. The methods of the invention also include methods of reducing the incidence or lessening the severity of clinical symptoms associated with or caused by ERAV or ERBV in an animal or a herd of animals along with reducing the incidence or lessening the severity of clinical symptoms associated with or caused by one or more of the pathogens selected from the group consisting of: Eastern Equine Encephalomyelitis Virus, Western Equine Encephalomyelitis Virus, Venezuelan Equine Encephalomyelitis Virus, Equine Herpes Virus, and *Clostridium tetani* in an animal or a herd of animals by administering an immunogenic composition of the invention.

The invention also provides methods for reducing the incidence or lessening the severity of clinical symptoms associated with or caused by ERAV and/or ERBV as well as one or more of the pathogens selected from the group consisting of: West Nile Virus, Eastern Equine Encephalomyelitis Virus, Western Equine Encephalomyelitis Virus, Venezuelan Equine Encephalomyelitis Virus, Equine Herpes Virus, Equine Influenza Virus, and *Clostridium tetani* in an animal or a herd of animals, comprising the step of administering an immunogenic composition of the invention.

In connection with the methods of the invention, the incidence of clinical symptoms caused by one or more of said pathogens in a herd of animals is reduced from about 10%-50% as compared to a herd not receiving the immunogenic composition. The methods of the invention, in particular embodiments, provide a duration of immunity of at least 12 months against one or more of the pathogens present in the immunogenic composition. In the methods of the invention, the immunogenic composition is administered to an Equidae, preferably a horse. The dosing scheme may include administration of the immunogenic composition in one or more doses. The doses for the methods of the invention may be formulated in 0.5 mL to 2.5 mL dosage forms. Preferably, the methods of the invention administer immunogenic compositions which are safe for use in foals or horses 4 months of age or older.

The invention also provides methods for producing an immunogenic composition comprising one or more strains of inactivated Equine Rhinitis A Virus (ERAV) or Equine Rhinitis B Virus (ERBV) as follows:
a) infecting a susceptible cell line with ERAV or ERBV;
b) growing the infected cell line in growth media until a cytopathic effect (CPE) is attained;
c) harvesting the media;
d) filtering the media to yield a filtered media; and
e) contacting the filtered media with an inactivating agent to obtain the inactivated ERAV or ERBV.

BRIEF DESCRIPTION OF THE DRAWINGS

FIG. 6 is a ClustalW alignment of a portion of equine rhinitis A virus ERAV/ON/05 (5' UTR portion, SEQ ID NO: 1) with ERAV/PERV-1 (accession number: DQ272578 (SEQ ID NO: 14)). ERAV/ON/05 nucleotide insertions shown in bold and deletions in shading.

FIG. 9 is a Table showing titers to equine rhinitis A virus (ERAV) and equine rhinitis B virus (ERBV) in control, infected, and re-infected groups of Example 4. The virus neutralization test (VN) was used to measure antibody titers on serum samples.

DETAILED DESCRIPTION OF THE INVENTION

Figure 1:
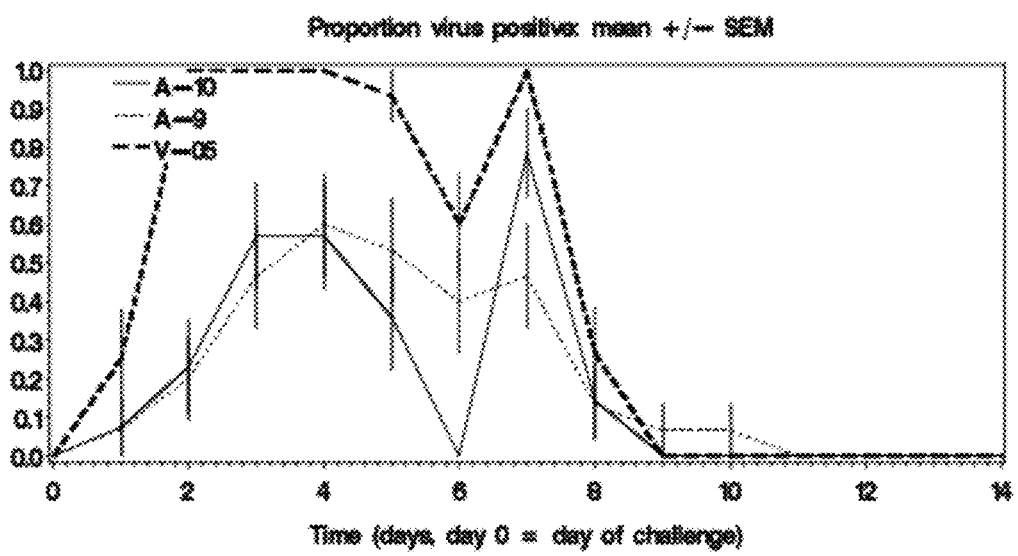
FIG. 1 is a graphical representation of the proportion of virus positive across time.

The inventors have determined that immunogenic compositions comprising one or more strains of inactivated ERAV, which when live and active are virulent (i.e., at least 50%, 60%, 70%, 80%, 90% or even 100% of seronegative horses, when purposely exposed to the virus, present with observable respiratory disease, particularly nasal and/or ocular discharge), can be grown to high titers in culture to yield a vaccine that is able to induce high titers of serum antibodies against ERAV when administered, for example, to an equine, for example resulting in a serum titer of at least 1:112, and preferably, at least 1:200, 1:500, 1:750 or 1:1000. In addition, the strains grow well in culture and are highly efficient to produce, for example, to a titer of at least $10^6$ $TCID_{50}/mL$, more preferably $10^7$ $TCID_{50}/mL$, $10^8$ $TCID_{50}/mL$, or even $10^9$ $TCID_{50}/mL$. Similarly, compositions comprising one or more strains of inactivated ERBV, which when live and active and not attenuated are also virulent (as defined above for ERAV), were also found to grow well in culture, to a titer of at least $10^6$ $TCID_{50}/mL$, more preferably $10^7$ $TCID_{50}/mL$, $10^8$ $TCID_{50}/mL$ or even $10^9$ $TCID_{50}/mL$, to be highly efficient to produce, and to induce high titers of serum antibodies in animals following immunization, for example, resulting in a serum titer of at least 1:120 and preferably at least 1:200, 1:500, 1:750 or 1:1000. Both the ERAV and ERBV compositions, and combinations thereof, are capable of reducing the duration, severity, and incidence of disease in an animal such as a horse that has been immunized with the compositions and subsequently challenged.

In one embodiment, provided is an immunogenic composition comprising one or more strains of inactivated ERAV and/or ERBV. Alternatively, the strains may be attenuated by routine means and the live, attenuated virus used in the vaccine composition. In some embodiments, the ERAV strain comprises a genomic sequence whose reverse transcript has a 5'UTR comprising the nucleotide sequence of SEQ ID NO: 1. In some embodiments, the ERAV strain comprises a genomic sequence whose reverse transcript has a nucleotide sequence with greater than 95%, greater than 96%, greater than 97%, greater than 98% or greater than 99% identity to the nucleotide sequence of SEQ ID NO: 2 and, when not inactivated or attenuated, is active to infect and replicate in host cells and/or encodes functional ERAV proteins, or which encodes a polyprotein having an amino acid sequence with greater than 95%, greater than 96%, greater than 97%, greater than 98% or greater than 99% identity to the amino acid sequence of SEQ ID NO: 3, which polyprotein contains functional ERAV proteins (i.e., active in viral infection and replication). In some embodiments, the ERAV strain comprises a genomic sequence which, when reverse transcribed, has a nucleotide sequence of SEQ ID NO: 2 or which encodes a polyprotein with an amino acid sequence of SEQ ID NO: 3. In certain embodiments the ERAV strain is ERAV/ON/05 having ATCC Accession No. PTA-11828, deposited with the American Type Culture Collection, located at 10801 University Boulevard, Manassas, Va., 20110-2209 on Apr. 14, 2011, under the provisions of the Budapest Treaty, which is hereby incorporated by reference.

In some embodiments, the ERBV is strain 07-103042, having ATCC Accession No. PTA-11829, deposited with the American Type Culture Collection, located at 10801 University Boulevard, Manassas, Va., 20110-2209 on Apr. 14, 2011, under the provisions of the Budapest Treaty, which is hereby incorporated by reference. In some embodiments, the ERBV strain comprises a genomic sequence whose reverse transcript has a nucleotide sequence with greater than 95%, greater than 96%, greater than 97%, greater than 98% or greater than 99% identity to the nucleotide sequence of the reverse transcript of the genome of the ERBV strain having ATCC Accession No. PTA-11829 and, when not inactivated or attenuated, is active to infect and replicate in host cells and/or encodes functional ERBV proteins, or which encodes a polyprotein having an amino acid sequence with greater than 95%, greater than 96%, greater than 97%, greater than 98% or greater than 99% identity to the amino acid sequence of the polyprotein of the strain with ATCC Accession No. PTA-11829, which polyprotein contains functional ERBV proteins (i.e., active in viral infection and replication).

In one embodiment provided is an immunogenic composition comprising inactivated (or, alternatively, live, attenuated) ERAV and ERBV. In some embodiments, the ERAV strain comprises a genomic sequence whose reverse transcript has a 5'UTR comprising the nucleotide sequence of SEQ ID NO: 1. In some embodiments, the ERAV strain comprises a genomic sequence whose reverse transcript has a nucleotide sequence with greater than 95%, greater than 96%, greater than 97%, greater than 98% or greater than 99% identity to the nucleotide sequence of SEQ ID NO: 2 and, when not inactivated, is active to infect and replicate in host cells and/or encodes functional ERAV proteins, or which encodes a polyprotein having an amino acid sequence with greater than 95%, greater than 96%, greater than 97%, greater than 98% or greater than 99% identity to the amino acid sequence of SEQ ID NO: 3, which polyprotein contains functional ERAV proteins (i.e., active in viral infection and replication). In some embodiments, the ERAV strain comprises a genomic sequence which, when reverse transcribed, has a nucleotide sequence of SEQ ID NO: 2 or which encodes a polyprotein with an amino acid sequence of SEQ ID NO: 3. In some embodiments, the ERAV strain is ERAV/ON/05 (ATCC Accession No. PTA-11828). In some embodiments, the ERBV is a strain having ATCC Accession No: PTA-11829. In some embodiments, the ERBV strain comprises a genomic sequence whose reverse transcript has a nucleotide sequence with greater than 95%, greater than 96%, greater than 97%, greater than 98% or greater than 99% identity to the nucleotide sequence of the reverse transcript of the genome of the ERBV strain having ATCC Accession No. PTA-11829 and, when not inactivated, is active to infect and replicate in host cells and/or encodes functional ERBV proteins, or which encodes a polyprotein having an amino acid sequence with greater than 95%, greater than 96%, greater than 97%, greater than 98% or greater than 99% identity to the amino acid sequence of the polyprotein of the strain with ATCC Accession No. PTA-11829, which polyprotein contains functional ERBV proteins (i.e., active in viral infection and replication).

In one embodiment, along with the inactivated or live, attenuated one or more strains of ERAV and/or ERBV, the immunogenic compositions provided herein further comprise at least one antigen or one additional inactivated or live, attenuated strain of Equine Herpes Virus (EHV). In some embodiments the compositions comprise at least one antigen of EHV. In some embodiments the EHV is selected from the group consisting of EHV-1, EHV-4, strains deposited with the ATCC under accession Nos. PTA-9525 and PTA-9526, and combinations thereof. In some embodiments, the ERAV strain comprises a genomic sequence whose reverse transcript has a 5'UTR comprising the nucleotide sequence of SEQ ID NO: 1. In some embodiments, the ERAV strain comprises a genomic sequence whose reverse transcript has a nucleotide sequence with greater than 95%, greater than 96%, greater than 97%, greater than 98% or greater than 99% identity to the nucleotide sequence of SEQ ID NO: 2 and, when not inactivated, is active to infect and replicate in host cells and/or encodes functional ERAV proteins, or which encodes a polyprotein having an amino acid sequence with greater than 95%, greater than 96%, greater than 97%, greater than 98% or greater than 99% identity to the amino acid sequence of SEQ ID NO: 3, which polyprotein contains functional ERAV proteins (i.e., active in viral infection and replication). In some embodiments, the ERAV strain comprises a genomic sequence which, when reverse transcribed, has a nucleotide sequence of SEQ ID NO: 2 or which encodes a polyprotein with an amino acid sequence of SEQ ID NO: 3. In some embodiments, the ERAV strain is ERAV/ON/05 (ATCC Accession No. PTA-11828). In some embodiments, the ERBV is a strain having ATCC Accession No: PTA-11829. In some embodiments, the ERBV strain comprises a genomic sequence whose reverse transcript has a nucleotide sequence with greater than 95%, greater than 96%, greater than 97%, greater than 98% or greater than 99% identity to the nucleotide sequence of the reverse transcript of the genome of the ERBV strain having ATCC Accession No. PTA-11829 and, when not inactivated or attenuated, is active to infect and replicate in host cells and/or encodes functional ERBV proteins, or which encodes a polyprotein having an amino acid sequence with greater than 95%, greater than 96%, greater than 97%, greater than 98% or greater than 99% identity to the amino acid sequence of the polyprotein of the strain with ATCC Accession No. PTA-11829, which polyprotein contains functional ERBV proteins (i.e., active in viral infection and replication).

In one embodiment, along with the inactivated (or attenuated) one or more strains of ERAV and/or ERBV, the immunogenic compositions provided herein further comprise at least one antigen or one additional inactivated or attenuated strain of Equine Influenza Virus (EIV). In some embodiments the compositions comprise at least one antigen of EIV. In some embodiments the EIV is selected from the group consisting of Clade 1 viruses, Clade 2 viruses, Influenza A/South Africa/2003, Influenza A/equine-2/Ohio/03, Influenza A/equine-2/New Market/2/93, Influenza A/equine-2/Kentucky/95, Influenza A/equine-2/Richmond/1/2007 and combinations thereof. In some embodiments, the ERAV strain comprises a genomic sequence whose reverse transcript has a 5'UTR comprising the nucleotide sequence of SEQ ID NO: 1. In some embodiments, the ERAV strain comprises a genomic sequence whose reverse transcript has a nucleotide sequence with greater than 95%, greater than 96%, greater than 97%, greater than 98% or greater than 99% identity to the nucleotide sequence of SEQ ID NO: 2 and, when not inactivated or attenuated, is active to infect and replicate in host cells and/or encodes functional ERAV proteins, or which encodes a polyprotein having an amino acid sequence with greater than 95%, greater than 96%, greater than 97%, greater than 98% or greater than 99% identity to the amino acid sequence of SEQ ID NO: 3, which polyprotein contains functional ERAV proteins (i.e., active in viral infection and replication). In some embodiments, the ERAV strain comprises a genomic sequence which, when reverse transcribed, has a nucleotide sequence of SEQ ID NO: 2 or which encodes a polyprotein with an amino acid sequence of SEQ ID NO: 3. In some embodiments, the ERAV strain is ERAV/ON/05 (ATCC Accession No. PTA-11828). In some embodiments, the ERBV is a strain having ATCC Accession No: PTA-11829. In some embodiments, the ERBV strain comprises a genomic sequence whose reverse transcript has a nucleotide sequence with greater than 95%, greater than 96%, greater than 97%, greater than 98% or greater than 99% identity to the nucleotide sequence of the reverse transcript of the genome of the ERBV strain having ATCC Accession No. PTA-11829 and, when not inactivated or attenuated, is active to infect and replicate in host cells and/or encodes functional ERBV proteins, or which encodes a polyprotein having an amino acid sequence with greater than 95%, greater than 96%, greater than 97%, greater than 98% or greater than 99% identity to the amino acid sequence of the polyprotein of the strain with ATCC Accession No. PTA-11829, which polyprotein contains functional ERBV proteins (i.e., active in viral infection and replication In one embodiment, along with the inactivated (or live, attenuated) one or more strains of ERAV and/or ERBV, the immunogenic compositions provided herein further comprise at least one antigen or one additional inactivated or live, attenuated strain of Equine Influenza Virus and at least one antigen or one additional inactivated or live, attenuated strain of Equine Herpes Virus. In some embodiments the compositions comprise at least one antigen of EHV and at least one antigen of EIV. In some embodiments the EHV is EHV-1 or EHV-4 or a combination thereof and the EIV is selected from the group consisting of Clade 1 viruses, Clade 2 viruses, Influenza A/South Africa/2003, Influenza A/equine-2/Ohio/03, Influenza A/equine-2/New Market/2/93, Influenza A/equine-2/Kentucky/95, Influenza A/equine-2/Richmond/1/2007 and combinations thereof. In some embodiments, the ERAV strain comprises a genomic sequence whose reverse transcript has a 5'UTR comprising the nucleotide sequence of SEQ ID NO: 1. In some embodiments, the ERAV strain comprises a genomic sequence whose reverse transcript has a nucleotide sequence with greater than 95%, greater than 96%, greater than 97%, greater than 98% or greater than 99% identity to the nucleotide sequence of SEQ ID NO: 2 and, when not inactivated or attenuated, is active to infect and replicate in host cells and/or encodes functional ERAV proteins, or which encodes a polyprotein having an amino acid sequence with greater than 95%, greater than 96%, greater than 97%, greater than 98% or greater than 99% identity to the amino acid sequence of SEQ ID NO: 3, which polyprotein contains functional ERAV proteins (i.e., active in viral infection and replication). In some embodiments, the ERAV strain comprises a genomic sequence which, when reverse transcribed, has a nucleotide sequence of SEQ ID NO: 2 or which encodes a polyprotein with an amino acid sequence of SEQ ID NO: 3. In some embodiments, the ERAV strain is ERAV/ON/05 (ATCC Accession No. PTA-11828). In some embodiments, the ERBV is a strain having ATCC Accession No: PTA-11829. In some embodiments, the ERBV strain comprises a genomic sequence whose reverse transcript has a nucleotide sequence with greater than 95%, greater than 96%, greater than 97%, greater than 98% or greater than 99% identity to the nucleotide sequence of the reverse transcript of the genome of the ERBV strain having ATCC Accession No. PTA-11829 and, when not inactivated, is active to infect and replicate in host cells and/or encodes functional ERBV proteins, or which encodes a polyprotein having an amino acid sequence with greater than 95%, greater than 96%, greater than 97%, greater than 98% or greater than 99% identity to the amino acid sequence of the polyprotein of the strain with ATCC Accession No. PTA-11829, which polyprotein contains functional ERBV proteins (i.e., active in viral infection and replication).

In one embodiment, along with the inactivated (or live, attenuated) one or more strains of ERAV and/or ERBV, the immunogenic compositions provided herein further comprise at least one antigen or inactivated virus of one or more additional strains selected from the group consisting of Equine Influenza Virus, Equine Herpes Virus, West Nile Virus, Eastern Equine Encephalomyelitis Virus, Western Equine Encephalomyelitis Virus, and Venezuelan Equine Encephalomyelitis Virus, and/or Tetanus Toxoid, and combinations thereof. In some embodiments, the ERAV strain comprises a genomic sequence whose reverse transcript has a 5'UTR comprising the nucleotide sequence of SEQ ID NO: 1. In some embodiments, the ERAV strain comprises a genomic sequence whose reverse transcript has a nucleotide sequence with greater than 95%, greater than 96%, greater than 97%, greater than 98% or greater than 99% identity to the nucleotide sequence of SEQ ID NO: 2 and, when not inactivated is attenuated, is active to infect and replicate in host cells and/or encodes functional ERAV proteins, or which encodes a polyprotein having an amino acid sequence with greater than 95%, greater than 96%, greater than 97%, greater than 98% or greater than 99% identity to the amino acid sequence of SEQ ID NO: 3, which polyprotein contains functional ERAV proteins (i.e., active in viral infection and replication). In some embodiments, the ERAV strain comprises a genomic sequence which, when reverse transcribed, has a nucleotide sequence of SEQ ID NO: 2 or which encodes a polyprotein with an amino acid sequence of SEQ ID NO: 3. In some embodiments, the ERAV strain is ERAV/ON/05 (ATCC Accession No. PTA-11828). In some embodiments, the ERBV is a strain having ATCC Accession No: PTA-11829. In some embodiments, the ERBV strain comprises a genomic sequence whose reverse transcript has a nucleotide sequence with greater than 95%, greater than 96%, greater than 97%, greater than 98% or greater than 99% identity to the nucleotide sequence of the reverse transcript of the genome of the ERBV strain having ATCC Accession No. PTA-11829 and, when not inactivated or attenuated, is active to infect and replicate in host cells and/or encodes functional ERBV proteins, or which encodes a polyprotein having an amino acid sequence with greater than 95%, greater than 96%, greater than 97%, greater than 98% or greater than 99% identity to the amino acid sequence of the polyprotein of the strain with ATCC Accession No. PTA-11829, which polyprotein contains functional ERBV proteins (i.e., active in viral infection and replication).

In one embodiment, along with the inactivated (or live, attenuated) one or more strains of ERAV and/or ERBV, the immunogenic compositions provided herein further comprise at least one additional inactivated or live, attenuated virus of a strain selected from the group consisting of West Nile Virus, Eastern Equine Encephalomyelitis Virus, Western Equine Encephalomyelitis Virus, and Venezuelan Equine Encephalomyelitis Virus, and/or Tetanus Toxoid, and combinations thereof. In some embodiments, the ERAV strain comprises a genomic sequence whose reverse transcript has a 5'UTR comprising the nucleotide sequence of SEQ ID NO: 1. In some embodiments, the ERAV strain comprises a genomic sequence whose reverse transcript has a nucleotide sequence with greater than 95%, greater than 96%, greater than 97%, greater than 98% or greater than 99% identity to the nucleotide sequence of SEQ ID NO: 2 and, when not inactivated or attenuated, is active to infect and replicate in host cells and/or encodes functional ERAV proteins, or which encodes a polyprotein having an amino acid sequence with greater than 95%, greater than 96%, greater than 97%, greater than 98% or greater than 99% identity to the amino acid sequence of SEQ ID NO: 3, which polyprotein contains functional ERAV proteins (i.e., active in viral infection and replication). In some embodiments, the ERAV strain comprises a genomic sequence which, when reverse transcribed, has a nucleotide sequence of SEQ ID NO: 2 or which encodes a polyprotein with an amino acid sequence of SEQ ID NO: 3. In some embodiments, the ERAV strain is ERAV/ON/05 (ATCC Accession No. PTA-11828). In some embodiments, the ERBV is a strain having ATCC Accession No: PTA-11829. In some embodiments, the ERBV strain comprises a genomic sequence whose reverse transcript has a nucleotide sequence with greater than 95%, greater than 96%, greater than 97%, greater than 98% or greater than 99% identity to the nucleotide sequence of the reverse transcript of the genome of the ERBV strain having ATCC Accession No. PTA-11829 and, when not inactivated or attenuated, is active to infect and replicate in host cells and/or encodes functional ERBV proteins, or which encodes a polyprotein having an amino acid sequence with greater than 95%, greater than 96%, greater than 97%, greater than 98% or greater than 99% identity to the amino acid sequence of the polyprotein of the strain with ATCC Accession No. PTA-11829, which polyprotein contains functional ERBV proteins (i.e., active in viral infection and replication).

In one embodiment, provided is a method of making the immunogenic composition of the present invention. The method generally comprises the steps of combining an inactivated or live, attenuated ERAV and/or ERBV and a pharmaceutically acceptable carrier. In some embodiments, the ERAV strain comprises a genomic sequence whose reverse transcript has a 5'UTR comprising the nucleotide sequence of SEQ ID NO: 1. In some embodiments, the ERAV strain comprises a genomic sequence whose reverse transcript has a nucleotide sequence with greater than 95%, greater than 96%, greater than 97%, greater than 98% or greater than 99% identity to the nucleotide sequence of SEQ ID NO: 2 and, when not inactivated or attenuated, is active to infect and replicate in host cells and/or encodes functional ERAV proteins, or which encodes a polyprotein having an amino acid sequence with greater than 95%, greater than 96%, greater than 97%, greater than 98% or greater than 99% identity to the amino acid sequence of SEQ ID NO: 3, which polyprotein contains functional ERAV proteins (i.e., active in viral infection and replication). In some embodiments, the ERAV strain comprises a genomic sequence which, when reverse transcribed, has a nucleotide sequence of SEQ ID NO: 2 or which encodes a polyprotein with an amino acid sequence of SEQ ID NO: 3. In some embodiments, the ERAV strain is ERAV/ON/05 (ATCC Accession No. PTA-11828). In some embodiments, the ERBV is a strain having ATCC Accession No: PTA-11829. In some embodiments, the ERBV strain comprises a genomic sequence whose reverse transcript has a nucleotide sequence with greater than 95%, greater than 96%, greater than 97%, greater than 98% or greater than 99% identity to the nucleotide sequence of the reverse transcript of the genome of the ERBV strain having ATCC Accession No. PTA-11829 and, when not inactivated or attenuated, is active to infect and replicate in host cells and/or encodes functional ERBV proteins, or which encodes a polyprotein having an amino acid sequence with greater than 95%, greater than 96%, greater than 97%, greater than 98% or greater than 99% identity to the amino acid sequence of the polyprotein of the strain with ATCC Accession No. PTA-11829, which polyprotein contains functional ERBV proteins (i.e., active in viral infection and replication). In some embodiments the method further comprises the step of adding one or more additional equine virus antigens or inactivated or live, attenuated equine viruses. In another embodiment, the method further comprises the step of adding a suitable adjuvant to the composition.

In one embodiment, provided is a method for reducing the incidence of or lessening the severity of clinical symptoms associated with or caused by ERAV or ERBV in an animal or a herd of animals comprising administering an immunogenic composition as disclosed herein to an animal in need thereof. In some embodiments, the animal is a horse.

The aforementioned embodiments may further contain one or more of the following features described below.

In one embodiment, provided is a composition comprising at least one strain of inactivated (or, alternatively, live, attenuated) ERAV and/or ERBV and further containing many or all relevant antigenic components and proteins of pathogenic West Nile Virus (WNV) or an inactivated or live, attenuated strain of WNV.

In one embodiment, provided is a vaccine composition comprising one or more strains of inactivated (or live, attenuated) ERAV and/or ERBV in combination with one or more immunologically effective amounts of antigenic components or one or more inactivated or live, attenuated strains selected from the group consisting of West Nile Virus (WNV), Venezuelan Equine Encephalomyelitis (VEE), Eastern Equine Encephalomyelitis (EEE), Western Equine Encephalomyelitis (WEE), Tetanus toxoid (T), Equine herpes viruses (EHV) including types 1 and 4, Equine influenza viruses (EIV), and combinations thereof, along with a pharmaceutically acceptable carrier. Preferably such embodiments will include an adjuvant, such as a carbomer, and a pharmaceutically acceptable carrier. In other embodiments the adjuvant is HRA-5, a carbomer, or mineral oil.

In some embodiments, the compositions also include inactivated or live, attenuated ERAV and/or ERBV in combination with the following inactivated or live, attenuated viral strains or antigens and combinations of strains and antigens: West Nile Virus; Eastern Equine Encephalomyelitis; Western Equine Encephalomyelitis; Venezuelan Equine Encephalomyelitis; Tetanus Toxoid; Eastern Equine Encephalomyelitis and Western Equine Encephalomyelitis; Eastern Equine Encephalomyelitis and Venezuelan Equine Encephalomyelitis; Eastern Equine Encephalomyelitis and Tetanus Toxoid; Eastern Equine Encephalomyelitis, Western Equine Encephalomyelitis, and Venezuelan Equine Encephalomyelitis; Eastern Equine Encephalomyelitis, Western Equine Encephalomyelitis, and Tetanus Toxoid; Eastern Equine Encephalomyelitis, Western Equine Encephalomyelitis, Venezuelan Equine Encephalomyelitis and Tetanus Toxoid; Western Equine Encephalomyelitis and Venezuelan Equine Encephalomyelitis; Western Equine Encephalomyelitis and Tetanus Toxoid; Western Equine Encephalomyelitis, Venezuelan Equine Encephalomyelitis, and Tetanus Toxoid; Venezuelan Equine Encephalomyelitis and Tetanus Toxoid; and Eastern Equine Encephalomyelitis, Venezuelan Equine Encephalomyelitis and Tetanus Toxoid, or antigens or antigenic components thereof. A preferred combination of these specified combinations includes ERAV and/or ERBV in combination with antigens or antigenic components of inactivated viruses of West Nile Virus, Eastern Equine Encephalomyelitis, Western Equine Encephalomyelitis, Venezuelan Equine Encephalomyelitis, and Tetanus Toxoid. Another preferred combination includes ERAV and/or ERBV in combination with antigens or antigenic components of Eastern Equine Encephalomyelitis, Western Equine Encephalomyelitis, Venezuelan Equine Encephalomyelitis, and Tetanus Toxoid. Preferred ERAV include ERAV/ON/05 (ATCC Accession No. PTA-11828), ERAV strain which comprises a genomic sequence whose reverse transcript has a 5'UTR comprising the nucleotide sequence of SEQ ID NO: 1, which comprises a genomic sequence whose reverse transcript has a nucleotide sequence with greater than 95%, greater than 96%, greater than 97%, greater than 98% or greater than 99% identity to the nucleotide sequence of SEQ ID NO: 2 and, when not inactivated or attenuated, is active to infect and replicate in host cells and/or encodes functional ERAV proteins, or which encodes a polyprotein having an amino acid sequence with greater than 95%, greater than 96%, greater than 97%, greater than 98% or greater than 99% identity to the amino acid sequence of SEQ ID NO: 3, which polyprotein contains functional ERAV proteins (i.e., active in viral infection and replication). The ERAV strain may also comprise a genomic sequence which, when reverse transcribed, has a nucleotide sequence of SEQ ID NO: 2 or which encodes a polyprotein with an amino acid sequence of SEQ ID NO: 3. Preferred ERBV is a strain having ATCC Accession No: PTA-11829, or which comprises a genomic sequence whose reverse transcript has a nucleotide sequence with greater than 95%, greater than 96%, greater than 97%, greater than 98% or greater than 99% identity to the nucleotide sequence of the reverse transcript of the genome of the ERBV strain having ATCC Accession No. PTA-11829 and, when not inactivated, is active to infect and replicate in host cells and/or encodes functional ERBV proteins, or which encodes a polyprotein having an amino acid sequence with greater than 95%, greater than 96%, greater than 97%, greater than 98% or greater than 99% identity to the amino acid sequence of the polyprotein of the strain with ATCC Accession No. PTA-11829, which polyprotein contains functional ERBV proteins (i.e., active in viral infection and replication). In each such specified combination, an adjuvant or combination of adjuvants can be used such as, HRA-5, carbomer or with carbopol. The NJO strain of Eastern Equine Encephalomyelitis, the Fleming strain of Western Equine Encephalomyelitis strain, and the TC-83 strain of Venezuelan Equine Encephalomyelitis strain are all representative strains of these vaccine components.

Further preferred embodiments of the present invention include immunogenic compositions made using each of the specified combination vaccines listed above and adding antigens or inactivated or attenuated viruses from Equine Herpesvirus, preferably type 1, type 4, (EHV1 and/or EHV4) or combinations thereof.

Still further variations of each of the specified combination vaccines or immunogenic compositions listed above, including those that include EHV1 and/or EHV4 can be made by adding in antigens or inactivated or attenuated viruses from Equine influenza virus (EIV). Preferred embodiments incorporating Equine influenza virus include inactivated or live, attenuated: ERAV and/or ERBV and at least one inactivated or live, attenuated strain of each of WNV, Equine Influenza Virus, and Tetanus Toxoid; ERAV and/or ERBV and at least one inactivated or live, attenuated strain of each of WNV, Equine Influenza Virus, Tetanus Toxoid, and Eastern Equine Encephalomyelitis; ERAV and/or ERBV and at least one strain of each of WNV, Equine Influenza Virus, Tetanus Toxoid, Eastern Equine Encephalomyelitis, and Western Equine Encephalomyelitis; ERAV and/or ERBV and at least one strain of each of WNV, Equine Influenza Virus, Tetanus Toxoid, Eastern Equine Encephalomyelitis, Western Equine Encephalomyelitis; and Venezuelan Equine Encephalomyelitis; ERAV and/or ERBV and at least one strain of each of WNV, Equine Influenza Virus, and Eastern Equine Encephalomyelitis; ERAV and/or ERBV and, at least one strain of each of WNV, Equine Influenza Virus, and Western Equine Encephalomyelitis; ERAV and/or ERBV and at least one strain of each of WNV, Equine Influenza Virus, and Venezuelan Equine Encephalomyelitis; ERAV and/or ERBV and at least one strain of each of WNV, Equine Influenza Virus, Eastern Equine Encephalomyelitis, and Western Equine Encephalomyelitis; ERAV and/or ERBV and at least one strain of each of WNV, Equine Influenza Virus, Eastern Equine Encephalomyelitis, and Venezuelan Equine Encephalomyelitis; ERAV and/or ERBV and at least one strain of each of WNV, Equine Influenza Virus, Western Equine Encephalomyelitis, and Venezuelan Equine Encephalomyelitis; ERAV and/or ERBV and at least one strain of each of WNV, Equine Influenza Virus, Western Equine Encephalomyelitis, and tetanus toxoid; ERAV and/or ERBV and at least one strain of each of WNV, Equine Influenza Virus, Venezuelan Equine Encephalomyelitis, and tetanus toxoid; ERAV and/or ERBV and at least one strain of each of WNV, Equine Influenza Virus, Venezuelan Equine Encephalomyelitis, Western Equine Encephalomyelitis, and tetanus toxoid; and ERAV and/or ERBV and at least one strain of each of WNV, Equine Influenza Virus, Venezuelan Equine Encephalomyelitis, Eastern Equine Encephalomyelitis, and tetanus toxoid, wherein the aforementioned strains are inactivated or live, attenuated. In each specified embodiment one or more inactivated or live, attenuated strains of Equine Influenza Virus may be present. Preferred strains of Equine Influenza virus include Influenza A/equine-2/Ohio/03, Influenza A/equine-2/New Market/2/93, Influenza A/equine-2/Kentucky/95, and combinations thereof. In all of the combinations listed above, it is preferred to use at least two inactivated or live, attenuated strains of Equine Influenza Virus and still more preferred to use at least 3 strains of Equine Influenza Virus.

Preferred embodiments incorporating Equine Herpes Virus include: ERAV and/or ERBV and at least one strain of each of WNV, Equine Influenza Virus, Tetanus Toxoid, and Equine Herpes Virus; ERAV and/or ERBV and at least one strain of each of WNV, Equine Influenza Virus, Tetanus Toxoid, Eastern Equine Encephalomyelitis, and Equine Herpes Virus; ERAV and/or ERBV and at least one strain of each of WNV, Equine Influenza Virus, Tetanus Toxoid, Eastern Equine Encephalomyelitis, Western Equine Encephalomyelitis, and Equine Herpes Virus; ERAV and/or ERBV and at least one strain of each of WNV, Equine Influenza Virus, Tetanus Toxoid, Eastern Equine Encephalomyelitis, Western Equine Encephalomyelitis; Venezuelan Equine Encephalomyelitis, and Equine Herpes Virus; ERAV and/or ERBV and at least one strain of each of WNV, Equine Influenza Virus, and Eastern Equine Encephalomyelitis; ERAV and/or ERBV and at least one strain of each of WNV, Equine Influenza Virus, Western Equine Encephalomyelitis and Equine Herpes Virus; ERAV and/or ERBV and at least one strain of each of WNV, Equine Influenza Virus, Venezuelan Equine Encephalomyelitis, and Equine Herpes Virus; ERAV and/or ERBV and at least one strain of each of WNV, Equine Influenza Virus, Eastern Equine Encephalomyelitis, Western Equine Encephalomyelitis, and ERAV and/or ERBV and at least one strain of each of WNV, Equine Influenza Virus, Eastern Equine Encephalomyelitis, Venezuelan Equine Encephalomyelitis, and Equine Herpes Virus; ERAV and/or ERBV and at least one strain of each of WNV, Equine Influenza Virus, Western Equine Encephalomyelitis, Venezuelan Equine Encephalomyelitis, and Equine Herpes Virus; ERAV and/or ERBV and at least one strain of each of WNV, Equine Influenza Virus, Western Equine Encephalomyelitis, Tetanus Toxoid, and Equine Herpes Virus; ERAV and/or ERBV and at least one strain of each of WNV, Equine Influenza Virus, Venezuelan Equine Encephalomyelitis, tetanus toxoid, and Equine Herpes Virus; ERAV and/or ERBV and at least one strain of each of WNV, Equine Influenza Virus, Venezuelan Equine Encephalomyelitis, Western Equine Encephalomyelitis, Tetanus Toxoid, and Equine Herpes Virus; and ERAV and/or ERBV and at least one strain of each of WNV, Equine Influenza Virus, Venezuelan Equine Encephalomyelitis, Eastern Equine Encephalomyelitis, Tetanus Toxoid, and Equine Herpes Virus, wherein the aforementioned strains are inactivated or live, attenuated. In all of the combinations listed above, it is preferred to use at least two strains of inactivated or live, attenuated Equine Influenza Virus and still more preferred to use at least 3 strains of inactivated or live, attenuated Equine Influenza Virus. Additionally, in all combinations above, the "at least one" strain of Equine Herpes virus is preferred to be selected from the group consisting of inactivated EHV-1 and EHV-4. In some preferred forms, both inactivated or live, attenuated strains, EHV-1 and EHV-4, will be included in the immunogenic composition. In other preferred forms, just EHV-1 will be included. In a preferred combination, the inactivated or live, attenuated ERAV strain is ERAV/ON/05, an ERAV strain which comprises a genomic sequence whose reverse transcript has a 5'UTR comprising the nucleotide sequence of SEQ ID NO: 1, which comprises a genomic sequence whose reverse transcript has a nucleotide sequence with greater than 95%, greater than 96%, greater than 97%, greater than 98% or greater than 99% identity to the nucleotide sequence of SEQ ID NO: 2 and, when not inactivated, is active to infect and replicate in host cells and/or encodes functional ERAV proteins, or which encodes a polyprotein having an amino acid sequence with greater than 95%, greater than 96%, greater than 97%, greater than 98% or greater than 99% identity to the amino acid sequence of SEQ ID NO: 3, which polyprotein contains functional ERAV proteins (i.e., active in viral infection and replication). The ERAV strain may also comprise a genomic sequence which, when reverse transcribed, has a nucleotide sequence of SEQ ID NO: 2 or which encodes a polyprotein with an amino acid sequence of SEQ ID NO: 3. In other preferred combinations, the ERBV is a strain having ATCC Accession No: PTA-11828, or which comprises a genomic sequence whose reverse transcript has a nucleotide sequence with greater than 95%, greater than 96%, greater than 97%, greater than 98% or greater than 99% identity to the nucleotide sequence of the reverse transcript of the genome of the ERBV strain having ATCC Accession No. PTA-11828 and, when not inactivated or attenuated, is active to infect and replicate in host cells and/or encodes functional ERBV proteins, or which encodes a polyprotein having an amino acid sequence with greater than 95%, greater than 96%, greater than 97%, greater than 98% or greater than 99% identity to the amino acid sequence of the polyprotein of the strain with ATCC Accession No. PTA-11828, which polyprotein contains functional ERBV proteins (i.e., active in viral infection and replication).

The immunogenic compositions as disclosed herein can be administered in any immunogenically effective dose. In a preferred embodiment, the immunogenic composition is administered as a single dose. Preferably, the dose has a total volume between about 0.5 mL and about 2.5 mL, more preferably between about 0.6 mL and about 2.0 mL, even more preferably between about 0.7 mL and about 1.75 mL, still more preferably between about 0.8 mL and about 1.5 mL, even more preferably between about 0.9 mL and about 1.25 mL, with a single dose about 1.0 mL being the most preferred.

In another embodiment, the immunogenic composition is administered with a first dose being administered prior to the administration of a second (booster) dose. Preferably, the second dose is administered at least about 15 days after the first dose. More preferably, the second dose is administered between about 15 and about 28 days after the first dose. Even more preferably, the second dose is administered at least about 17 days after the first dose. Still more preferably, the second dose is administered between about 17 and about 25 days after the first dose. Even more preferably, the second dose is administered at least about 19 days after the first dose. Still more preferably, the second dose is administered between about 19 and about 23 days after the first dose. Most preferably the second dose is administered at least about 21 days after the first dose. In a preferred embodiment, both the first and second doses of the immunogenic composition are in the same amount. Preferably, each dose is in the preferred amounts specified above, with a dose of about 1 mL for the first and second dose being most preferred. In addition to the first and second dose regimen, an alternate embodiment comprises further subsequent doses. For example, a third, fourth, or fifth dose could be administered in these embodiments. Preferably, subsequent third, fourth, and fifth dose regimens are administered in the same amount as the first dose, with the time frame between the doses being consistent with the timing between the first and second doses mentioned above, although the timing may also vary.

In one embodiment the immunogenic composition is administered in three doses. In some embodiments the three doses are administered at three week intervals.

In an embodiment that comprises ERAV, preferably ERAV/ON/05, the amount of ERAV in the immunogenic composition is at least about $10^{2.0}$ TCID$_{50}$/dose. More preferably, the amount of ERAV is between about $10^{2.0}$ TCID$_{50}$/dose to about $10^{10.0}$ TCID$_{50}$/dose. Still more preferably, the amount of ERAV is at least about $10^{2.5}$ TCID$_{50}$/dose. Even more preferably, the amount of ERAV is between about $10^{2.5}$ TCID$_{50}$/dose to about $10^{9.5}$ TCID$_{50}$/dose. Still more preferably, the amount of ERAV is at least about $10^{3.0}$ TCID$_{50}$/dose. Even more preferably, the amount of ERAV is between about $10^{3.0}$ TCID$_{50}$/dose to about $10^{9.0}$ TCID$_{50}$/dose. Still more preferably, the amount of ERAV is at least about $10^{3.5}$ TCID$_{50}$/dose. Even more preferably, the amount of ERAV is between about $10^{3.5}$ TCID$_{50}$/dose to about $10^{9.0}$ TCID$_{50}$/dose. Still more preferably, the amount of ERAV is between about $10^{6.5}$ TCID$_{50}$/dose and about $10^{8.5}$ TCID$_{50}$/dose. More preferably, the amount of ERAV is between about $10^{7.0}$ TCID$_{50}$/dose and about $10^{9.0}$ TCID$_{50}$/dose. The TCID$_{50}$ values of an inactivated or attenuated ERAV or any other inactivated or attenuated vaccine refer in general to the viral content in the final vaccine that however is equivalent to the viral content calculated for the vaccine composition prior to the inactivation of its virus. Preferably, the immunogenic composition of the present invention stimulates serum neutralizing antibodies to ERAV at a titer of at least 1:112, 1:300, 1:500, 1:700, 1:900, 1:1000, or 1:1500

In an embodiment that comprises ERBV, preferably a strain having ATCC Accession NO: PTA-11829, the amount of ERBV is at least about $10^{2.0}$ TCID$_{50}$/dose. More preferably, the amount of ERBV is between about $10^{2.0}$ TCID$_{50}$/dose to about $10^{10.0}$ TCID$_{50}$/dose. Still more preferably, the amount of ERBV is at least about $10^{2.5}$ TCID$_{50}$/dose. Even more preferably, the amount of ERBV is between about $10^{2.5}$ $TCID_{50}$/dose to about $10^{9.5}$ $TCID_{50}$/dose. Still more preferably, the amount of ERBV is at least about $10^{3.0}$ $TCID_{50}$/dose. Even more preferably, the amount of ERBV is between about $10^{3.0}$ $TCID_{50}$/dose to about $10^{9.0}$ $TCID_{50}$/dose. Still more preferably, the amount of ERBV is at least about $10^{3.5}$ $TCID_{50}$/dose. Even more preferably, the amount of ERBV is between about $10^{3.5}$ $TCID_{50}$/dose to about $10^{9.0}$ $TCID_{50}$/dose. Sill more preferably, the amount of ERBV is between about $10^{6.5}$ $TCID_{50}$/dose and about $10^{8.5}$ $TCID_{50}$/dose. More preferably, the amount of ERBV is between about $10^{7.0}$ $TCID_{50}$/dose and about $10^{9.0}$ $TCID_{50}$/dose. The $TCID_{50}$ values of an inactivated ERBV or any other inactivated vaccine refer in general to the viral content in the final vaccine that however is equivalent to the viral content calculated for the vaccine composition prior to the inactivation of its virus. Preferably, the immunogenic composition of the present invention stimulates serum neutralizing antibodies to ERBV at a titer of at least 1:4 or higher. In some embodiments, the titer is at least 1:5, 1:6, 1:7, 1:8, 1:9, 1:10, 1:11; 1:12, 1:13, 1:14, or 1:15 or higher. In some embodiments, the titer is at least 1:64, 1:256, or 1:512 or higher. In some embodiments, the titer is at least 1:1024 or higher. In some embodiments, the titer is at least 1:2048, 1:1536, 1:3072, 1:4096, 1:6144, 1:8192, 1:12288, or 1:32769 or higher. In some embodiments, the titer is no more than 1:300, 1:1050, 1:32000, 1:70000, or 1:140000.

In one embodiment, in each dose of an embodiment of the present invention that comprises one or more additional equine antigens, the amount of Eastern Equine Encephalomyelitis or Venezuelan Equine Encephalomyelitis in any dose is preferably at least about $10^{5.5}$ $TCID_{50}$/dose. Even more preferably, the dose is between about $10^{5.5}$ $TCID_{50}$/dose and about $10^{9.5}$ $TCID_{50}$/dose. Still more preferably, the dose is at least about $10^{6.0}$ $TCID_{50}$/dose. Still more preferably, the dose is between about $10^{6.0}$ $TCID_{50}$/dose and about $10^{9.0}$ $TCID_{50}$/dose. Even more preferably, the dose is at least about $10^{6.5}$ $TCID_{50}$/dose. Still more preferably, the dose is between about $10^{6.5}$ $TCID_{50}$/dose and about $10^{9.5}$ $TCID_{50}$/dose. Even more preferably, the dose is at least about $10^{7.0}$ $TCID_{50}$/dose. Most preferably, the dose is between about $10^{6.7}$ $TCID_{50}$ and about $10^{9.2}$ $TCID_{50}$/dose.

In an embodiment that comprises inactivated or killed WNV or antigen, the amount of WNV or antigen is at least about $10^{2.0}$ $TCID_{50}$/dose. More preferably, the WNV or antigen is between about $10^{2.0}$ $TCID_{50}$/dose to about $10^{10.0}$ $TCID_{50}$/dose. Still more preferably, the WNV or antigen is at least about $10^{2.5}$ $TCID_{50}$/dose. Even more preferably, the WNV or antigen is between about $10^{2.5}$ $TCID_{50}$/dose to about $10^{9.5}$ $TCID_{50}$/dose. Still more preferably, the WNV or antigen is at least about $10^{3.0}$ $TCID_{50}$/dose. Even more preferably, the WNV or antigen is between about $10^{3.0}$ $TCID_{50}$/dose to about $10^{9.0}$ $TCID_{50}$/dose. Still more preferably, the WNV or antigen is at least about $10^{3.5}$ $TCID_{50}$/dose. Even more preferably, the WNV or antigen is between about $10^{3.5}$ $TCID_{50}$/dose to about $10^{9.0}$ $TCID_{50}$/dose. Most preferably, the WNV or antigen is between about $10^{7.0}$ $TCID_{50}$/dose and about $10^{9.0}$ $TCID_{50}$/dose. The $TCID_{50}$ values of an inactivated WNV vaccine or any other inactivated vaccine refer in general to the antigen content in the final vaccine that however is equivalent to the antigen content calculated for the vaccine composition prior to the inactivation of its antigen. Preferably, the immunogenic composition of the present invention stimulates serum neutralizing antibodies to WNV at a titer of at least 1:4 or higher. In some embodiments the titer is at least 1:5, 1:6, 1:7, 1:8, 1:9, 1:10, 1:11; 1:12, 1:13, 1:14, or 1:15 or higher. In some embodiments, the titer is no more than 1:300, 1:1050, 1:32000, 1:70000, or 1:140000. In a preferred embodiment, in each dose of an embodiment of the present invention that comprises additional equine antigen, the amount of Eastern Equine Encephalomyelitis or Venezuelan Equine Encephalomyelitis in any dose is preferably at least about $10^{5.5}$ $TCID_{50}$/dose. Even more preferably, the dose is between about $10^{5.5}$ $TCID_{50}$/dose and about $10^{9.5}$ $TCID_{50}$/dose. Still more preferably, the dose is at least about $10^{6.0}$ $TCID_{50}$/dose. Still more preferably, the dose is between about $10^{6.0}$ $TCID_{50}$/dose and about $10^{9.0}$ $TCID_{50}$/dose. Even more preferably, the dose is at least about $10^{6.5}$ $TCID_{50}$/dose. Still more preferably, the dose is between about $10^{6.5}$ $TCID_{50}$/dose and about $10^{9.5}$ $TCID_{50}$/dose. Even more preferably, the dose is at least about $10^{7.0}$ $TCID_{50}$/dose. Most preferably, the dose is between about $10^{6.7}$ $TCID_{50}$ and about $10^{9.2}$ $TCID_{50}$/dose.

Preferably, the Western Equine Encephalomyelitis antigen, when present in the composition of the present invention, is in an amount of at least about $10^{6.2}$ PFU/mL. Even more preferably, the amount is between about $10^{6.2}$ PFU/mL and about $10^{10.2}$ PFU/mL. Still more preferably, the amount is at least about $10^{6.7}$ PFU/mL. Even more preferably, the amount is between about $10^{6.5}$ PFU/mL and about $10^{9.7}$ PFU/mL. Still more preferably, the amount is at least about $10^{7.2}$ PFU/mL. Even more preferably, the amount is between about $10^{7.2}$ PFU/mL and about $10^{9.2}$ PFU/mL. Still more preferably, the amount is at least about $10^{77}$ PFU/mL with between about $10^{6.5}$ PFU/dose and about $10^{9.0}$ PFU/mL being the most preferred.

In another preferred embodiment, the amount of tetanus toxoid, if present in the composition of the present invention, is in an amount of at least about 3 CPU, more preferably, between about 3 CPU and about 20 CPU, still more preferably, at least about 4 CPU, and most preferably, at least about 5 CPU but not more than about 20 CPU.

In an alternate embodiment, where one or more strains of Equine Influenza Virus is present, the amount of Equine Influenza present in the composition is in an amount of at least about $10^{5.0}$ $TCID_{50}$/mL. More preferably, the Equine Influenza is in an amount of between about $10^{5.0}$ $TCID_{50}$/mL to about $10^{9.0}$ $TCID_{50}$/mL, and, more preferably, at least about $10^{6.0}$ $TCID_{50}$/mL. Still more preferably, the amount is between about $10^{6.0}$ $TCID_{50}$/mL to about $10^{8.0}$ $TCID_{50}$/mL and, more preferably, the amount is at least about $10^{6.5}$ $TCID_{50}$/mL. Still more preferably, the amount is between about $10^{6.5}$ $TCID_{50}$/mL to about $10^{7.5}$ $TCID_{50}$/mL, with the most preferred amount being between about $10^{6.7}$ $TCID_{50}$/mL to about $10^{7.3}$ $TCID_{50}$/mL.

In an embodiment that comprises Equine Herpes Virus, the amount of Equine Herpes Virus in each dose is at least about $10^{6.0}$ $TCID_{50}$/mL. More preferably, Equine Herpes Virus is present in the composition in an amount of between about $10^{6.0}$ $TCID_{50}$/mL to about $10^{9.5}$ $TCID_{50}$/mL and, more preferably, in an amount of about $10^{7.0}$ $TCID_{50}$/mL. Still more preferably, Equine Herpes Virus is present in an amount between about $10^{7.5}$ $TCID_{50}$/mL to about $10^{9.0}$ $TCID_{50}$/mL and, more preferably, in an amount of about $10^{8.0}$ $TCID_{50}$/mL. Still more preferably, Equine Herpes Virus is present in an amount of between about $10^{8.0}$ $TCID_{50}$/mL to about $10^{9.0}$ $TCID_{50}$/mL and, most preferably, in an amount of about $10^{8.50}$ $TCID_{50}$/mL.

In yet another preferred embodiment, a vaccine composition comprising the chronologically contemporary and epidemiologically prevalent strains of ERAV and/or ERBV is provided. Preferably the composition comprises ERAV/ON/05 and/or a ERBV strain having ATCC Accession NO: PTA-11829. In specific embodiments, the ERAV strain comprises a genomic sequence whose reverse transcript has a 5'UTR comprising the nucleotide sequence of SEQ ID NO: 1. In some embodiments, the ERAV strain comprises a genomic sequence whose reverse transcript has a nucleotide sequence with greater than 95%, greater than 96%, greater than 97%, greater than 98% or greater than 99% identity to the nucleotide sequence of SEQ ID NO: 2 and, when not inactivated, is active to infect and replicate in host cells and/or encodes functional ERAV proteins, or which encodes a polyprotein having an amino acid sequence with greater than 95%, greater than 96%, greater than 97%, greater than 98% or greater than 99% identity to the amino acid sequence of SEQ ID NO: 3, which polyprotein contains functional ERAV proteins (i.e., active in viral infection and replication). In some embodiments, the ERAV strain comprises a genomic sequence which, when reverse transcribed, has a nucleotide sequence of SEQ ID NO: 2 or which encodes a polyprotein with an amino acid sequence of SEQ ID NO: 3. In some embodiments, the ERBV is a strain having ATCC Accession No: PTA-11829. In some embodiments, the ERBV strain comprises a genomic sequence whose reverse transcript has a nucleotide sequence with greater than 95%, greater than 96%, greater than 97%, greater than 98% or greater than 99% identity to the nucleotide sequence of the reverse transcript of the genome of the ERBV strain having ATCC Accession No. PTA-11829 and, when not inactivated or attenuated, is active to infect and replicate in host cells and/or encodes functional ERBV proteins, or which encodes a polyprotein having an amino acid sequence with greater than 95%, greater than 96%, greater than 97%, greater than 98% or greater than 99% identity to the amino acid sequence of the polyprotein of the strain with ATCC Accession No. PTA-11829, which polyprotein contains functional ERBV proteins (i.e., active in viral infection and replication). Such a composition will generally improve the efficacy of the composition.

The present invention additionally provides for a method of reduction of the incidence of and/or severity of clinical signs associated with, ERAV and/or ERBV infection in an animal, preferably a horse. Such methods generally comprise the step of administering a vaccine composition comprising an inactivated or live, attenuated strain of an ERAV and/or ERBV and a pharmaceutically acceptable carrier. In particular embodiments, the ERAV is ERAV/ON/05, or the ERAV strain comprises a genomic sequence whose reverse transcript has a 5'UTR comprising SEQ ID NO: 1. In some embodiments, the ERAV strain comprises a genomic sequence whose reverse transcript has a nucleotide sequence with greater than 95%, greater than 96%, greater than 97%, greater than 98% or greater than 99% identity to the nucleotide sequence of SEQ ID NO: 2 and, when not inactivated, is active to infect and replicate in host cells and/or encodes functional ERAV proteins, or which encodes a polyprotein having an amino acid sequence with greater than 95%, greater than 96%, greater than 97%, greater than 98% or greater than 99% identity to the amino acid sequence of SEQ ID NO: 3, which polyprotein contains functional ERAV proteins (i.e., active in viral infection and replication). In some embodiments, the ERAV strain comprises a genomic sequence which, when reverse transcribed, has a nucleotide sequence of SEQ ID NO: 2 or which encodes a polyprotein with an amino acid sequence of SEQ ID NO: 3. In some embodiments, the ERBV is a strain having ATCC Accession No: PTA-11829. In some embodiments, the ERBV strain comprises a genomic sequence whose reverse transcript has a nucleotide sequence with greater than 95%, greater than 96%, greater than 97%, greater than 98% or greater than 99% identity to the nucleotide sequence of the reverse transcript of the genome of the ERBV strain having ATCC Accession No. PTA-11829 and, when not inactivated or attenuated, is active to infect and replicate in host cells and/or encodes functional ERBV proteins, or which encodes a polyprotein having an amino acid sequence with greater than 95%, greater than 96%, greater than 97%, greater than 98% or greater than 99% identity to the amino acid sequence of the polyprotein of the strain with ATCC Accession No. PTA-11829, which polyprotein contains functional ERBV proteins (i.e., active in viral infection and replication). In some preferred embodiments, an adjuvant, particularly HRA-5, is added to the composition, and in other preferred forms, no adjuvant is provided.

In an alternate preferred embodiment, the method comprises administering a vaccine composition comprising one or more inactivated or live, attenuated strains of ERAV and/or ERBV in combination with immunologically effective amounts of antigenic components or inactivated strains from other equine pathogens. Preferably, the ERAV strain is ERAV/ON/05 (ATCC Accession No. PTA-11828) and the ERBV strain has ATCC Accession NO: PTA-11829. In certain such embodiments, the ERBV strain comprises a genomic sequence whose reverse transcript has a 5'UTR comprising SEQ ID NO: 1. In some embodiments, the ERAV strain comprises a genomic sequence whose reverse transcript has a nucleotide sequence with greater than 95%, greater than 96%, greater than 97%, greater than 98% or greater than 99% identity to the nucleotide sequence of SEQ ID NO: 2 and, when not inactivated or live, attenuated, is active to infect and replicate in host cells and/or encodes functional ERAV proteins, or which encodes a polyprotein having an amino acid sequence with greater than 95%, greater than 96%, greater than 97%, greater than 98% or greater than 99% identity to the amino acid sequence of SEQ ID NO: 3, which polyprotein contains functional ERAV proteins (i.e., active in viral infection and replication). In some embodiments, the ERAV strain comprises a genomic sequence which, when reverse transcribed, has a nucleotide sequence of SEQ ID NO: 2 or which encodes a polyprotein with an amino acid sequence of SEQ ID NO: 3. In some embodiments, the ERBV is a strain having ATCC Accession No: PTA-11829. In some embodiments, the ERBV strain comprises a genomic sequence whose reverse transcript has a nucleotide sequence with greater than 95%, greater than 96%, greater than 97%, greater than 98% or greater than 99% identity to the nucleotide sequence of the reverse transcript of the genome of the ERBV strain having ATCC Accession No. PTA-11829 and, when not inactivated or attenuated, is active to infect and replicate in host cells and/or encodes functional ERBV proteins, or which encodes a polyprotein having an amino acid sequence with greater than 95%, greater than 96%, greater than 97%, greater than 98% or greater than 99% identity to the amino acid sequence of the polyprotein of the strain with ATCC Accession No. PTA-11829, which polyprotein contains functional ERBV proteins (i.e., active in viral infection and replication).

In some embodiments of the method, the pathogens in combination with the ERAV and/or ERBV strains, are selected from the group consisting of antigens or inactivated or attenuated strains of EHV and EIV and combinations thereof. In some embodiments the pathogens are antigens. In some embodiments the EHV is EHV-1 or EHV-4 or a combination thereof. In other embodiments the EIV is selected from the group consisting of Clade 1 viruses, Clade 2 viruses, Influenza A/South Africa/2003, Influenza A/equine-2/Ohio/03, Influenza A/equine-2/New Market/2/93, Influenza A/equine-2/Kentucky/95, Influenza A/equine-2/Richmond/1/2007 and combinations thereof.

In still other embodiments of the method, the pathogens in combination with the ERAV and/or ERBV strains, are selected from the group consisting of antigens or inactivated or attenuated strains of WNV, Eastern Equine Encephalomyelitis, Western Equine Encephalomyelitis, and Venezuelan Equine Encephalomyelitis, and tetanus toxoid, and combinations thereof, and more preferably being those combinations described above. In another preferred embodiment, the vaccine of the present invention is combined with a suitable adjuvant and/or pharmaceutically acceptable carrier.

The present invention provides for reduction of the incidence of and/or severity of clinical symptoms associated with, ERAV and/or ERBV infection in a herd. Preferably, the severity and/or incidence of clinical symptoms in animals receiving the immunogenic composition of the present invention are reduced at least 10% in comparison to animals not receiving such an administration when both groups (animals receiving and animals not receiving the composition) are challenged with or exposed to infection by ERAV and/or ERBV. More preferably, the incidence or severity is reduced at least 20%, even more preferably, at least 30%, still more preferably, at least 40%, even more preferably, at least 50%, still more preferably, at least 60%, even more preferably, at least 70%, still more preferably, at least 80%, even more preferably, at least 90%, still more preferably, at least 95%, and most preferably, at least 100%, wherein the animals receiving the composition of the present invention exhibit no clinical symptoms, or alternatively exhibit clinical symptoms of reduced severity. Advantageously, the present invention also provides protection from heterologous strains (relative to the strain used in the composition) of pathogens.

The present invention further provides a method of stimulating serum neutralizing or serum hemagglutination antibodies to a pathogen selected from the group consisting of ERAV, ERBV, WNV, WEE, VEE, EEE, EHV, EIV, and combinations thereof by administering a composition in accordance with the present invention described herein. In particular embodiments, the ERAV is ERAV/ON/05, or the ERAV strain comprises a genomic sequence whose reverse transcript has a 5'UTR comprising SEQ ID NO: 1. In some embodiments, the ERAV strain comprises a genomic sequence whose reverse transcript has a nucleotide sequence with greater than 95%, greater than 96%, greater than 97%, greater than 98% or greater than 99% identity to the nucleotide sequence of SEQ ID NO: 2 and, when not inactivated or attenuated, is active to infect and replicate in host cells and/or encodes functional ERAV proteins, or which encodes a polyprotein having an amino acid sequence with greater than 95%, greater than 96%, greater than 97%, greater than 98% or greater than 99% identity to the amino acid sequence of SEQ ID NO: 3, which polyprotein contains functional ERAV proteins (i.e., active in viral infection and replication). In some embodiments, the ERAV strain comprises a genomic sequence which, when reverse transcribed, has a nucleotide sequence of SEQ ID NO: 2 or which encodes a polyprotein with an amino acid sequence of SEQ ID NO: 3. In some embodiments, the ERBV is a strain having ATCC Accession No: PTA-11829. In some embodiments, the ERBV strain comprises a genomic sequence whose reverse transcript has a nucleotide sequence with greater than 95%, greater than 96%, greater than 97%, greater than 98% or greater than 99% identity to the nucleotide sequence of the reverse transcript of the genome of the ERBV strain having ATCC Accession No. PTA-11829 and, when not inactivated or attenuated, is active to infect and replicate in host cells and/or encodes functional ERBV proteins, or which encodes a polyprotein having an amino acid sequence with greater than 95%, greater than 96%, greater than 97%, greater than 98% or greater than 99% identity to the amino acid sequence of the polyprotein of the strain with ATCC Accession No. PTA-11829, which polyprotein contains functional ERBV proteins (i.e., active in viral infection and replication). Preferably the compositions of the present invention stimulate serum neutralizing antibodies to ERAV and/or ERBV at a titer of at least 1:112, 1:120, 1:300, 1:500, 1:1000, or 1:1024, or higher.

The immunogenic composition of the present invention provides an extended duration of immunity against all strains present in the vaccine. Preferably, the duration of immunity against ERAV and/or ERBV is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

The immunogenic composition of the present invention also provides an extended duration of immunity against all antigens present in the vaccine. Preferably, the duration of immunity against West Nile is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against EIV is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against EHV is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against Western Equine Encephalomyelitis is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against Eastern Equine Encephalomyelitis is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against Venezuelan Equine Encephalomyelitis is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity against Tetanus Toxoid is at least 1 month, more preferably, the duration of immunity is at least 2 months, still more preferably, the duration of immunity is at least 3 months, even more preferably, the duration of immunity is at least 4-24 months, still more preferably, the duration of immunity is at least 6-24 months, even more preferably, the duration of immunity is at least 7-24 months, still more preferably, the duration of immunity is at least 8-24 months, even more preferably, the duration of immunity is at least 9-24 months, still more preferably, the duration of immunity is at least 10-24 months, and most preferably, the duration of immunity is at least 12-24 months.

Preferably, the duration of immunity of at least 12 months further relates to any combination of antigens forming the immunogenic composition of the present invention.

In one embodiment comprising an inactivated (or, alternatively live attenuated) ERAV and/or ERBV as disclosed herein, the immunogenic composition ameliorates shedding of infectious ERAV and/or ERBV to prevent spread of the virus to other susceptible animals. In some embodiments the compositions prevent shedding of the virus.

In one embodiment comprising EIV and/or EHV antigen, as described above, the immunogenic composition ameliorates shedding of infectious EIV or EHV to prevent spread of the virus to other susceptible animals.

In one embodiment, compositions in accordance with the present invention described herein overcome interference from passively acquired maternal immunity and stimulate active immunity and a reduction in the incidence of or severity of clinical signs of EIV infection in vaccinated animals against EIV.

In one embodiment of the present invention, an immunogenic composition comprising ERAV and/or ERBV, VEE, WEE, EEE, tetanus, WNV, equine rhinopneumonitis and equine influenza, all as described herein, demonstrates efficacy against ERAV, ERBV, VEE, WEE, EEE, tetanus, WNV, equine rhinopneumonitis and equine influenza after administration in accordance with the present invention. Preferably, such a composition will further include an adjuvant, preferably HRA-5, mineral oil and/or a carbomer, and a pharmaceutically acceptable carrier. In preferred forms, the composition will be administered in a single, 1 mL dose. In some embodiments composition is administered in two doses or preferably three doses, with each dose separated by 1, 2, 3, and 4 weeks.

Each of the immunogenic compositions described herein that include ERAV, particularly ERAV/ON/05 (ATCC Accessions NO: PTA-11828) and other strains as described supra, and/or ERBV, particularly a ERBV strain having ATCC Accession NO: PTA-11829, or others as also described supra, can be administered as described such that they reduce the incidence of or lessen the severity of clinical symptoms associated with ERAV and/or ERBV, such as pyrexia, elevations in temperature, increased lung sounds, lymphadenopathy, nasal discharge, ocular discharge, pharyngitis, edema of legs, cough, and in the case of ERAV, increased incidence of abortion in pregnant mares. In some aspects, the compositions lessen the amount or length of nasal or ocular discharge or the length of time that such symptoms are presented. In some aspects, animals inoculated with the compositions show no clinical symptoms of ERAV and/or ERBV infection one week or longer after exposure to ERAV and/or ERBV. In other aspects, animals inoculated with the compositions show no clinical symptoms of ERAV and/or ERBV infection when exposed to ERAV and/or ERBV. Clinical symptoms of ERAV and ERBV may be scored such as according to Table 3 in Example 2, Table 14 in Example 4, or Table 17 in Example 5.

Each of the immunogenic compositions described herein that include EIV antigen or inactivated EIV and can be administered as described such that they reduce the incidence of or lessen the severity of clinical symptoms associated with Equine Influenza Virus.

The present invention also provides a method for reducing the incidence of or lessening the severity of clinical symptoms associated with Equine Herpes Virus comprising the step of administering any one of the immunogenic compositions described above containing EHV antigen or inactivated or attenuated EHV to an animal.

The present invention also provides a method for reducing the incidence of clinical symptoms associated with West Nile Virus comprising the step of administering any one of the immunogenic compositions that includes WNV antigen or inactivated or attenuated WNV, as described herein, to an animal.

The present invention also provides a method for reducing the incidence of clinical symptoms associated with Equine Influenza Virus comprising the step of administering any one of the immunogenic compositions described above, that includes an EIV antigen or inactivated or attenuated EIV, to an animal.

The present invention further provides a method for reducing the incidence of clinical symptoms associated with Equine Herpes Virus comprising the step of administering any one of the immunogenic compositions described above that includes an EHV antigen or inactivated or attenuated EHV, to an animal.

The present invention provides a method of reducing the incidence of viral infection in a herd comprising the step of administering any one of the immunogenic compositions described above to an animal, wherein the reduction of incidence of infection, compared to herds not receiving the immunogenic composition, is from about 10% to about 50% reduction. In one embodiment the compositions provided herein reduce ERAV infection by 10% to 50%. In other embodiments the compositions provided herein reduce ERBV infection by 10% to 50%.

The present invention also provides a method of reducing the incidence of clinical symptoms associated with Equine Influenza Virus comprising the step of administering any one of the immunogenic compositions described above to an animal, wherein the reduction in clinical signs, compared to animals not receiving the immunogenic composition, is at least a 10% reduction in clinical signs.

The present invention provides a method of reducing the incidence and severity of clinical symptoms of ERAV or ERBV in a herd, wherein the clinical symptoms are selected from the group consisting of pyrexia, elevations in temperature, increased lung sounds, lymphadenopathy, nasal discharge, ocular discharge, pharyngitis, cough, edema of legs, and in the case of ERAV, increased incidence of abortion in pregnant mares.

The present invention provides a method of reducing the incidence and severity of clinical symptoms of EHV in a herd, wherein the clinical symptoms are selected from the group consisting of respiratory disease, abortion, reproductive complications, neurological disease, central nervous system disease, and combinations thereof.

The present invention provides a method for reducing the incidence of or lessening the severity of clinical symptoms associated with Equine Herpes Virus comprising the step of administering any one of the immunogenic compositions disclosed herein, that includes an EHV antigen or inactivated or attenuated EHV, to an animal.

The present invention provides a method for reducing the incidence of or lessening the severity of clinical symptoms associated with Equine Influenza Virus in a herd, comprising the step of administering any one of the immunogenic compositions disclosed herein, that includes an EIV antigen or inactivated or attenuated EIV, to an animal.

The present invention provides a method for reducing the incidence of or lessening the severity of clinical symptoms associated with West Nile Virus in a herd, comprising the step of administering any one of the immunogenic compositions disclosed herein, that includes a WNV antigen or inactivated or attenuated WNV, to an animal.

The present invention provides a method for reducing the incidence of or lessening the severity of clinical symptoms associated with Eastern Equine Encephalomyelitis in a herd, comprising the step of administering any one of the immunogenic compositions disclosed herein that includes an EEE virus antigen or an inactivated or attenuated EEE virus, to an animal.

The present invention further provides a method for reducing the incidence of or lessening the severity of clinical symptoms associated with Western Equine Encephalomyelitis in a herd, comprising the step of administering any one of the immunogenic compositions disclosed herein, that includes a WEE virus antigen or an inactivated or attenuated WEE virus, to an animal.

The present invention further provides a method for reducing the incidence of or lessening the severity of clinical symptoms associated with Venezuelan Equine Encephalomyelitis in a herd, comprising the step of administering any one of the immunogenic compositions disclosed herein, that includes a VEE virus antigen or an inactivated attenuated VEE virus, to an animal.

The aforementioned embodiments may be used in a combination therapy or as part of a immunization schedule in combination with other immunogenic agents and vaccines. In one embodiment, the compositions provided herein are used in combination with the immunogenic agents and vaccines described in WO 2010/025469, which is incorporated herein by reference in its entirety.

The present invention also provides a method of making any one of the immunogenic composition as described above and herein, comprising the steps of combining an inactivated or live, attenuated ERAV or ERBV with a suitable pharmaceutical carrier. In preferred forms, this method further comprises the step of adding one or more equine antigens or inactivated or attenuated viruses. A preferred group of equine antigens and viruses are selected from the group consisting of West Nile Virus, Western Equine Encephalomyelitis, Eastern Equine Encephalomyelitis, Venezuelan Equine Encephalomyelitis, EHV, and EIV, and tetanus toxoid, and combinations thereof. In some preferred forms, the methods described herein can further comprise a filtration step, wherein the final product is in a more pure form.

"About" refers to ±10% of the specified quantity.

"Animals" as used herein includes domesticated animals including dogs and hooved animals including equidae, and specifically, horses. In some embodiments, the term also refers to a human.

"Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), non-metabolizable oil, mineral and/or plant/vegetable and/or animal oils, polymers, carbomers, surfactants, natural organic compounds, plant extracts, carbohydrates, cholesterol, lipids, water-in-oil emulsion, oil-in-water emulsion, water-in-oil-in-water emulsion, HRA-3 (acrylic acid saccharide cross-linked polymer), HRA-3 with cottonseed oil (CSO), or preferably HRA-5 (acrylic acid polyol cross-linked polymer). The emulsion can be based in particular on light liquid paraffin oil (European Pharmacopeia type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.) John Wiley and Sons, NY, pp 51-94 (1995) and Todd et al., Vaccine 15:564-570 (1997). In a preferred embodiment the adjuvant is at a concentration of about 0.01 to about 50%, preferably at a concentration of about 2% to 30%, more preferably at a concentration of about 5% to about 25%, still more preferably at a concentration of about 7% to about 22%, and most preferably at a concentration of about 10% to about 20% by volume of the final product.

As used herein, "a pharmaceutically acceptable carrier" or "pharmaceutical carrier" includes any and all excipients, solvents, growth media, dispersion media, coatings, adjuvants, stabilizing agents, diluents, preservatives, inactivating agents, antimicrobial, antibacterial and antifungal agents, isotonic agents, adsorption delaying agents, and the like. Such ingredients include those that are safe and appropriate for use in veterinary applications. In some preferred embodiments, and especially those that include lyophilized immunogenic compositions, stabilizing agents for use in the present invention include stabilizers for lyophilization or freeze-drying.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

In a preferred embodiment, the immunogenic composition of the present invention is prepared comprising a preservative and a stabilizer; and, more preferably, the immunogenic composition of the present invention is prepared comprising Amphotericin, formaldehyde, gentamycin, EDTA, glycerol, and combinations thereof.

An "immunogenic or immunological composition" refers to a composition of matter that comprises at least one antigen, which elicits an immunological response in the host of a cellular and/or antibody-mediated immune response to the composition or vaccine of interest. Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of clinical signs normally displayed by an infected host, a quicker recovery time and/or a lowered duration or bacterial titer in the tissues or body fluids or excretions of the infected host.

The term "in need of such administration" or "in need of such administration treatment," as used herein means that the administration/treatment is associated with the boosting or improvement in health or any other positive medicinal effect on health of the animals which receive the immunogenic composition in accordance with the present invention, such as reducing the incidence or severity of a viral infection or disease.

"Equine rhinitis A virus (ERAV)" refers to an *Aphthovirus* in the family Picornaviridae, and was previously known as Equine rhinovirus 1. "ERAV" as used herein includes inactivated forms. In one embodiment, the ERAV is strain ERAV/ON/05 having accession number PTA-11829 deposited on Apr. 14, 2011 with the ATCC (American Type Culture Collection, P.O. Box 1549 Manassas, Va. 20108 USA) in accordance with the Budapest Treaty, and that was recovered from Rabbit-kidney-13 (RK-13) cell culture from a nasal swab from a horse in Ontario Canada in 2005. The ERAV/ON/05 when reverse transcribed and sequenced has SEQ ID NO: 1 in its 5' UTR region.

The reverse transcribed genomic sequence of ERAV/ON/05 is SEQ ID NO:2.

The polyprotein encoded by the genomic sequence of ERAV/ON/05 is SEQ ID NO:3.

The ERAV strains useful in the immunogenic compositions of the invention have reverse transcribed 5'UTR nucleotide sequences that have greater than 85%, 90%, 95%, 98%, 99% or 100% sequence identity to SEQ ID NO:1. In some embodiments, the ERAV strains have genomic sequences that when reverse transcribed into DNA are greater than 85%, 90%, 95%, 98%, 99% or 100% identical to SEQ ID NO:2 or have polyprotein coding sequences that are more than 97%, 98%, 99%, or 100% identical to the polyprotein coding sequence in SEQ ID NO:2. In some embodiments, the ERAV have polyproteins with an amino acid sequence greater than 95%, 95%, 97%, 98%, 99%, or 100% identical to SEQ ID NO:3 or to the VP1 sequence within SEQ ID NO:3. In yet other embodiments, the ERAV has an L protein, VP2, VP3, VP4, VP0, 2A, 2B, 2C, 3A, 3B, 3C or 3D, that have an amino acid sequence with greater than 80%, greater than 90%, greater than 99%, or 100% identity to the same protein found in SEQ ID NO:3. All of the ERAV strains are, when not inactivated or attenuated, infective and able to replicate in host cells.

"Equine rhinitis B virus (ERBV)" refers to an *Erbovirus* in the family Picornaviridae, and was previously known as Equine rhinovirus 2. "ERBV" as used herein includes inactivated forms. In one embodiment, the ERBV is a strain deposited with the ATCC that was recovered from Rabbit-kidney-13 (RK-13) cell culture from a nasal swab from a horse in Ontario Canada (ATCC Accession NO: PTA-11828) that was deposited with the ATCC (American Type Culture Collection, P.O. Box 1549 Manassas, Va. 20108 USA) on Apr. 14, 2011 under the Budapest Treaty. The ERBV strains useful in the immunogenic compositions of the invention have genomic sequences that when reverse transcribed into DNA are greater than 85%, 90%, 95%, 98%, 99% or 100% identical to the reverse transcript of the genomic sequence of the ERBV strain having ATCC Accession No. PTA-11829, or have polyprotein coding sequences that are more than 97%, 98%, 99%, or 100% identical to the polyprotein coding sequence of the ERBV strain having ATCC Accession No. PTA-11829. In some embodiments, the ERBV strains useful in the invention have polyproteins with an amino acid sequence greater than 95%, 95%, 97%, 98%, 99%, or 100% identical to the polyprotein sequence of the ERBV strain having ATCC Accession No. PTA-11829. In yet other embodiments, the ERBV has an L protein, VP-4, VP2, VP3, VP1, 2A, 2B, 2C, 3A (Vpg), 3B, 3 Cpro, 3Dpol that have an amino acid sequence with greater than 80%, greater than 90%, greater than 99%, or 100% identity to the same protein found in the ERBV strain having ATCC Accession No. PTA-11829. All of the ERBV strains are, when not inactivated or attenuated, infective and able to replicate in host cells.

The term "West Nile Virus" antigen means, but is not limited to the components of the WNV virion that are immunogenic when present in an animal, and most particularly protein components, such as envelope and non-structural proteins, of the WNV that provoke humoral or cellular immune responses when present in an animal. Such antigens can include DNA, protein subunits, modified live virus, and inactivated virus. In preferred forms of the invention, the WNV antigen or antigens comprise inactivated or killed, and even more preferably, North American dominant, WNV strains.

The term "North American West Nile Virus (strains)" refers to, but is not limited to any West Nile Virus strain that has ever been discovered on the North American continent. Preferably, a North American West Nile Virus strain has a sequence identity to the NY99 strain (GenBank accession no. AF196835 or NCBI reference sequence NC_00942.1 of at least 97%, even more preferably, at least 98%, still more preferably, at least 98.5%, more preferably, at least 99%, even more preferably, at least 99.2%, and, most preferably of at least 99.4%. WN02 is a representative example of a WNV strain that can be referred to as a North American Dominant West Nile Virus strain. Specifically, North American Dominant strains are those having at least 1 nucleotide change resulting in an amino acid change from the WN99 isolates. Strain NY99 (GenBank accession no. AF196835) serves as a reference strain for determining if a strain is North American Dominant. In addition, these strains may have one or more silent amino acid changes. In some embodiments, the nucleotide change results in an amino acid change in an envelope protein of the strain and, more preferably, the nucleotide change results in an amino acid change from valine to alanine. Preferably, this amino acid change is associated with a greater ability to replicate in the intermediate host, namely, the mosquito. More preferably, North American Dominant strains include either (and preferably both) a U to C mutation and a C to U mutation at positions 1442 and 2466 (in comparison to a North American strain, e.g., NY 99), respectively. Still more preferably, North American Dominant strains further include a mutation in the nucleotide sequence encoding the E protein and the C to U mutation at position 9352 in the sequence encoding the NS5 protein (again in comparison to a North American strain, e.g., NY 99). These preferred mutations are shown in Phylogenetic Analysis of North American West Nile Virus Isolates, 2001-2004: Evidence For the Emergence of a Dominant Genotype, C. Todd Davis, et. al, Virology 342, p. 252-265 (2005), the teaching and content of which is hereby incorporated by reference. West Nile Virus strains, for purposes of the present invention, are not limited to horse and equine West Nile Virus strains but encompass, while not being limited to, those West Nile Virus strains of bird origin, donkey origin, pig origin, human origin, mammal origin, and equine origin.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference).

These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity. In the present disclosure, it is understood that SEQ ID NO:1 (5' UTR) and SEQ ID NO:2 are the DNA sequences that result from reverse transcription of the 5' UTR and the entire genome of ERAV/ON/05, respectively. Likewise, SEQ ID NO: 3 refers to the amino acid sequence corresponding to the polyprotein encoded by the genomic sequence of ERAV/ON/05. Percent identity of a given ERAV strain in comparison to SEQ ID NO:1 or SEQ ID NO:2 is thus meant to refer to the corresponding DNA sequence resulting from reverse transcription and sequencing.

"$TCID_{50}$" refers to tissue culture infective dose infecting 50% of cells in a culture inoculated with the virus.

For purposes of the present invention the terms "strain" and "isolate" have the same meaning and are used interchangeably.

"Clinical signs" or "clinical symptoms" for ERAV and ERBV include but are not limited to pyrexia, elevation in temperature, increased lung sounds, lymphadenopathy, nasal discharge, ocular discharge, and cough, and pharyngitis. Still other signs or symptoms include anemia, anorexia, lymphadenitis of the head and neck, edema of the legs, lethargy, and pain. Additionally, clinical signs of ERAV and/or ERBV infections may include those associated with Equine Herpes virus and Equine Influenza virus. In one embodiment the clinical signs for ERAV include cough, pharyngitis, pyrexia, elevations in temperature, increased submandibular lymph node size, nasal discharge, and ocular discharge. In certain embodiments, the clinical signs of ERAV include an increased incidence of abortion in pregnant mares. In another embodiment the clinical signs to be addressed by an immunological composition disclosed herein are those of respiratory infections, such as those cause by one or more of ERAV, ERBV, EIV, EHV-1, and EHV-4.

"Clinical signs" or "clinical symptoms" of West Nile Virus, for purposes of this invention, include, but are not limited to, symptoms or lesions associated with encephalitis, viremia, anorexia, depression, fever, weakness, abnormal gait, paralysis of hind limbs, impaired vision, ataxia, aimless wandering, convulsions, inability to swallow, coma, posterior weakness, paralysis, poor coordination, depression and related behavior, tremors, convulsions, paddling of the limbs, neurological problems, swelling of the central nervous system, death, and combinations thereof. The clinical signs exhibited by an infected animal vary depending on the severity of infection.

"Clinical Signs" or "clinical symptoms" of Equine Herpes virus, for purposes of this invention include, but are not limited to, abortion, neurological deficiencies, respiratory disease, reproductive system deficiencies and failure, and symptoms relating to the central nervous system. Additionally, clinical symptoms of EHV1 include, but are not limited to, the phenomenon of foals infected with EHV1, exhibiting respiratory complications, passing the virus to the older members of the herd who then exhibit reproductive deficiencies, including abortion, and neurological deficiencies, normally exhibited in the central nervous system.

"Clinical Signs" or "clinical symptoms" of Eastern Equine Encephalomyelitis, Western Equine Encephalomyelitis, and Venezuelan Equine Encephalomyelitis, for purposes of the present invention are those symptoms normally known to be associated with encephalomyelitis, including, but are not limited to fever, nervous signs such as sensitivity to sound, periods of excitement, and restlessness, brain lesions, drowsiness, drooping ears, circling, abnormal gait, paralysis, loss of appetite, depression, head pressing, lack of coordination, long-term disability, brain damage, death, and combinations thereof. "Safety" as used herein, refers to the absence of adverse consequences in the vaccinated animal following vaccination, including but not limited to, potential reversion of vaccine virus to virulence and clinically significant side effects, such as persistent systemic illness or unacceptable inflammation at the site of vaccine administration.

"Reduction of the incidence and/or severity of clinical signs" or "reduction in the incidence and/or severity of clinical symptoms," as referred to herein, means reducing the number of infected animals in a group, reducing or eliminating the number of animals exhibiting clinical signs of infection, or reducing the severity of any clinical signs that are present in the animals, in comparison to wild-type infection. For example, such clinical signs included viremia, fever, antibody response, ocular discharge, nasal discharge, and histopathology. Preferably, these are reduced in animals receiving the composition of the present invention by at least 10% in comparison to animals not receiving the vaccination which may become infected. More preferably, clinical signs are reduced in animals receiving the composition of the present invention by at least 20%, more preferably by at least 30%, even more preferably by at least 40%, and even more preferably by at least 50%.

"Duration of Immunity," as used herein, refers to the minimum number of days during which an animal produces an immunogenic response such that the animal will be relatively immune from contracting a virus and/or benefit from reduction of incidence and/or severity of clinical signs, as described herein.

The term "inactivated" and "inactivated virus" refers to a previously virulent virus that has been heated or chemically treated to inactivate, kill, or otherwise modify the virus to substantially eliminate its virulent properties while retaining its immunogenicity. In a preferred embodiment, the inactivated viruses disclosed herein are inactivated by treatment with an inactivating agent. Suitable inactivating agents include beta-propiolactone, binary ethyleneimine, glutaraldenyde, and formaldehyde. In some embodiments, the inactivating agent is formaldehyde.

The terms "vaccine" and "immunogenic composition", when used herein, are meant to be used interchangeably.

Any West Nile Virus strain(s) or isolate(s) can be used in accordance with the present invention. In a preferred embodiment, the isolate is selected from one or more of the following: New York (Northeastern North American) Isolate (WN-NY 99), Horse Origin, 1999, New York (Northeastern North American) Isolate (WN-NY 99), Crow Origin, 1999, United States Department of Agricultures Isolate 292206 (USDA 2004), Donkey Origin, United States Department of Agriculture Isolate 405330 (USDA 2005), Horse Origin, North American Isolate (WN-Texas-2002/2003), Southeast Texas Coastal Isolate 2002, Mexico (Tabasco) Isolate 2003, and combinations thereof, and in a more preferred embodiment the isolate is selected from one or more of the following: United States Department of Agricultures Isolate 292206 (USDA 2004), Donkey Origin, United States Department of Agriculture Isolate 405330 (USDA 2005), Horse Origin, North American Isolate (WN-Texas-2002/2003), Southeast Texas Coastal Isolate 2002, Mexico (Tabasco) Isolate 2003, and combinations thereof. In a most preferred embodiment, the isolate is United States Department of Agriculture Isolate 405330 (USDA 2005), Horse Origin singularly or in combination with one or more isolates as listed above. In an additionally preferred embodiment, those isolates which are part of the North American West Nile Virus isolates are included. In yet another preferred embodiment North American Dominant West Nile Virus isolates are included. In addition to those listed above, specific isolates include, but are not limited to, WN02 and isolates which have at least 1, preferably at least 2, and even more preferably at least 3 nucleotide changes resulting in at least one amino acid change from the WN NY99 isolates, and most preferred are strains with the amino acid change from valine to alanine at position 159 of the envelope protein. Most preferred North American Dominant strains include, but are not limited to: NY2002Nassau, NY2002Clinton, NY2002Queens, GA20021, GA20022, TX20021, TX20022, IN2002, NY2003Albany, NY2003Suffolk, NY2003Chatauqua, CO20031, CO20032, TX2003, TX2003Harris4, TX2003Harris6, TX2003Harris7, TX2003Harris10, AZ2004, and TX2004Harris4, and combinations thereof. The strains of West Nile Virus useful in the vaccine or immunogenic composition of the present invention can be any strain or isolate. In a preferred embodiment, the North American Dominant West Nile Virus strain used is either E-159 (Horse Origin) or E-159 (Donkey Origin). A representative strain of such a North American Dominant WNV strain includes the Horse Origin 2005 strain deposited with the ATCC (ATCC Accession NO: PTA-9409), located at 10801 University Boulevard, Manassas, Va., 20110-2209, on Aug. 14, 2008, under the provisions of the Budapest Treaty. Equine Influenza strains useful in the vaccine or immunogenic composition of the present invention can be any strain or isolate. Representative strains include Equi-2/Ohio/03, deposited as ATCC Accession NO: PTA-9522, Equi-2/Kentucky/95, deposited as ATCC Accession NO: PTA-9523, and Equi-2/New Market/2/93, deposited as ATCC Accession NO: PTA-9524. Representative strains ATCC Accession Nos. PTA-9522, PTA-9523, and PTA-9524 were each deposited with the ATCC at 10801 University Boulevard, Manassas, Va., 20110-2209 on Sep. 23, 2008, under the provisions of the Budapest Treaty.

Equine Herpes Virus ("EHV") strains useful in the vaccine or immunogenic composition of the present invention can be any strain or isolate. Representative strains include EHV Subtype 1, deposited as ATCC Accession NO: PTA-9525, and EHV Subtype 4, deposited as ATCC Accession NO: PTA-9526. Representative strains ATCC Accession Nos. PTA-9525 and PTA-9526 were each deposited with the ATCC at 10801 University Boulevard, Manassas, Va., 20110-2209 on Sep. 23, 2008, under the provisions of the Budapest Treaty.

Western Equine Encephalomyelitis strains useful in the vaccine or immunogenic composition of the present invention can be any strain or isolate. A representative strain includes the Fleming Strain, deposited with the ATCC (ATCC Accession NO: PTA-9410), located at 10801 University Boulevard, Manassas, Va., 20110-2209, on Aug. 14, 2008, under the provisions of the Budapest Treaty.

Venezuelan Equine Encephalomyelitis strains useful in the vaccine or immunogenic composition of the present invention can be any strain or isolate. A representative strain includes the TC-83 strain, deposited with the ATCC (ATCC Accession NO: PTA-9411), located at 10801 University Boulevard, Manassas, Va., 20110-2209, on Aug. 14, 2008, under the provisions of the Budapest Treaty.

Eastern Equine Encephalomyelitis strains useful in the vaccine or immunogenic composition of the present invention can be any strain or isolate. A representative strain includes the NJO strain, deposited with the ATCC (ATCC Accession NO: PTA-9412), located at 10801 University Boulevard, Manassas, Va., 20110-2209, on Aug. 14, 2008, under the provisions of the Budapest Treaty.

Tetanus toxoid strains useful in the vaccine or immunogenic composition of the present invention can be any strain or isolate. A representative strain is that taken from a master seed of *Clostridium tetani* from The Massachusetts Department of Public Health Institute of Laboratories in Boston, Mass.

The vaccine or immunogenic composition as disclosed herein is safe for administration in ERAV or ERBV susceptible species, particularly equidae, at any age. In a preferred embodiment, the present invention is safe for administration to foals 12 months of age or older, more preferably, it is safe for administration to foals 10 months of age or older, more preferably, it is safe for administration to foals 8 months or older, more preferably, it is safe for administration to foals 6 months of age or older, more preferably, is safe for administration to foals 4 months of age or older, more preferably, it is safe for administration to foals 2 months of age or older, more preferably, it is safe for administration to foals 1 month of age or older, even more preferably, it is safe for administration to foals between 1 day and 1 month of age, and, most preferably, it is safe for administration to foals 1 day of age or older.

The compositions as disclosed herein can be administered in any conventional manner. Examples of administration methods include any that afford access by cells of the immune system to the immunogenic composition including oral, transdermal/intradermal, intravenous, subcutaneous, intramuscular, intraocular, intraperitoneal, intrarectal, intravaginal, intranasal, intragastrical, intratracheal, intrapulmonarial, or any combination thereof. In a preferred embodiment, the vaccine is administered parenterally, preferably intranasally, subcutaneously, or intramuscularly, and in the most preferred embodiment the vaccine is administered intramuscularly.

In one embodiment, provided is a method for preparing and immunogenic composition comprising an ERAV and/or ERAB as disclosed herein. In one embodiment, the method comprises:

a) infecting a susceptible cell line with ERAV or ERBV;
b) growing the infected cell line in growth media until a cytopathic effect (CPE) is attained;
c) harvesting the media;
d) filtering the media to yield a filtered media; and
e) contacting the filtered media with an inactivating agent to obtain the inactivated ERAV or ERBV.

In one embodiment, the method comprises providing strain ERAV/ON/05 or a ERBV strain having ATCC Accession NO: PTA-11829. These strains are used to infect a susceptible cell line having advantageous growth and secretion properties useful for vaccine preparation. A preferred susceptible cell line is a Vero cell line such as a Vero76 or an E-Vero cell line.

Suitable growth media include E199. This media may be supplemented with L-glutamine solution and an antibiotic such as gentamicin sulfate solution. In some embodiments the growth media is E199 supplemented with L-glutamine solution (up to 2 mM), and gentamicin sulfate solution (up to 30 µg/mL). In some embodiments, viral fluids are harvested when the cytopathic effect CPE reaches 75% or greater. The harvested media are pooled and filtered such as through 5.0 micron pore-size rated polypropylene filter cartridges. The strains are inactivated chemically such as by treatment with 0.1-0.2% formaldehyde solution over a suitable period of time, for example 48 hours to 72 hours and the resulting fluids are concentrated. In some embodiments, preservatives and adjuvants are next added. Suitable preservatives include one or more of Amphotericin B, gentamicin sulfate, and formaldehyde. In other embodiments the adjuvant is HRA-5. In still other embodiments the adjuvant is HRA-3 with cottonseed oil (CSO).

In one embodiment and in accordance with the methods disclosed herein, provided is an immunogenic composition comprising ERAV/ON/05 and/or a ERBV strain having ATCC Accession NO: PTA-11829 and Amphotericin B, gentamicin sulfate, formaldehyde, and HRA-5 prepared according to the methods disclosed herein.

EXAMPLES

The following examples are set forth below to illustrate specific embodiments of the present invention. These examples are merely illustrative and are understood not to limit the scope or the underlying principles of the present invention.

Example 1

This example illustrates one embodiment of a Equine Rhinitis A Virus composition in accordance with the present invention.

Materials and Methods

Equine Rhinitis A Virus strain ERAV/ON/05 (ATCC Accession No. PTA-11828) was recovered from Rabbit-kidney-13 (RK-13) cell culture from a nasal swab from a horse in Ontario Canada. The virus was passaged once on E-Vero cells to produce a high pre-titered master stock, and was then diluted with cell culture media to produce the Master Seed Virus. Master Cell Stock is an E-Vero cell line grown and maintained using E199 supplemented with L-Glutamine solution (up to 2 mM) and Gentamicin sulfate solution (up to 30 µg/mL). Inactivated ERAV/ON/05 was produced according to the following general procedure.

Frozen Master Cell Stock is thawed at room temperature (18-26° C.) and used to inoculate a range of pre-sterilized T-25 cm$^2$ up to T-150 cm$^2$ flasks or pre-sterilized 850 cm$^2$ or 1050 cm$^2$ PETG roller bottles. Thawed cells are suspended in growth medium at the rate of 0.15 to 0.40 mL per cm$^2$. Cells are incubated at 36-38° C. for up to seven days. Cultures planted from frozen stock may be re-fed with medium to remove residual Dimethyl Sulfoxide (DMSO), to remove excessive debris, to stimulate the growth of cultures which have not reached confluency, or to maintain viability of confluent cultures. Cells are passaged by decanting the spent medium and adding 1-10 mL (depending on the size of the vessel), of 25% trypsin-EDTA solution to each vessel. The vessels are agitated gently until the cells slough from the surface. The cells are removed from the vessels by rinsing with growth medium and pooled together. The range of cell culture passages is one to twenty.

Prior to inoculation, cell growth medium is decanted from cells that are at least 90% confluent. The cell sheet is rinsed with 20-50 mL of virus infection media (E199 supplemented with L-Glutamine solution (up to 2 mM) and Gentamicin sulfate solution (up to 30 µg/mL), then re-fed with virus infection media at the rate of 0.15 to 0.40 mL/cm$^2$. Vessels are then inoculated at a Multiplicity of Infection (MOI) of 0.0005 to 0.005. Roller bottle cultures are incubated at 36-38° C. for two to five days at 0.2-0.4 rpm.

During the growth period, cultures are checked for CPE microscopically and for gross contamination macroscopically. Unsuitable cultures are discarded after sterilization.

Virus fluids are harvested when CPE reaches 75% or greater. Roller bottles are swirled to remove loose cells, and fluids are pooled into sterile 2-20 L glass, plastic, or PETG bottles, 20 L sterile polypropylene containers or 2-200 L sterile stainless steel tanks appropriate for clarification. Pooled fluids may be held for up to seven days at 2-8° C. prior to clarification.

Only fluids from monolayer cultures showing evidence of viral infection are harvested. Bottles indicating contamination are discarded. A sample of pooled, clarified fluids is collected before inactivation for titration by $TCID_{50}$. Fluids with a titer of $10^{6.2}$ $TCID_{50}$/mL or greater may be used in the preparation of final product. Multiple lots can be blended to achieve the minimum titers.

Harvested lots are clarified by filtration using 5.0 micron pore-size rated polypropylene filter cartridges. Post-clarified harvest lots may be stored for up to seven days at 2-8° C. Clarified fluids are then inactivated with formaldehyde solution, USP, 0.1-0.2% by volume, transferred to a secondary container, and held at room temperature (18-26° C.) with agitation for a minimum of 48 to 72 hours. A sample of inactivated fluids is taken for inactivation assurance testing prior to concentration. Inactivated lot material is held at 2-8° C. prior to concentration. Clarified, inactivated virus fluids are concentrated by a factor of 5× to 50× using tangential flow ultra-filtration membrane cartridges with molecular weight cut-off ratings of not more than 10,000 Dalton MW.

A number of suitable adjuvants may be added to the vaccine formulation, most preferably HRA-5. Other adjuvants include HRA-3 with cottonseed oil (CSO). Typical processing steps may be employed such as mixing, blending, microfluidization, and emulsification, of the adjuvant and/or the harvested virus antigens with other ingredients.

The product is then assembled to final formulation. In a batching method in one exemplary embodiment, the required amounts of adjuvant and MEME Diluent are combined in a sterile container and the pH is adjusted to approximately 6.3-6.7 with Sodium Hydroxide. ERAV, gentamicin sulfate, formaldehyde, and Amphotericin B are added one at a time during constant mixing. The pH is adjusted to 6.8-7.0 with sodium hydroxide or hydrochloric acid and the serial is mixed for a minimum of 18 hours at 2-8° C. The completed bulk serial is then transferred to a suitable storage container and stored at 2-8° C. Amphotericin B may be added at a concentration of up to 2.5 µg/mL of the diluent volume as a preservative. Gentamicin sulfate is added at a concentration of up to 30 µg/mL of the diluent volume as a preservative Formaldehyde is added at a concentration of 0.1% of the diluent volume as a preservative. An adjuvant such as HRA-5 is added at a concentration of 10% v/v of the final serial volume.

The vaccine is given by typical hypodermic injection, with booster vaccinations if desired.

Example 2

This investigation was carried out to obtain an efficacy evaluation of a Equine Rhinitis A Virus vaccine to protect horses from challenge with Equine Rhinitis A Virus.

Materials and Methods

A high dose A-9 ($10^{7.5}$ $TCID_{50}$/mL) and low dose A-10 ($10^{7.0}$ $TCID_{50}$/mL) ERAV vaccine were prepared according to Example 1.

TABLE 1

| A-9 vaccine formulation (1 mL): | |
|---|---|
| ERAV/ON/05 | $10^{7.5}$ $TCID_{50}$/mL |
| HRA-5 | 100 µL |
| Diluent, MEM-E+ containing Gentamicin, 30 µg/mL of diluent volume and Formaldehyde, 0.1% of diluent volume | q.s. |

TABLE 2

| A-10 1 vaccine formulation (1 mL): | |
|---|---|
| ERAV/ON/05 | $10^{7.0}$ $TCID_{50}$/mL |
| HRA-5 | 100 µL |
| Diluent, MEM-E+ containing Gentamicin, 30 µg/mL of diluent volume and Formaldehyde, 0.1% of diluent volume | q.s. |

A V-05 placebo 1 mL formulation was prepared as in the A-9 and A-10 vaccines but without the ERAV/ON/05 antigen.

A total of 44 horses were randomly divided into one of three treatment groups consisting of a 15 horse V-05 placebo control group, a 14 horse A-10 low-dose group, and a 15 horse A-9 high-dose group. Horses were vaccinated with a 1 mL dose product adjuvanted with HRA-5 for three total doses, with a 21 day interval in between doses. Horses were subsequently challenged 21 days after the third vaccination by intranasal aerosolization with a $10^{7.0}$ $TCID_{50}$/mL nebulized Rhinitis A dose over a four minute period. Horses were evaluated for clinical signs of signs of temperature, nasal exudate, ocular discharge daily. Blood for serum neutralization (SN) was taken weekly.

Challenge Virus

The challenge virus was produced in tissue culture on E-Vero cells. The titer of the challenge virus was determined to be $1\times10^{6.9}$ TCID$_{50}$/mL on the day of challenge. Challenge virus was diluted on the morning of challenge 1:10 with tissue culture media to effect a titer of $1\times10^{5.9}$ TCID$_{50}$/mL.

Intranasal Challenge Method

Sedivet® (romifidine hydrochloride), a sedative and analgesic, was administered intravenously to each horse prior to challenge at a dosage of 50 µg/kg of body weight. Each horse was then challenged with approximately $10^{6.2}$ TCID50 of equine rhinitis A virus. The challenge virus was administered intranasally as an aerosol produced by a nebulizer into an Equine AeroMask (Trudell Medical International, Ontario, Canada) by the following method.

Four milliliters of $10^{5.9}$ TCID$_{50}$/mL challenge virus were placed into the nebulizer cup in the AeroMask device. A pressure hose was fitted from an air compressor to the inlet port of the nebulizer. The outlet tube was then inserted into the Aero Mask attached to the head of the horse being challenged and approximately 10 psi of air pressure was applied to the inlet port for three minutes. During this time approximately two milliliters of challenge virus fluid was aerosolized directly into the nostrils of the horse being challenged.

Serum Neutralization

A standard microtiter serum neutralization test was employed in this study. A standard microtiter serum neutralization test was employed in this study. All sera were tested in sterile flat bottom microtiter plates using five wells per dilution and an 8 well dilution series for each of the 5 test wells. Each of the 5 test wells contained 25 µl of serum dilution mixed with 25 of the indicator virus and 150 µl of a freshly planted eVero cell suspension containing approximately $5\times10^4$ cells. The test indicator virus used was either Equine Rhinitis Virus Type I. Serum neutralizing antibody titers are expressed as Reed-Muench ID$_{50}$ titers.

For performance of the test, two-fold dilutions of each test serum was made in a sterile flat bottom microtiter plate using five replicate wells per test serum and an 8 well dilution series. Dilutions were made with an adjustable volume single or multi-channel pipetting instrument using sterile microtiter tips. The volume of serum added each of 5 wells of the first row was 50 µl. All other wells contained 25 µl of DMEM (no FBS). Following serial dilution down the plate, 25 ml was discarded from the last row. 25 µl of a pre-determined dilution of the indicator virus was added to each test well. Plates were then mixed and incubated for one hour at 37° C. in 5% CO2. On conclusion of the incubation period, 150 µl of a suspension containing $4\times10^6$/mL eVero cells was added to each test and cell control well. The plates were incubated at 37° C. in a CO$_2$ incubator for 5 days, at which time plates were microscopically examined for CPE typical of equine rhinitis virus.

Nasal Exudate Evaluation

All nasal exudate observations were made prior to collection of nasopharyngeal swabs. On the Day of Challenge and for 10 days post-challenge, the nasal passages and muzzle of each of the 44 vaccinated and control horses were examined and graded using the grading and scoring description listed below.

The scoring grades of 0 through 6 were assigned on the basis of the severity of the disease indicated by each of the following classification:

TABLE 3

Scoring Grades

| Score | Description of symptoms |
|---|---|
| 0 | Essentially normal indicates the horse was clean and essentially free of nasal exudate |
| 1 | Slight clear serous discharge that may be frequently observed in both diseased and normal horses |
| 1.5 | Very slight mucopurulent discharge indicates that mucus was definitely present in small amounts in either one or both nostrils |
| 2 | Moderate clear serous discharge is indicative of a definite increase in volume over that normally observed |
| 2 | Slightly mucopurulent is a discharge easily observed in one or both nostrils |
| 3 | Copious clear serous discharge that is generally observed only in diseased horses |
| 4 | Moderately mucopurulent indicates that mucoid discharges were present in large quantities in both nostrils |
| 6 | Heavy mucopurulent indicates that copious amounts of a mucoid discharge filled both nostrils |

Ocular Evaluation

Ocular discharge was evaluated daily at the time of nasal exudate evaluation. Ocular discharge scores were recorded as 0=normal; 1=mild to moderate ocular discharge, and 2=severe ocular discharge.

Nasopharyngeal Viral Isolation

On each observation test day each nasal passage of each vaccinated and control horse was swabbed deeply by means of a sterile WECK-CEL™ surgical spear (Edward Weck and Company, Inc., Research Triangle Park, N.C. 27709) attached to an 11-inch long sterile plastic pipette. On collection, each of two surgical spears was immediately placed in a single tube containing 4 mL of chilled transport medium (E-199 supplemented with gentamicin, L-glutamine, 2× Pen/Strep, 2× Amphotericin B).

For isolation of virus, the tubes were mixed, the swabs aseptically removed, and the medium centrifuged at 1500 rpm for 10 to 15 minutes to remove particulates. Medium was filtered through a 0.2 µL syringe filter prior to inoculation on tissue culture cells. After filtration, 4-6% of sterile 85% sucrose solution was added to each sample for freezing at −80° C. in order for all samples to be tested concurrently.

For isolation of virus, the tubes were mixed, the swabs aseptically removed, and the medium centrifuged at 1500 rpm for 10 minutes to remove particulates. Medium was filtered through a 0.2 µL syringe filter prior to inoculation on tissue culture cells. One mL of the clarified transport medium was used to inoculate a 2 cm$^2$ two day old monolayer of E-Vero cells grown in a 24 well tissue culture plate from which the growth medium had been aseptically removed. Following inoculation, the inoculum was allowed to adsorb on the cell monolayer for one hour at 37° C. in a humidified incubator containing a 5% CO$_2$ atmosphere. After the adsorption period, an additional 1 mL of re-feed medium (E-199 containing 7% fetal bovine serum (FBS), 2 mM L-glutamine, Gentamicin 2× Pen-Strep and 2× Amphotericin B) was added to each well. Following addition of re-feed media the plates were then incubated at 37° C. in a CO$_2$ incubator. Each test and control tissue culture well was examined microscopically for 7 days for signs of cytopathic effect (CPE) typical of the ERAV challenge virus. Wells that were negative at the end of the 7 day observation period were subcultured onto fresh cells and observed for an additional 7 days.

Statistical Evaluation Methods

Data from all horses vaccinated with either A-9 or A-10 were combined for statistical evaluation. The influence of vaccination on the duration of disease (number of days with nasal scores>0) was evaluated using the Kruskal-Wallis and Hodges-Lehmann test (the NPAR1WAY procedure in SAS, SAS Institute, Cary N.C.). Severity of disease was evaluated by comparing the maximum disease status between the vaccinated horses and the control horses. Nasal scores were dichotomized to ≤1.5 and >1.5 based on the distribution of outcomes. The prevented fraction (PF) and 95% confidence intervals (CI) were estimated. Ocular scores were evaluated as present or absent and the prevented fraction and 95% confidence intervals were estimated (the FREQ procedure in SAS). Repeated measures analysis appropriate for continuous data was used to assess the effect of vaccination on body temperature and serum neutralization titers (the MIXED procedure in SAS). The proportion of horses which were virus positive over time and buffy coat positive over time was evaluated using Fisher's exact test at each time point (the Freq procedure). Nasal and ocular scores were assessed by Wilcoxon's rank sum test at each time point (the NPAR1WAY procedure).

Results and Conclusions

Virus Isolation from Nasal Swabs (Virus Shedding) and Buffy Coats (Viremia)

The proportion of animals which were virus positive was significantly lower in the vaccinated groups on days 2 through 7 (Table 4 below and FIG. 1) as compared to control group (P<0.05).

TABLE 4

Proportion of nasal swab virus positive over time

| Day | Control | A-9 | A-10 | A-9 + A-10 |
|---|---|---|---|---|
| 0 | 0 | 0 | 0 | 0 |
| 1 | 25 | 7.1 | 7.7 | 7.4 |
| 2 | 100 | 20* | 23.1* | 21.4* |
| 3 | 100 | 46.7* | 57.1* | 51.7* |
| 4 | 100 | 60* | 57.1* | 58.6* |
| 5 | 93.3 | 53.3* | 35.7* | 44.8* |
| 6 | 60 | 40 | 0* | 20.7* |
| 7 | 100 | 46.7* | 78.6 | 62.1* |
| 8 | 26.7 | 13.3 | 0 | 13.8 |
| 9 | 0 | 6.7 | 0 | 3.5 |
| 10 | 0 | 6.7 | 0 | 3.5 |
| 11 | 0 | 0 | 0 | 0 |
| 12 | 0 | 0 | 0 | 0 |
| 13 | 0 | 0 | 0 | 0 |
| 14 | 0 | 0 | 0 | 0 |

(*P < 0.05 versus control, Fisher's Exact test on each day)

Figure 2:
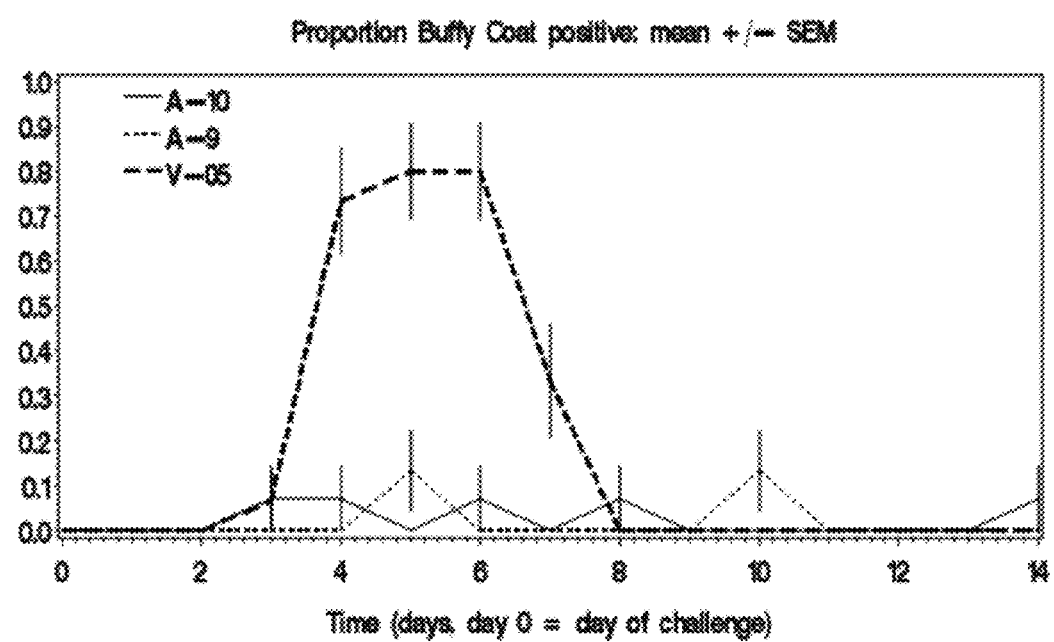
FIG. 2 is a graphical representation of the proportion of buffy coat positive across time.

Buffy coat positive animals were less frequent in the vaccinated group on days 4-7 as compared to the control group (Table 5 below and FIG. 2).

TABLE 5

Proportion of Buffy Coat positive over time

| Day | Control | A-9 | A-10 | A-9 + A-10 |
|---|---|---|---|---|
| 0 | 0 | 0 | 0 | 0 |
| 1 | 0 | 0 | 0 | 0 |
| 2 | 0 | 0 | 0 | 0 |
| 3 | 6.7 | 0 | 7.1 | 3.5 |
| 4 | 73.3 | 0* | 7.1* | 3.5* |
| 5 | 80 | 13.3* | 0* | 6.9* |
| 6 | 80 | 0* | 7.1* | 3.5* |
| 7 | 33.3 | 0* | 0* | 0* |
| 8 | 0 | 0 | 7.1 | 3.5 |
| 9 | 0 | 0 | 0 | 0 |
| 10 | 0 | 13.3 | 0 | 0 |
| 11 | 0 | 0 | 0 | 0 |
| 12 | 0 | 0 | 0 | 0 |

TABLE 5-continued

Proportion of Buffy Coat positive over time

| Day | Control | A-9 | A-10 | A-9 + A-10 |
|---|---|---|---|---|
| 13 | 0 | 0 | 0 | 0 |
| 14 | 0 | 0 | 7.1 | 3.5 |

(*P < 0.05 versus control, Fisher's Exact test on each day)

Serum Neutralization

TABLE 6

Summary of body temperature and serum neutralization

| | P-Values | | |
|---|---|---|---|
| Variable | Vaccine | Day | Vaccine * Day |
| Temperature | 0.9269 | <0.0001 | 0.0255 |
| SN titer (ln transformed) | <0.0001 | <0.0001 | <0.0001 |

Figure 3:
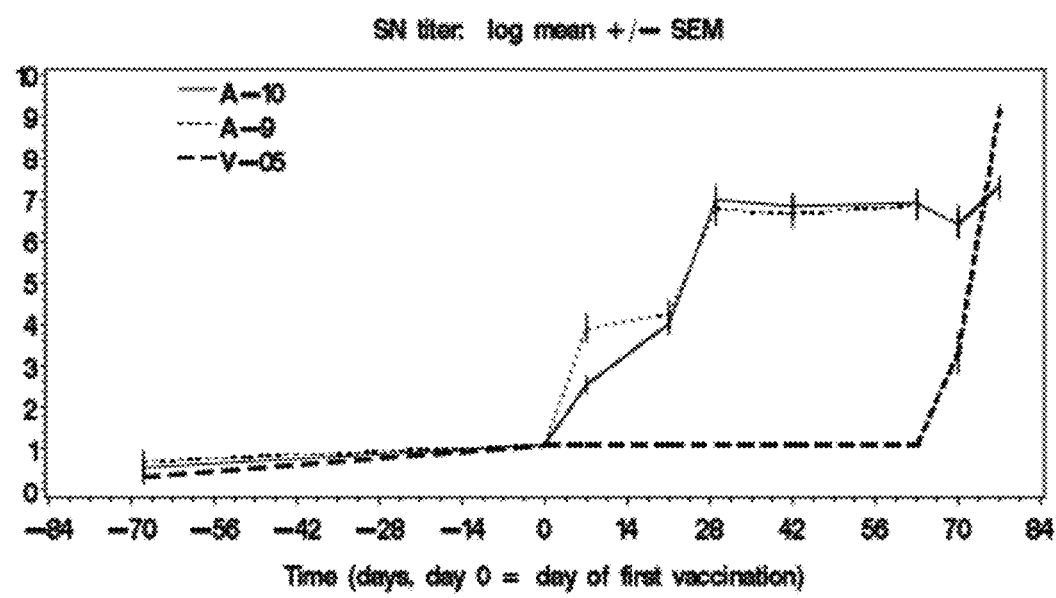
FIG. 3 is a graphical representation of the serum neutralization titers across time.

Mean body temperature values (rectal temperature measured with calibrated GSA Electronics thermometer probe) on each challenge day were always within normal body temperature parameters. Large increases in SN titers resulting from vaccination were found (see also FIG. 3) following challenge.

Nasal And Ocular Evaluation

Mean ranks for nasal scores were lower on days 4 though 10 and days 12-13 in the vaccinated group compared to the control group (Table 7 below and FIG. 4). The mean ranks for ocular scores were lower on day 7 in the vaccinated group as compared to the control group (see also FIG. 5).

TABLE 7

Mean rank for nasal and ocular score across time

| | Ocular Score | | Nasal Score | |
|---|---|---|---|---|
| Day | Control | A-9 + A-10 | Control | A-9 + A-10 |
| 0 | 22.5 | 22.5 | 22.5 | 22.5 |
| 1 | 22.5 | 22.5 | 22.5 | 22.5 |
| 2 | 22.5 | 22.5 | 23.9 | 21.8 |
| 3 | 22.5 | 22.5 | 26.2 | 20.6 |
| 4 | 22.5 | 22.5 | 27.7 | 19.8* |
| 5 | 21.8 | 23.9 | 20.2 | 19.5* |
| 6 | 22.5 | 22.5 | 28.5 | 19.4* |
| 7 | 29.2 | 19.0* | 29.2 | 19.0* |
| 8 | 21.8 | 23.9 | 30.1 | 18.5* |
| 9 | 21.5 | 24.4 | 27.4 | 19.9* |
| 10 | 22.5 | 22.5 | 28.1 | 19.6* |
| 11 | 22.5 | 22.5 | 37.2 | 20.1 |
| 12 | 21.5 | 24.4 | 30.7 | 18.3* |
| 13 | 22.0 | 23.5 | 28.8 | 19.2* |
| 14 | 22.5 | 22.5 | 25.6 | 20.9 |

(*P < 0.05 versus control; Wilcoxon's rank sum test on each day, A-9 and A-10 combined)

Disease Duration: Nasal Exudate Evaluation

TABLE 8

Summary of the effect of vaccination on the duration of disease (Number of days with nasal score >0)

| Group | Minimum | 25th quantile | 50th quantile | 75th quantile | Maximum |
|---|---|---|---|---|---|
| Control | 8 | 9 | 10 | 11 | 13 |
| Vaccinated | 0 | 1 | 3 | 9 | 13 |

TABLE 9

Effect of vaccination on the duration of disease

| | Control | Vaccinate | Shift in days | 95% confidence interval |
|---|---|---|---|---|
| Duration | 10 | 3 | 7* | 3, 8 days |

(nasal scores; *significantly lower than control group by Kruskal-Wallis test $P < 0.05$)

Figure 4:
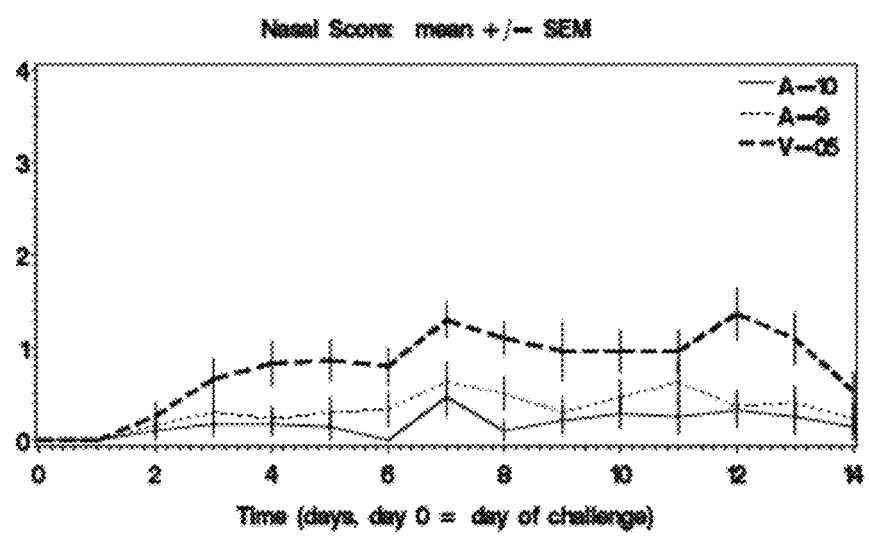
FIG. 4 is a graphical representation of the mean nasal scores across time.

Long duration of nasal discharge in controls was found following challenge (Table 8, see also FIG. 4). Vaccinated group showed a significant reduction in duration of nasal discharge. Controls experienced a minimum of 8 days of nasal discharge vs 11 vaccinates (38%) with 1 day or less. Two thirds of vaccinates had shorter duration of nasal discharge than the minimum of 8 days in the control group. Duration was from first to last abnormal observation, even if horse had normal days in between. The number of days animals were sick with clinical signs of respiratory disease (nasal score>0) was significantly shorter (shift of 7 days) in the vaccinated group compared to the control group.

TABLE 10

Maximum Nasal Scores - Significant difference between the two distributions of scores (Kruskal-Wallis test, P = 0.0157).

| | Maximum Nasal Score | | | | | |
|---|---|---|---|---|---|---|
| Group | 0 | 1 | 1.5 | 2 | 3 | 4 |
| Control | 0 | 0 | 5 (33%) | 9 (60%) | 0 | 1 (7%) |
| Vaccinated | 4 (14%) | 2 (7%) | 13 (45%) | 10 (34%) | 0 | 0 |

TABLE 11

Nasal scores (≤1.5 and >1.5)

| Group | % with score | P-value | Prevented Fraction | 95% confidence interval |
|---|---|---|---|---|
| Control | 66.7% | <0.0588 | 0.48 | 0.042 |
| Vaccinate | 34.5% | | | 0.72 |

Vaccination also reduced severity of nasal discharge (maximum score on any day post-challenge). Maximum nasal scores were compared between groups (Table 10). The minimum nasal score for horses in the control group was 1.5. Results were thus dichotomized to scores ≤1.5 and >1.5 for the evaluation of disease severity (Table 11). The prevented fraction was 48% with a lower confidence limit greater than 0. The overall distribution of maximum nasal scores was significantly reduced by vaccination (Kruskal-Wallis test, P=0.0157).

Ocular Evaluation

TABLE 12

Ocular scores (present or absent)

| Group | % with score | P-value | Prevented Fraction | 95% confidence interval |
|---|---|---|---|---|
| Control | 66.7% | <0.0001 | 0.897 | 0.587 |
| Vaccinate | 6.9% | | | 0.9741 |

Figure 5:
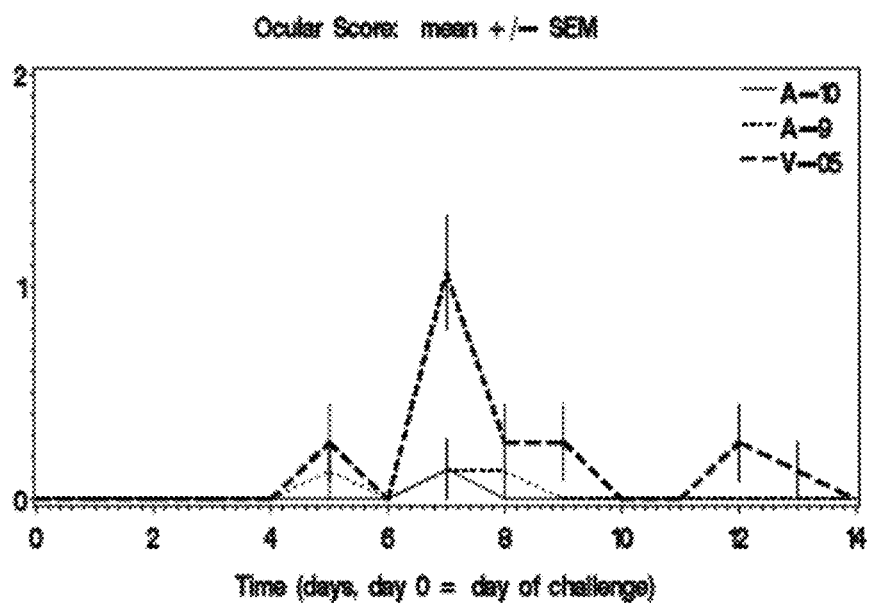
FIG. 5 is a graphical representation of the mean ocular scores across time.

Since only two values were reported for ocular scores (0 or 2), results were dichotomized to present or absent within an individual. The prevented fraction was then used to evaluate the effect of vaccination on the presence of ocular signs. The vaccine significantly reduced the severity of ocular discharge resulting from infection with ERAV. Mean ocular scores over time are also shown in FIG. 5.

Data from this study demonstrate that administration of intramuscular doses of the inactivated virus is capable of immunizing an animal to high levels of antibody detection which prevent ocular disease and reduce severity and duration of nasal discharge. Vaccine was highly effective in preventing any ocular discharge following ERAV challenge. Nasal discharge persisted for a relatively long period post-challenge, while ocular discharge peaked and abated quickly. Hence the vaccine showed a significant improvement in nasal discharge for a prolonged period (9 of 10 consecutive days), whereas vaccine significantly reduced ocular discharge for 1 day during which ocular signs were most severe. In addition, vaccination significantly reduced nasal virus shedding throughout the successive six days of peak viral shedding, and viremia also was significantly reduced during the four day of peak viremia within the challenge period.

No unacceptable adverse reactions either at the injection sites or by manifestation of signs of systemic illness were observed. The vaccine is safe and well tolerated for administration in Equine rhinitis A susceptible species, particularly equidae. This study thus demonstrates that 3×1 mL intramuscular injections of the ERAV compositions of the example significantly reduced severity and duration of respiratory disease caused by ERAV virulent challenge.

Example 3

This example illustrates sequencing and analytical studies carried out on an Equine Rhinitis A Virus strain as disclosed herein.

Cells And Virus

Rabbit-kidney-13 (RK-13) cells (passages 100-160) were grown in Dulbbeco's modified eagles medium nutrient mixture F12 HAM (DMEM F12) (Sigma-Aldrich Canada Ltd. Oakville, Ontario) with 2-5% fetal bovine serum (FBS) (Sigma). Cell growth and viral propagation were performed in a $CO_2$ (5%) incubator at 37° C. The ERAV isolate ERAV/ON/05 was propagated in RK-13 cells and aliquots were stored at −70° C. for later work. RK-13 monolayers were inoculated at 90% confluence and RNA was extracted before cytopathic effects (CPE) was observed.

Virus Titration And Plaque Purification

RK-13 cells were grown on 3 cm round dishes, using DMEM F12 with 2% fetal calf serum. Cells were infected at 90% confluence and plates were incubated at 37° C. for 72 hours. After 24 hours, the medium was replaced and a 0.7% agarose layer was added. Plaques were counted and recorded every 24 hours. At 72 hours the agarose layer was removed and plaques were stained with crystal violet and counted.

For plaque purification RK-13 cells were infected with ERAV/ON/05, adsorption was allowed for 45 minutes and the inoculum was removed and replaced with a 0.7% agarose layer. Plates were checked every 12 hours and plaques were classified as small, medium and large. Five plaques of each size were selected, picked into 300 μL of DMEM F12, and frozen at −70° C. Viruses from each plaque size were propagated in RK-13 cells and RNA was extracted from the small and large plaques for genome sequencing of the 5' UTR.

Viral Growth Kinetics

To study the growth characteristics of this strain, RK-13 cells were infected with ERAV/ON/05 and supernatant samples were collected at various times for titration. RK-13 cells were grown on 3 cm individual round plates and infected at 90% confluence. Plates were incubated at 37° C. and supernatant samples were taken every 4 hours starting at 0 hours for a period of 28 hours. All samples were titrated using the plaque forming unit (PFU) technique as previously described here.

Immunofluorescence

RK-13 cells were grown on glass tissue culture chamber/slides (Miles Scientific, Inc., Naperville, Ill.), and inoculated with ERAV/ON/05. Twenty eight hours post-infection, the cell culture medium was removed and cells were fixed in acetone. The slides were kept at 4° C. until processing. Sera from experimentally infected horses were used as a source of ERAV antibodies.

Rna Extraction And Sequencing

RNA was extracted from infected cell monolayers. Cells were treated with 1 mL of TRIzol (Invitrogen) 18-20 hours post-infection and extraction was performed according to manufacture's recommendations. RNA pellets were eluted in 30 μL of RNAse free water and kept at −70° C. for later use. First strand cDNA was synthesized using superscript 11 (Invitrogen) following manufacturer's recommendations. A 50 μL PCR reaction was carried out using a set of sense and antisense primers. For genome sequencing, the primer walking approach was used, and primers were designed based on eight ERAV sequences available on GenBank. PCR conditions were: 4 minutes at 94° C., followed by 30 cycles of 30 seconds at 94° C., 30 seconds at 55° C. and 30 seconds at 72° C. with a final extension at 72° C. for 10 minutes.

Sequencing of the 5' and 3' ends were completed with the 5' RACE and 3' RACE kits (Invitrogen) as recommended by the manufacturer. Several nested PCRs were required to amplify the 5' UTR end.

Sequence Analysis

The preliminary identification of the virus was completed by partial sequencing of the structural protein VP1 using primers designed based on other sequences available on GenBank.

TABLE 13

Primers used to amplify some of the ERAV regions.

| NAME | PRIMER SEQUENCE | SEQ ID NO: | GENOMIC SITE |
|---|---|---|---|
| forwVP1 last | 5' tgaatagcaagggccgtgtt 3' | 4 | 3087 |
| revVP1 last | 5' accgttgtaaaagactggcaca 3' | 5 | 3671 |
| forwPC112 | 5' gtcagtaaaacgcaacaaccat 3' | 6 | 112 |
| forwPC805 | 5' tgtgaagaatgtcctgaaggca 3' | 7 | 805 |
| revPC1749 | 5' accatccacctaaaccagacga 3' | 8 | 1749 |
| forwPC5217 | 5' attggctttgtcaggtgttgaa 3' | 9 | 5217 |
| revPC5952 | 5' gtttctaactttgggacccgaa 3' | 10 | 5952 |
| forwPC6915 | 5' tggatttgagattggttctgca 3' | 11 | 6915 |
| revPC7511 | 5' gcgaacgaaactgaggattg 3' | 12 | 7511 |

All primers were designed on Gene Runner version 3.05 (Hastings Software Inc.). Sequencing reactions were set and run by the Laboratory Services Division at the University of Guelph.

All sequences were assembled and edited with EditSeq and SeqMan DNASTAR Lasergene 8 (DNASTAR Inc., Madison, Wis., USA). Sequencing results were entered into the BLAST software [National Center for Biotechnology Information, Bethesda, Md. (NCBI)] and compared to similar entries on GenBank. ClustalW2 [European Bioinformatics institute, Dublin, Ireland (EBI)] was used for multiple sequence alignment and preliminary construction of the phylogenetic tree. The final phylogenetic tree was created on MEGA 4.0 by using the Maximum Composite Likelihood method and the reliability was evaluated by bootstrapping with 1000 replications. Analysis of the nucleotide sequences were plotted on SimPlot Version 3.5.1 (Baltimore, Md., USA). In order to investigate the possibility of viral recombination between ERAV isolates, we completed a Bootscan analysis on SimPlot (Version 3.5.1) comparing the genomic sequences of all reported ERAV available on GenBank. Polyprotein cleavage sites were predicted based on sequences reported on GenBank with accession numbers: DQ272578 and NC003982.

Results

Initial Characterization

The viral protein (VP1) of the virus was amplified, partially sequenced and compared to sequences available on GenBank (accession numbers: NC003982, DQ272577, DQ272128, DQ272127, DQ268580, DQ272578, L43052). Results from this initial comparison demonstrated a maximum identity of 95% to Equine rhinitis A virus VP1.

Virus Titration

The ERAV isolate was initially propagated in cell culture and titrated by the plaque forming unit method. The stock virus titre obtained was $5\times10^7$ PFU on the initial titration. Subsequent experiments showed no dramatic changes in viral titre after 3 years of initial freezing. For animal experiments the stock virus with the initial titre was employed.

Growth Kinetics

All supernatant samples were titrated using the PFU technique and results were entered on a spread sheet to construct a growth curve. As seen in other picornaviruses, the Ontario isolate showed an increased titre at 4 hours post-infection, reaching a plateau by 12 hours post-infection.

Immunofluorescence

Infected RK-13 cells were visualised under the immunofluorescence microscope. Bright green fluorescence signals were detected in the cytoplasm of ERAV infected cells compared to negative signals on mock infected cells.

Plaque Purification

Sequencing of a 426 nucleotide fragment in the 5' UTR on the small and large plaques showed no difference between plaque sizes at the nucleotide level. However, morphological characteristics were evidently different on RK-13 cell cultures.

Full Genome Sequencing

Genome sequencing of the ERAV isolate resulted in 7839 nucleotides in length with a GC content of 47% including the poly (A) tail. Four identical repeats (CTGTAGCGTCAGTAAAACGC SEQ ID NO: 13) separated by 18, 21 and 18 nucleotides were identified on the 5' UTR. The ERAV 5' UTR was composed of 940 nucleotide with a 54% GC content. A single polyprotein with 6747 nucleotides (2248 amino acids) composes the viral genome with a 46.8% GC content. The protein starting synthesis was detected on nucleotide 940 with the AUG start codon and the ending on nucleotide 7686 with the UAA stop codon. Of great interest, a second AUG sequence was identified following the initiation codon. A subsequent AUGAUG sequence was also identified 58-nucleotides downstream from the polyprotein start codon. Analysis with Blastx (NCBI) of the polyprotein on this isolate showed a 96% nucleotide identity with respect to other ERAV reported, however when the full-length genome sequence of the Ontario isolate was aligned and compared to others using ClustalW2 (EBI) and Blastx (NCBI), only a maximum identity of 80% was observed. The amino acid composition showed an identical protein (structural and non structural) organization and length along the entire genome. These comparisons were made with PERV-1 and PERV reported genome sequences (accession numbers DQ272578, and NC003982).

The 3' UTR was composed of 110-nucleotides with a 24.3% GC content, and a poly-A tail. Alignments of the 5' UTR of all ERAV available demonstrated a lower identity percentage, ranging from 73% to 81%. Similarly, the 3' UTR was analysed by the same method and the identity percentage ranged from 75% to 81%. Interestingly, various insertions (1-nucleotide, 2-nucleotides, and 13-nucleotides) and two small deletions (2-nucleotides, and 3-nucleotides) in the 5' UTR were identified (FIG. 4). No other major changes were observed throughout the entire genome.

Simplot Genome Analysis

SimPlot analysis showed a comparable similarity (percentage) among all ERAV isolates when compared to ERAV/ON/05. However, the mayor disparities were identified at nucleotide 1500 (59% similarity) and nucleotide 4700 (65% similarity). Nevertheless, this analysis showed that the similarity along the genome was between 70% and 82%. To further investigate the major divergence in the genomes, a scan (Bootscan) to identify possible recombination sites was performed. These analyses demonstrated that the Ontario isolate has not had predicted recombination sites with other ERAV isolates. Nevertheless, when the Ontario isolate was removed from the analysis, possible recombination between other ERAV isolates may have happened in the pass.

Discussion

ERAV is not routinely sought and recovered from clinical cases during equine respiratory outbreaks. Therefore ERAV isolation from clinical cases has been incidental and in most cases a challenge. For these reasons the recovery and sequencing rate of these viruses may be small.

During previous years, equine rhinitis viruses were classified within the Picornaviridae family, but were not clearly assigned to a specific genus. In 1996 Li and coworkers (Li F, Browning G F, Studdert M J, and Crabb B S. Equine rhinovirus 1 is more closely related to foot-and-mouth disease virus than to other picornaviruses. Proc Natl Acad Sci USA. 1996 6; 93:990-995) demonstrated that ERAV was closely related to foot and mouth disease virus (FMDV) based on the phylogenetic characteristics and nucleotide sequencing. In agreement with their findings and others (Wutz G, Auer H, Nowotny N, Grosse B, Skern T and Kuechler E. Equine rhinovirus serotypes 1 and 2: relationship to each other and to aphthoviruses and cardioviruses. J Gen Virol 1996, 77:1719-1730) the ERAV isolate has been found to be closely related to isolates L43052, DQ272578, and NC003982.

The ERAV/ON/05 isolate resulted in 7839 nucleotides including the 5' UTR, the polyprotein, 3' UTR and the poly-A tail. In comparison to previously reported ERAV isolates, the ERAV/ON/05 is one of the most complete ERAV sequences reported to date. Most of the other sequences lack some information either from the 5' UTR or are partial sequences of individual viral proteins. Data from the 5' UTR revealed the presence of 3 repeats that have been previously reported in other ERAV and commonly found on the FMDV. It has been suggested that these repeats may be required in the formation of the secondary structures found in the 5' UTR, the internal ribosome entry site (IRES). The identity analysis showed that the ERAV/ON/05 isolate's polyprotein bears a highly conserved nucleotide sequence. As an RNA virus, the ERAV is prone to constant mutations due to the lack of proofreading by the polymerase. This may indicate, that even though this RNA virus has been under natural evolution and constant replication no significant genomic changes have been introduced since its first genomic sequence was reported. It is evident that the structural and non structural proteins, which are encoded within the polyprotein, represent the most conserved regions in the genome.

Interestingly, the viral replication rate in cell culture was rapid and efficient. A complete viral replication cycle was detected in less than 4 hours, reaching a plateau in 12 hours. These characteristics are typical of picornaviruses and may reflect the viral activity in vivo. Such features might explain the severity and speed of clinical signs in some equine respiratory viral infections. As observed in other viruses, such as poliovirus and FMDV, the presence of small deletions and/or insertions in the 5'UTR have been associated with differences in plaque size in cell culture, and excel virulence in vivo. We found that the ERAV/ON/05 isolate generates different plaque sizes when infecting RK-13 cells. To investigate and correlate the presence of these insertions and deletions in the 5' UTR in the ERAV/ON/05 isolate, we sequenced this region from plaque purified viruses from different plaque sizes, and found no discrepancy at the nucleotide level. This finding may indicate that the plaque size difference may be due to a growth and replication characteristic of the RK-13 cells and perhaps not associated with the presence or absence of the sequences we found in this region.

Example 4

This example shows results of a study designed to develop a reliable ERAV infection model for investigating the clinical characteristics of ERAV/ON/05.

Materials and Methods

On the first phase a pony foal was infected with ERAV/ON/05 to adjust the infectious dose and sampling collection techniques. A second pilot study was designed to compare infected and control animals, and to master sampling techniques. The main infection study was conducted in two phases due to animal handling and time sampling constraints. One year after the first infection, four previously infected ponies were selected for a re-infection study based on their titre to ERAV. Animals with an intermediate and a high titre to ERAV were selected to be re-exposed to the Ontario isolate.

Experimental Animals

A total of 12 pregnant pony mares were selected and their foals were kept for the experimental ERAV infection. All mares and foals were kept in a separate group away from the main barn and biosecurity measurements were put into place to prevent viral respiratory infection. Blood samples from all foals were taken regularly and titers to ERAV were checked periodically. Foals were kept until they reached 12 months of age. These animals were not vaccinated against any respiratory viruses during this period and general practices were maintained to ensure healthy living conditions. All animals were de-wormed according to the herd management protocol. Animal socialization and handling was performed regularly. Ponies were trained for pulmonary function test (PFT). Once the animals were conditioned for the experiments, they were transported in groups to the isolation unit and acclimatized for at least one week prior to the viral infection.

Isolation Unit

All infection trials were conducted at the animal isolation unit in the Department of Pathobiology, at the University of Guelph. This isolation unit contains individual stalls that are equipped with controlled temperature, humidity, airflow, and lighting. Access to the stalls was restricted to the researchers and care personnel.

Selection Criteria

All foals were handled frequently, and health status was checked periodically. Based on health status and serological parameters, animals to be included in these experiments were chosen. At that time, all ponies remained seronegative to equine rhinitis A virus (ERAV), equine rhinitis B virus (ERBV), equine herpesvirus 1 and 4 (EHV1/4), and equine influenza 2 virus (AE2). Even thought AE2 antibody titers were detected at birth, a steady decreased was observed during the first 5 months and were not detectable by the single radial haemolysis test (SRH) at six months of age. For the ERAV experimental infection trial, one pony was selected to be used. Subsequently, two other ponies were selected for a second pilot study, and a group of 8 ponies (four infected and four controls) were selected for the main infection study. After a year from the first infection trial, 4 ponies with intermediate and high titers to ERAV were chosen for a re-infection trial.

Inoculum

ERAV isolate (ERAV/ON/05) recovered from a horse during an equine viral respiratory outbreak in Ontario 2005 was propagated in rabbit kidney-13 cells (RK-13) and aliquots were stored at $-70°$ C. for viral characterization and animal viral infection experiments.

Briefly, for inoculum preparation, the isolate was propagated in RK-13 cells. 30 mL round dishes containing 90% confluent monolayers were infected with 500 μL of ERAV/ON/05 and incubated in the presence of $CO_2$ (5%) at $37°$ C. for 24-36 hours. All dishes were removed from the incubator and freeze/thawed four times to provoke cell rupture and viral release from intact cells. Supernatants from all dishes were pooled into one flask and centrifuged at 6000 RPMS for 15 minutes to clarify and discard cell debris. The clarified supernatant was aliquotted in 10 mL vials to be used as an inoculum in the animal viral infection experiments. Additionally, small 1 mL-aliquots were separated and kept for viral titration. The virus was titrated using the plaque forming unit method (PFU).

Animal Model

Ponies were chosen as an animal model due to the nature of the experimental agent (ERAV), animal size, availability and handling.

Infection Protocol

Ponies between 8 and 12 months of age were selected, trained and used in the infection experiments. Due to the large number of samples to be taken, these experiments were divided in five sections (two pilot studies, two main infection experiments, and one re-infection experiment). During the pilot studies, equipment, animal handling, inoculum dose, route of administration, and sample collection were optimized. The re-infection study was conducted one year after the initial infection trial. Ponies in the re-infected group were exposed to the same viral strain at the same dose used during the first infection. Only clinical examination, blood sampling for titers assessment and nasopharyngeal swabs for virus isolation were collected from this group.

Face Mask and Nebulization

For viral infection, a small size Equine AeroMask™ was fitted with a rubber seal on the nostril ending. Size was adjusted depending on the pony's head and the breathing windows were not modified. The mask was fitted with an inhaler connector and a one way "T" valve for virus nebulization. Conventional 6 mL nebulizer cups were employed to deliver the inoculum. Nebulization was performed using a PM14 compressor (Precision Medical Inc. Northampton, Pa.) with a gas flow of 9 LPM (liters per minute). This flow rate and delivery cups allow for consistent delivery of breathable particles of more or less 5 microns. Each pony was nebulized for 45 min (taking a 5 minute break every 15 minutes) with 15 mL (total volume) of either inoculum or placebo. A nasopharyngeal swab per pony was collected post-infection to ensure viability of the inoculum when delivered. Ponies that were re-infected a year latter were exposed to the virus by the same protocol.

Clinical Examination

All ponies were clinically evaluated on a regular basis from birth. Prior to the pilot and infection studies, all ponies were evaluated daily and during trial experiments twice daily for the first 10 days and once daily from day 11 up to day 21 post-infection. Clinical examination included: Body temperature (temp) (Celsius degrees), heart rate (hr), respiratory rate (a), capillary refill (ref), gastrointestinal motility (gi), lung sounds (ls), nasal discharge (nd), ocular discharge (od) [presence or absence and characteristics], lymph nodes (ln) [size and characteristics], ambulation, and general physical condition. Physical examination was performed at around the same times on each pony every day, commencing with the control animals and moving onto the infected group. Approximately 10 minutes were spent on each animal examination every time and all individual data were recorded on a daily check up form.

Pulmonary Function Test (PFT)

The PFT was carried out as previously described by Hare and coworkers (Hare J E, Viel L. Pulmonary eosinophilia associated with increased airway responsiveness in young racing horses. *J Vet Intern Med* 1998; 12(3):163-70). The test was performed on all control and infected ponies prior to infection (day 0) and on days 1, 7, 14, and 21 post-infection. Briefly, on testing day, ponies were off feed in the morning and were mildly sedated as previously described here for endoscopy procedures. A rubber face mask was fashioned to snugly fit the ponies' muzzle. A pneumotachograp #4 (Gould Electronics, Biltholven, The Netherlands) was attached to the face mask, and connected to a set of transducers that convert the flow and pressure signals into breath loops that are recorded on a computer (Pulmonary Mechanics Analyzer, Buxco Electronics Inc, Sharon, Conn., USA). Flow was measure at the pneumotachograp level and the pleural pressure was assessed by an esophageal balloon (10 cm long) that was placed in the mid thorax via esophageal tubing. A total volume of 3 ml of air were introduced into the balloon. The pressure difference between the pleural pressure and the atmospheric pressure (measured at the nostril level) was considered as the transpulmonary pressure ($\Delta$Ppl).

Bronchoprovocation Testing

Bronchoprovocation challenge was carried out as part of the PFT testing. To determine the hyperresponsiveness of the airways post ERAV/ON/05 infection, control and infected animals were exposed to increasing histamine doses (doubling dose) by nebulization with a PM14 compressor with a gas flow of 9 LPM (Precision Medical Inc. Northampton, Pa.). Pulmonary physiological parameters were assessed initially by administering 0.9% physiological saline solution (base line), followed by increased histamine doses. After each administration (2 minutes) data was recorded for 3 minutes and respiratory physiology was later analyzed. Histamine doses were started at 0.5 mg/ml and were increased gradually to a maximum of 32 mg/ml. Dynamic compliance ($C_{dyn}$) and $\Delta$Ppl were used as parameters to discontinue histamine nebulization. When $C_{dyn}$ was decreased by two thirds or $\Delta$Ppl was doubled during histamine administration, nebulization was suspended. Histamine triggering dose was later plotted and calculated. All ponies were mildly sedated and physically restrained during these procedures.

Sampling Techniques
Blood Collection

Blood samples were collected from either the right or left jugular vein. Approximately 10 ml of blood were collected on a red top tube (serum) from each pony according to the sample collection schedule. Additionally, 3 to 5 ml of blood were also collected for CBC (complete blood count) and profile. All samples were collected in the morning hours and processed within the same day.

Blood samples for serum separation were kept at room temperature for at least 30 minutes and then centrifuged at 3000 rpm on a table centrifuge. Serum was separated within 6 hours from the collection time and aliquots were labelled and frozen at −70° C. for later analysis (antibodies to ERAV, ERBV, AE2, and EHV1/4). Blood samples for CBC and profile were processed within the same day.

Nasopharyngeal Swabbing

Nasopharyngeal swabs were collected for virus isolation on days previous to the infection trial and on days 0, 1, 3, 5, 7, 10, 12, 14, 17 and 21. Each pony was restrained with a muzzle twitch and a 30 cm long swab (Kalayjian Industries, Inc. Signal Hill, Calif.) was passed into either the right or left nostril until it reached the pharynx. Swabbing was performed by rotating the swab for about 5 to 10 seconds. The swab was removed carefully, and the tips were cut off into a vial containing 3 ml of virus transport medium (VTM). The vials containing the swabs were shaken and kept on ice until processing. To release the viral particles and cells attached to the swabs, vials were vortexed for about 20 seconds and the medium was transfer to a 1.5 mL Eppendorf tube and frozen at −70° C. for later analysis.

Urine and Fecal Sampling

Virus isolation was attempted on urine and fecal samples pre and post-infection with ERAV/ON/05. Urine was collected in the morning after clinical examination and/or stall cleaning by holding a collection cup while the animals were urinating. When the sample could not be collected by hand, the animal was fitted with a plastic collection bag around the genitals. This bag was removed after the animal urinated and a 10 mL aliquot was saved for virus isolation. Fecal samples were hand collected from fresh manure on the stall's floor. About 5 mL of manure were collected into a collection cup and 10 mL of sterile saline were added to dissolve the sample. Urine and fecal samples were kept on ice until processed.

Upper and Lower Endoscopy

Bronchoscopy and BAL were performed as previously described (Hare et al., 1998). A sterile flexible fiberoptic endoscope, 140 cm length with a 0.8 mm OD (Olympus, Corp., Tokyo, Japan) was advance through the right or left nostril into the nasal cavity to the larynx level. At this point the upper airways conformation was evaluated. Followed, the bronchoscope was advance into the trachea and the presence or absence of inflammation and/or mucus and its characteristics were recorded. Data were recorded on the daily evaluation sheet and all the endoscopies were video recorded for later analysis.

Pharyngeal and Tracheal Brush Biopsies

In order to assess viral replication in the upper and lower airways, a brush biopsy was taken from the pharynx, mid trachea, and the carina of infected and control animals on days 0, 1, 3, 5, 7, 10, 14, and 21. During endoscopy examination, a 200 cm guarded (protective sleeve) cytology brush (Hobbs Medical Inc. Connecticut) was advance through the biopsy channel at the predetermined sample location and a sample was collected. Brushes were retracted into the protective sleeve and removed from the bronchoscope. To remove the sampled tissue from the brush, this was put into 600 µL of VTM and vortexed for 10 to 20 seconds. All samples were kept on ice and transported to the laboratory for further analysis (virus isolation).

Bronchoalveolar Lavage (BAL)

Briefly, all ponies were mildly sedated with Romifidine (0.04 mg/kg, IV) and a sterile 0.8 mm OD bronchoscope (Olympus, Corp., Tokyo, Japan) was advance through the right or left nostril into the trachea to the carina level. As the bronchoscope was advanced, a 0.2% warmed lidocaine solution was administered to reduce cough and distress. Once the cough reflex was reduced the bronchoscope was advanced and wedged into a proximal terminal bronchus. A total of 250 mL of warmed sterile saline solution was administered through the biopsy channel divided in two aliquots. BAL fluid was retrieved by manual suction with a 60 cc syringe through the biopsy channel and placed on ice. The fluid was filtered and aliquots for virus isolation, cell count, and cytospin slides were made.

Clinical Samples Culturing

Collected samples were transported on ice and frozen at −70° C. for later inoculation on cell cultures.

RK-13 cells (passages 100-160) were grown in Dulbbeco's modified eagles medium nutrient mixture F12 HAM (DMEM F12) (Sigma-Aldrich Canada Ltd. Oakville, Ontario) with 2-5% fetal calf serum (Sigma). Cell growth and isolation were performed in a $CO_2$ (5%) incubator at 37° C. RK-13 cells monolayers were grown on 6 well plates to a 90% confluence and infected with the clinical samples collected from the infection trial. In brief, 90% of the growing medium was removed from each of the wells and 200 µL of the specimen to be tested were added to the monolayer. Plates were put on the rocker platform for one hour and 3 mL of medium were added after the time elapsed. Plates were incubated and checked every 24 hours for cytopathogenic effects (CPE). If CPE was detected, the supernatant was removed from the well and frozen for later analysis. Results from the virus isolation test were recorded on a spread sheet. Plates were checked for up to 7 days and if CPE was not developed, a second passage was attempted using 200 µL of supernatant from the first passage. After a second passage if CPE was not detected the sample was classified as negative. Supernatant from positive and negative samples was saved to be confirmed by reverse transcriptase polymerase chain reaction RT-PCR).

Statistical Analysis

Results from virus isolation and all clinical scores (Table 7) were entered on a spread sheet.

TABLE 14

Scoring system for experimental infection with ERAV/ON05.

| Clinical sign | Degree | Score |
|---|---|---|
| Cough | None | 0 |
| | Intermittent | 1 |
| | Frequent | 2 |
| Mucus membranes | Pink | 0 |
| | Pale | 1 |
| Gastro intestinal auscultation | Normal | 0 |
| | Abnormal | 1 |
| Feces/Urine | Normal | 0 |
| | Abnormal | 1 |
| Lung Sounds | Normal | 0 |
| | Slightly Increased | 1 |
| | Marked Increased throughout chest | 2 |
| | Crackles and wheezes | 3 |
| Nasal Discharge | None | 0 |
| | Moderate/severe serous | 1 |
| | Mucopurulent | 2 |

TABLE 14-continued

Scoring system for experimental infection with ERAV/ON05.

| Clinical sign | Degree | Score |
|---|---|---|
| Ocular Discharge | None | 0 |
| | Serous | 1 |
| | purulent | 2 |
| Adenitis | not palpable | 0 |
| | palpable (<1 cm) | 1 |
| | Enlarged (>1 cm) | 2 |
| Anorexia | None | 0 |
| | Mild to Moderate | 1 |
| | Severe | 2 |
| Temperament | Bright, alert and responsive | 0 |
| | Dull (head down, disinterested) | 1 |
| Perfusion Time | Normal (2 s) | 0 |
| | 3-4 s | 1 |
| | 5 s | 2 |

Virus isolation results were categorized as positive or negative and results were compared between groups. To determine if there was a statistical difference between locations on virus isolation (in the infected group) an exact conditional logistic regression was used at each day and site. The same test was used to determine if there was a statistical difference between groups depending on the isolation day. Clinical scores were summarized and the totals were analysed and compared between groups.

A generalized linear mixed-model was employed to analyze all clinical parameters. Factors included in the model were: pony, treatment, and time as well as their interactions. Since animals were measured over time, the AKAIKE information criterion (AIC) was used to determine an error structure for the auto-regression. The assumptions of the ANOVA were assessed by comprehensive residual analyses. A Shapro-Wilk test, a Kolmogorov-Smirnov test, a Cramer-von Mises test, and an Anderson-Darling test were conducted to assess overall normality. Residuals were plotted against predicted values and explanatory variables (pony, treatment and time) to look for patterns that suggested outliers, unequal variance or other problems. If residual analyses suggested a need for data transformation or data was presented as a percent, analyses were done on a logit or log scale. If the overall f test was significant, a Dunnetts test going back to baseline within a treatment or a tukey test between treatments and sites at each time was applied.

Serological response was defined as a four fold increase in antibody levels from baseline (day 0) to any of the time points in sampling collection (days 7, 14, or 21). Statistical analysis was carried out on SAS 9.1.3 (SAS institute Inc., 2004, Cary, N.C.). Statistical significance was set at P<0.05.

Results

Figure 8:
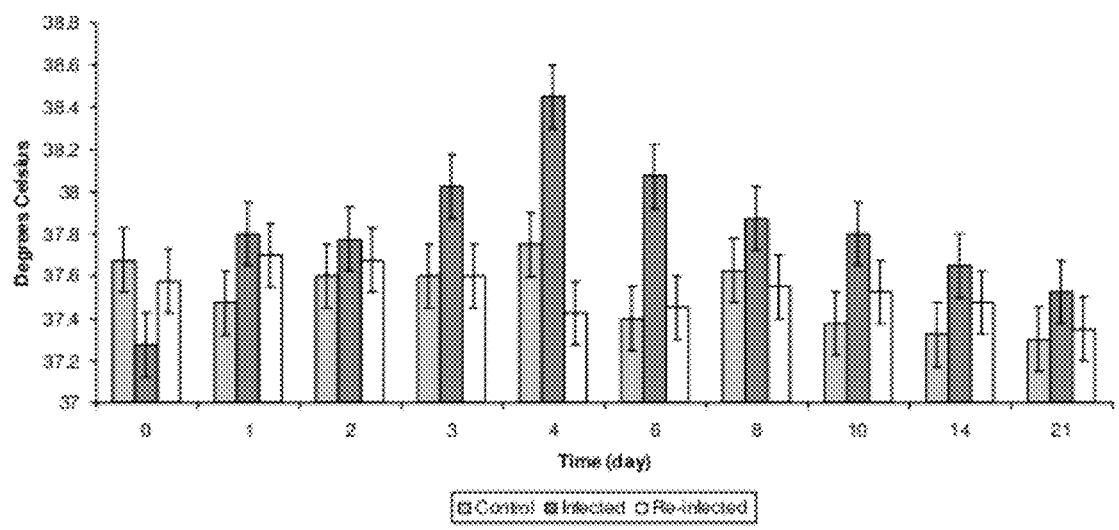
FIG. 8 is a graph of body temperature means from control, infected, and re-infected groups from Example 4.

This study was designed to consistently reproduce ERAV clinical disease in ponies and to study its in vivo characteristics. Pilot studies demonstrated that nebulized ERAV/ON/05 was able to cause clinical respiratory disease in healthy ponies (age 10-12 months). Mild immunosuppression was induced in all ponies except in the re-infected animals to mimic natural conditions under stressful events (e.g. movement for sales, field relocation, vaccination programs, etc.). Results from the main infection study confirmed the results observed during the pilot studies. Ponies in the infected group (n=4) developed respiratory clinical disease that consisted with increased body temperature, lymphadenopathy, increased lung sounds, increased tracheal mucus, and increased nasal discharge (FIG. 7-8). None of these clinical signs were significantly extreme to require additional animal care or supportive treatment. Neither respiratory rate, nor heart rate was significantly different between groups. None of the clinical signs developed by the infected group were observed on the control animals (n=4), which remained healthy throughout the extent of these trials. The etiological agent (ERAV) was only recovered from ponies in the infected group for up to seven days (Table 8). Ponies in the re-infected group (n=4) did not developed clinical respiratory signs and remained healthy throughout the experiments. The statistical analysis of the data collected during these trials demonstrated a significant difference between infected and control animals.

TABLE 15

Equine rhinitis A virus (ERAV) shedding summary. Results of virus isolation from samples collected during the ERAV/ON/05 experimental infection.

| | Sample collection day | | | | | | |
|---|---|---|---|---|---|---|---|
| Sample location | Day 0 | Day 1 | Day 3 | Days 5 | Day 7 | Day 14 | Day 21 |
| Pharyngeal Swab | − | + | + | + | + | − | − |
| Pharynx brush biopsy | − | + | + | + | + | − | − |
| Mid trachea brush biopsy | − | + | + | + | + | − | − |
| Carina brush biopsy | − | + | + | + | − | − | − |
| BAL | − | + | + | − | − | − | − |
| Plasma | − | + | + | + | − | − | − |
| Urine | − | + | − | − | + | − | + |
| Feces | − | − | − | − | − | − | − |

+ Virus was recovered from clinical sample on cell culture (RK-13 cells)
− Virus was not recovered from clinical sample
BAL Bronchoalveolar lavage Neither depression, nor appetite lost was recorded in either group. As well hydration, urination, defecation, and gastrointestinal movements remained unchanged on all groups during the infection trials. There was no difference between re-infected and control animals on the clinical scores and virus isolation test, since no clinical disease was observed on the re-infected animals and the virus could not be recovered from this group.

Clinical Findings

All ponies were considered to be healthy prior to these experiments. ERAV/ON/05 exposure induced clinical respiratory disease in infected animals compared to controls and re-infected animals. The main clinical signs detectable by physical examination were pyrexia, nasal discharge, and lymphadenopathy. Endoscopic examination also revealed the presence of large volumes of mucus and hyperaemia in the mid trachea and lower airways of the infected animals.

Rectal Temperature

No significant differences in daily rectal temperature were found between groups prior to viral or placebo exposure. A significant treatment effect was identified when infected animals were compared to controls and re-infected (p=0.002). When the body temperature from the three groups was compared at different times, the infected group was significantly different compared to controls and re-infected animals (p=0.028). Increased body temperature was detected 24 hours post-infection only in the infected animals and was significantly different from day 2.5 to day 6 when compared to control animals at the same time points (p=<0.005). The body temperature increase picked on day 4 with a mean body temperature of 38.45° C. (SE=0.15) (p=0.001) and persisted for two more consecutive days (FIG. 8). No statistical difference was found when body temperatures from control and re-infected groups were compared at different times. Animals in the control and re-infected groups did not have a significant change in their body's temperature when comparing baseline to individual points in time within the groups (days 1, 7, 14 and 21).

Lymph Nodes

Figure 7:
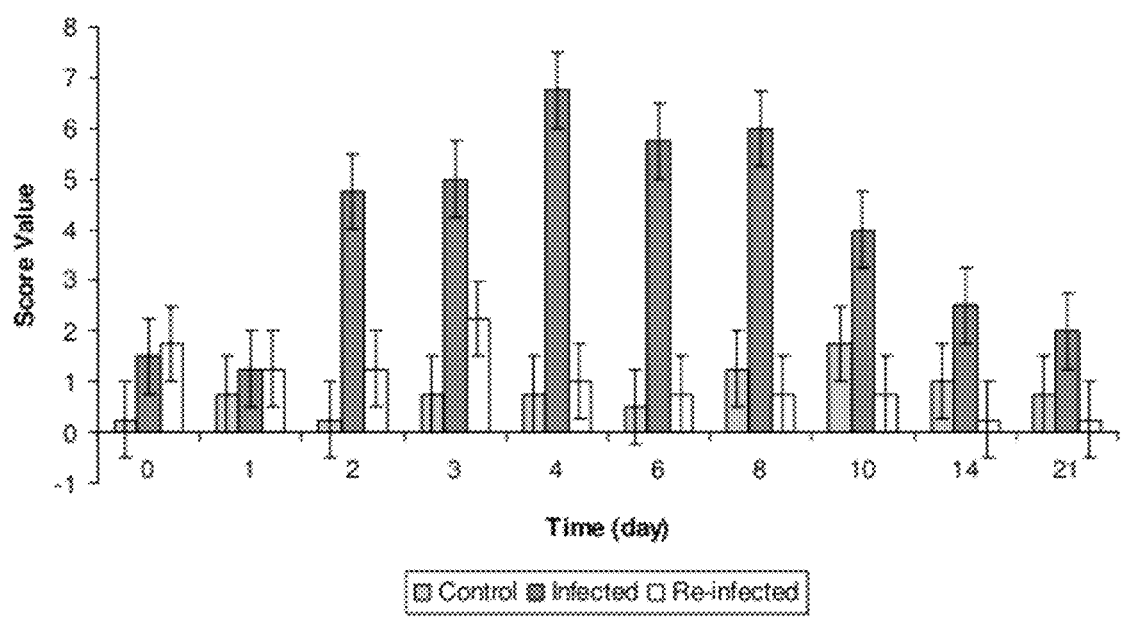
FIG. 7 is a graph of total clinical score means from control, infected, and re-infected groups from Example 4.

Submandibular and retropharyngeal lymph nodes were examined daily and classified as non palpable, palpable and enlarge. Palpability or enlargement of the lymph nodes was only recorded on the infected and re-infected animals. In all infected ponies, the submandibular area became sensitive to palpation on day two and in most cases persisted for up to two weeks. The submandibular lymph nodes size in the infected animals varied from 3 to 5 cm in length by 2 to 3 cm in thickness, and the analysis of the total scores demonstrated a statistical difference between groups (p=<0.0001) (FIG. 7). Interestingly, the retropharyngeal lymph nodes were not consistently palpable in all infected animals, but a significant change in size was recorded in one pony. This lymphadenopathy did not appear to interfere with food or water consumption and the sensitivity to palpation became less pronounce as the days progressed. Submandibular lymph nodes were palpable in three animals from the re-infected animals with an average size of less than one cm in length and 0.5 cm in thickness approximately. Control animals had no detectable lymph nodes changes at palpation throughout the infection experiments.

Heart and Respiratory Rate

Respiratory rate (RR) and heart rate (HR) means were not significantly different between treatment groups (P=0.1) at any time points. In general RR and HR were within the normal physiological parameters and small changes were only associated with handling and sample collection. The highest RR mean among all groups was identified on day 0 and the lowest mean from all the groups was recorded on day 21.

Endoscopic Examination

On the endoscopic examination, infected animals had an increase amount of tracheal mucus detectable on day one that persisted up to day 21. Neither the control nor the re-infected animals had mucus secretions detectable at endoscopic examination throughout these experiments.

Characteristics of the mucus varied from clear and serous on day one to mucoid on days 7-21. Mucus patches were consistently distributed from the upper trachea to the bifurcation of the carina. Localized tracheal hyperaemia was observed in all infected and in some control animals throughout these experiments. The carina on all infected animals was blunted and in some cases hyperaemic starting on day three. Sensitivity to endoscopic examination was noticeably increased by day seven on infected animals and bronchoconstriction was observed during BAL. Nasal discharge varied from mild to moderate in all infected ponies and was not present in the control and re-infected groups. Serous nasal discharge was observed during clinical examination for about 8 days on the infected animals starting between 36 and 48 hours post-infection. However this discharge was not a reflection of the mucus (characteristics and volume) observed during endoscopic examination. Mild ocular discharge was observed inconsistently in the infected animals.

Serology

A total of 12 ponies (age 10 to 12 months) were infected with ERAV/ON/05 or placebo by nebulization. All ponies were serologically negative to ERAV, ERBV, AE2, and EHV1/4 and in a healthy condition prior to the infection experiments. Following exposure to ERAV/ON/05 all infected animals (100%) seroconverted (four fold increase) to ERAV determined by the virus neutralization test (VN) (FIG. 9). A significant treatment by day interaction was observed in infected animals (P=<0.0001). A statistical difference between infected and re-infected animals was found on baseline and day 7 (P=<0.001). In the re-infected group no statistical differences were found when titers to ERAV on days 7, 14, and 21 were compared back to baseline.

Antibody titers against ERAV were significantly elevated in infected animals from day 7 and in most cases peaked by day 14 and maintained to day 21 (P=<0.001). In contrast, all control animals remained seronegative to ERAV and no detectable changes were identified by the VN test. Animals in all groups did not show an increase in antibody levels or serological conversion to any other respiratory viruses (ERBV, AE2, and EHV1/4) during these experiments (FIG. 9). Animals in the re-infected group (n=4) did not have a significant difference in antibody titers to ERAV between baseline and day 21 post-infection. However, a small change in antibody levels to ERAV was detected in 3 ponies and a four fold increase in one pony from the same group (FIG. 9).

Virus Isolation

Nasopharyngeal swabbing, laryngeal brushing, tracheal brushing, BAL, fecal and urine samples were negative for virus isolation (equine respiratory viruses) on all ponies prior to infection (Table 8). Swabs obtained from the nasopharynx from infected and control animals after completing nebulization were cultured on RK-13 cells and ERAV was recovered on a first passage from all infected animals only. RT-PCR using primers that targeted the VP1 gene confirmed the positive and negative diagnoses from both groups.

Virus isolation results from the infection and re-infection trials are summarized on Table 8. A significant difference between infected, control and re-infected animals was identified when comparing virus isolation between groups (P=<0.05). ERAV was only recovered from animals in the infected group on specific days and specific areas of the respiratory tract (Table 8). No other viruses were recovered from samples collected during theses experiments. All ponies in the control group were negative in the virus isolation tests throughout the study. A treatment by day interaction on infected animals was first detected on day 7 and persisted on days 14 and 21 (P=<0.05).

Location for virus recovery varied from the lower airways on days 1, 3, and 5 to mid and upper airways on days 1, 3, 5, and 7. On day one ERAV was isolated from the pharynx and carina from all the ponies in the infected group and the mid trachea and BAL from 3 ponies from the same group. All attempts for virus recovery from feces in all groups were unsuccessful. Virus isolation from urine and plasma was achieved only in rare occasions (Table 8). Virus recovery was gradually decreased from day 1 up to day 7 when ERAV was consistently recovered from clinical samples. This last viral recovery was associated with an increase in antibody titre to ERAV and a decrease in the clinical signs scoring (FIGS. 7 and 9).

Pulmonary Function Testing (PFT)

Hyperactivity of the airways was assessed based on the physiological and clinical response to histamine provocation. Data from infected and control animals were plotted and triggering histamine doses were calculated. Interestingly, ponies from both groups (infected and control) responded on day 0 to a low dose of histamine (<6 mg of histamine). Overall, the triggering histamine doses did not go beyond 13 mg. The clinical histamine reaction (dose-dependant) was observed as hyperventilation associated with abdominal lift and breathing difficulty. The physiological reaction was detected in the PFT by a 35% drop in lung dynamic compliance ($C_{dyn}$) or a doubling in the transpulmonary pressure ($\Delta Ppl$) when comparing saline and histamine administration. Ponies in the infected group showed a small reduction to the histamine triggering dose from day 0 to day 1. However, this was not significantly different between groups. A significant difference between infected and controls was detected on day 21 (P=0.02).

BAL Fluid Differential Cell Counts

Differential cell counts were carried out on the cytospin slides prepared from BAL fluid aliquots. No significant differences in the cell counts were found among horses in the different treatment groups prior to the infection trial. No treatment by day effect was detected on the macrophage and epithelial cells percentages throughout the experiments. A significant increase in the number of neutrophils was observed on day 7 post-infection in the infected group (P=<0.05). These numbers were not significantly different on the control or re-infected animals when comparing base line to days 7, 14, and 21. The mean percentages of lymphocytes, eosinophils and mast cells were proportionally decreased on day 7 post-infection in the infected animals and a statistical difference was detected (P=<0.05). Ciliated epithelial cells were commonly observed on the slides from infected and control animals, however, no significant differences were detected, except on one of the infected animals that had a high count on day 7. In general, a non-septic suppurative inflammation with the presence of epithelial cells and sporadic giant cells was detected in the infected ponies. Interestingly, no major changes in the cytological examination were observed on the samples from the re-infected animals.

This study demonstrates that ERAV/ON/05 induced clinical respiratory disease in infected ponies. Serology demonstrated that no other respiratory viruses were present during these trials. The disease is characterized by pyrexia, nasal discharge, increased lung sounds, and increased submandibular lymph nodes size. Additionally, large volumes of mucus were endoscopically detected in the lower airways that persisted up to day 21. The virus was isolated from the lower and upper airways up to day 7 corresponding with the appearance of detectable equine rhinitis A virus (ERAV) antibodies. None of the re-infected animals developed clinical disease and only one pony from this group had a four fold increase in the antibody titers to ERAV. Ponies with pre-existing ERAV antibodies did not develop clinical disease when exposed to the virus.

Example 5

This example illustrates one embodiment of a Equine Rhinitis B Virus composition in accordance with the present invention.

Materials and Methods

Equine Rhinitis B Virus strain 07-10342 (ATCC Accession No PTA-11829) was recovered from Rabbit-kidney-13 (RK-13) cell culture from a nasal swab from a horse in Ontario Canada. Inactivated 07-10342 was produced following the general procedure described in Example 1 for ERAV/ON/05.

The following compositions containing ERBV alone or in combination with ERAV were prepared.

TABLE 16

Vaccine Groups

| Vaccine Group | Vaccine | Titers A/B | Adjuvant | Volume |
|---|---|---|---|---|
| 1 (N = 8) | Monovalent B - High | 7.5 | HRA-5 | 200 mL |
| 2 (N = 8) | Monovalent B - High | 7.5 | HRA-3 with CSO | 100 mL |
| 3 (N = 8) | Monovalent B - Low | 7.0 | HRA-5 | 200 mL |
| 4 | Bivalent A and B - High | 8.0/7.5 | HRA-5 | 200 mL |
| 5 | Bivalent A and B - High | 8.0/7.5 | HRA-3 with CSO | 100 mL |

Eight horses from each of vaccine groups 1, 2, and 3, were challenged along with eight control horses with a $10^{6.6}$ $TCID_{50}$ challenge dose. Disease status based on nasal discharge and conjunctivitis scores as indicated in Table 10. Effect of vaccination on duration, severity, and incidence of disease is shown in Tables 17-22.

TABLE 17

Disease status scoring

| Disease Status | Nasal Score | Conjunctivitis Score |
|---|---|---|
| Normal (0) | 0 or 1 | 0 or 1 |
| Mild (1) | 0 or 1 | 2 |
| Mild (1) | 1.5, 2, or 3 | any |
| Moderate (2) | 4 or 6 | any |

Vaccinated group showed a significant reduction (Table 18) in duration of nasal discharge including in some cases no signs of mild respiratory disease.

TABLE 18

Number of days with mild, moderate, or severe respiratory disease

| Vaccine Group | Minimum | 25th quantile | 50th quantile | 75th quantile | Maximum |
|---|---|---|---|---|---|
| Control (N = 8) | 1 | 5 | 8 | 8 | 9 |
| 1 (N = 8) | 0 | 0 | 1 | 3.5 | 7 |
| 2 (N = 8) | 0 | 0.5 | 1 | 6.5 | 8 |
| 3 (N = 8) | 0 | 1 | 1 | 3 | 6 |

The number of days animals were sick with clinical signs of respiratory disease (nasal score>0) was significantly shorter in the vaccinated group compared to the control group.

TABLE 19

Effect of vaccination on duration of disease

| | Control | Vaccinate | Shift in days | 95% confidence interval |
|---|---|---|---|---|
| Duration vs Group 1 | 8 | 1* | 5 | 1, 8 days |
| Duration vs Group 2 | 8 | 1* | 2 | 0, 8 days |
| Duration vs Group 3 | 8 | 1* | 7 | 1, 7 days |

*Significantly lower than the control group by Kruskal-Wallis test (P < 0.05)

Immunization with ERBV also lessened the severity of the disease with a lower percentage of vaccinates than controls demonstrating mild and moderate clinical signs of respiratory disease throughout the study (Table 20).

TABLE 20

Summary of the severity of disease based on the maximum respiratory score

| Vaccine Group | Normal | Mild | Moderate |
|---|---|---|---|
| Control (N = 8) | 0% (0/8) | 87.5% (7/8) | 12.5% (1/8) |
| 1 (N = 8) | 37.5% (3/8) | 50.0% (4/8) | 12.5% (1/8) |
| 2 (N = 8) | 25.0% (2/8) | 75.0% (6/8) | 0.0% (0/8) |
| 3 (N = 8) | 12.5% (1/8) | 87.5% (7/8) | 0.0% (0/8) |

Immunization with ERBV was found to significantly reduce the incidence of disease, by 37.5%, 25%, and 12.5% in vaccinated groups 1, 2, and 3, respectively (Tables 21 and 22).

TABLE 21

Effect of vaccination on incidence of disease (disease statuses of mild and moderate were pooled for the purposes of this evaluation)

|  | Control (n = 8) | Group (n = 8) | Prevented fraction | 95% confidence interval |
|---|---|---|---|---|
| Control vs. Group 1 | 1 | 62.5% | 0.375 | −0.069, 0.6346 |
| Control vs. Group 2 | 1 | 75.0% | 0.25 | −0.119, 0.4973 |
| Control vs. Group 3 | 1 | 87.5% | 0.125 | −0.137, 0.3266 |

Vaccination also reduced the shedding of virus from the nares indicating lesser clinical disease in the vaccinated horses as well as demonstrating the effectiveness of the vaccine in preventing spread of the infectious disease to other potentially susceptible horses (Table 22).

TABLE 22

Incidence of virus positive over time

| Day | Control | Group 1 | Group 2 | Group 3 |
|---|---|---|---|---|
| 0 | 0.250 | 0.25 | 0.000 | 0 |
| 1 | 0.625 | 0.25 | 0.125 | 0 |
| 2 | 0.125 | 0.00 | 0.000 | 0 |
| 3 | 0.125 | 0.00 | 0.000 | 0 |
| 4 | 0.250 | 0.00 | 0.000 | 0 |
| 5 | 0.125 | 0.00 | 0.000 | 0 |
| 6 | 0.125 | 0.00 | 0.000 | 0 |
| 7 | 0.125 | 0.00 | 0.125 | 0 |

Results and Discussion

Inactivated ERBV vaccines were found to be capable of immunizing an animal to high levels of antibody detection. The vaccines reduced the duration, severity, and incidence of disease in immunized animals challenged with ERBV. Vaccination also reduced the shedding of infectious virus from ill horses. No unacceptable adverse reactions either at the injection sites or by manifestation of signs of systemic illness were observed. The vaccines are safe and well tolerated for administration in Equine rhinitis B susceptible species, particularly equidae.

Example 6

This example illustrates a guinea pig model for use in a release potency assay.

Vaccine 5 (A/B-1) and Vaccine 6 (A/B-2) were each administered to guinea pigs (five guinea pigs per vaccine, 0.5 mL per intramuscular vaccination). A booster vaccination shot was administered three weeks later. After 19 days, the pigs were bled and blood was analyzed using serum neutralization tests for ERAV and ERBV.

TABLE 23

Vaccine 5 (A/B-1) Batched with $10^{8.0}$ A/$10^{7.5}$ B, with HRA-5 adjuvant

| Guinea Pig | ERVA Titer | ERVB Titer |
|---|---|---|
| 1 | >1414 | 280 |
| 2 | 1300 | 180 |
| 3 | 448 | 120 |
| 4 | 1123 | 360 |
| 5 | 893 | 1120 |
| Back titer | 191 | 260 |

TABLE 24

Vaccine 6 (A/B-2) Batched with $10^{8.0}$ A/$10^{7.5}$ B, with HRA-3 + cottonseed oil adjuvant

| Guinea Pig | ERVA Titer | ERVB Titer |
|---|---|---|
| 1 | 194 | 220 |
| 2 | 326 | 280 |
| 3 | 194 | 560 |
| 4 | 282 | 240 |
| 5 | No Sample | No Sample |
| Back titer | 191 | 260 |

Example 7

This example illustrates a challenge evaluation of Rhinitis Virus A after vaccination with a 2 dose equine Rhinitis A/Rhinopneumonitis/Influenza Killed Virus Vaccine and protection against Equine Rhinitis A respiratory infection after vaccination with the Rhinitis A/Rhinopneumonitis/Influenza Killed Virus Vaccine.

Objective

The objective of this vaccination-challenge study was to demonstrate efficacy of Equine Rhinitis A (ATCC Accession No. PTA-11828) for Equine Rhinitis A/Rhinopneumonitis/Influenza Killed Virus Vaccine. The primary outcome variable used to evaluate the efficacy of vaccination was reduction of respiratory disease caused by Equine Rhinitis A virus.

Material and Methods

The vaccine used in this study is an Equine Rhinitis A/Rhinopneumonitis/Influenza Vaccine of the present invention, Killed Virus vaccine.

A. Equine Rhinitis A Virus

The original Equine Rhinitis Virus A Strain (ERhA V) was obtained from University of Guelph, Animal Health Laboratory, as Isolate number 04-54188, and was received on Sep. 9, 2008 under Import Permit No. 106930. The virus was passed once on E-Vero cells to produce a high titered pre-master stock and was then diluted with cell culture media to produce the Master Seed Virus (MSV). The MSV is designated as ERhA V (04-54188), MSV, Lot 091508A-diluted, 24 Sep. 2008, and was approved for use for Establishment 597 by USDA on Jun. 18, 2010.

The Equine Rhinitis A viral antigen used in vaccines evaluated in this study was a MSV+5 virus produced on the twentieth passage of APHIS approved E-Vero cells. Following growth, viral fluids were filtered, formalin inactivated, and concentrated in accordance with the Outline of Production for Product Code A522.20. The inactivated viral fluids were tested for residual live virus after inactivation. The results were satisfactory. Inactivated viral fluids were used to formulate vaccine at an antigen inclusion level of $10^{7.5}$ TCID$_{50}$/mL.

1. Experimental Vaccine Rhinitis Combo Lot 122110

Experimental vaccine Rhinitis Combo Lot 122110 was formulated based on pre-inactivation titers.

The final formulated vaccine contained the following ingredients per 1 mL dose:

| Equine Rhinitis A | $10^{7.5}$ TCID$_{50}$/mL |
|---|---|
| EHV-1 | $10^{7.0}$ TCID$_{50}$/mL |
| EHV-4 | $10^{6.5}$ TCID$_{50}$/mL |
| Influenza A2/Ohio/03 | $10^{7.0}$ TCID$_{50}$/mL |
| Influenza A2/KY/95 | $10^{7.0}$ TCID$_{50}$/mL |
| Influenza A2/NewMarket/2/93 | $10^{7.0}$ TCID$_{50}$/mL |
| Adjuvant (MVP Laboratories, S.O. #25) | 100 μL |
| Diluent, MEM-E containing | q.s. |
| Gentamicin, 30 μg/mL of diluent volume | |
| Formaldehyde, 0.1% of diluent volume | |
| Amphotericin B, 2.5 μg/mL | |

B. Experimental Horses

1. Description of Experimental Horses

Forty (40), six to eight-month old, draft-cross horses purchased from Steve Waagen, Bottineau, N. Dak. were microchipped upon arrival at Equine Resources, LLC, Butler, Mo. and were assigned to either IVP (Investigational Veterinary Product) or Control Product (CP) based on random number generator after being pre-screened for rhinitis A titers of ≤1:4.

During the entire study, horses were quartered in a single large paddock with common feed bunks, waterers and hay racks. Upon challenge, each animal was assigned a 2 digit "barn code" by laboratory personnel that was attached to a halter worn throughout the post-challenge time period and used to identify horses when clinical signs and samples were taken each day. During each observation day, horses were corralled into holding pens and worked randomly through individual restraining chutes.

Table 25 summarizes the study design:

TABLE 25

Study Design

| Group | No. Test Animals | Treatment | Doses (21 day intervals) | Route of Administration | Challenge (Study Day) |
|---|---|---|---|---|---|
| 1 | 20 | IVP | 2 × 1 mL | IM | D46 |
| 2 | 20 | CP | 2 × 1 mL | IM | D46 |

2. Vaccination/Challenge and Sampling Schedule

On Jan. 28, 2011 and Feb. 18, 2011, experimental vaccine Rhinitis Combo Lot 122110 was administered intramuscularly in a 1 mL dose volume to each of 20 horses (vaccinate group, IVP). Twenty horses (control group, CP) received a 1 mL dose of adjuvanted MEM-E (Experimental product 005) containing the excipients used in the Lot 122110 vaccine (adjuvant, gentamicin, amphotericin B, and formaldehyde) but no antigens. All horses were challenged by intranasal aerosolization of virulent Equine Rhinitis A virus at Study Day 46 (25 days post-booster vaccination) on Mar. 15, 2011. Table 26 shows the schedule of events.

TABLE 26

Schedule of Events:

| Calendar Date | Study Day | Study Event |
|---|---|---|
| Jan. 28, 2011 | 0 | Randomize horses to groups |
| | | Collected serum samples all horses |
| | | IVP administered to Group 1 |
| | | CP administered to Group 2 |

TABLE 26-continued

Schedule of Events:

| Calendar Date | Study Day | Study Event |
|---|---|---|
| Feb. 18, 2011 | 21 | Collected serum samples all horses |
| | | IVP administered to Group 1 |
| | | CP administered to Group 2 |
| Mar. 15, 2011 | 46 | Challenge Groups 1 and 2 |
| | | Body Temperatures |
| | | Whole blood samples (virus isolation) |
| | | Nasal Swabs (virus shedding) |
| | | Clinical observations |
| Mar. 16-21, 2011 | 47-52 | Body Temperatures |
| | | Whole blood samples (virus isolation) |
| | | Nasal Swabs (virus shedding) |
| | | Clinical observations |
| Mar. 22, 2011 | 53 | Serum samples |
| | | Body Temperatures |
| | | Whole blood samples (virus isolation) |
| | | Nasal Swabs (virus shedding) |
| | | Clinical observations |
| Mar. 23-28, 2011 | 54-59 | Body Temperatures |
| | | Whole blood samples (virus isolation) |
| | | Nasal Swabs (virus shedding) |
| | | Clinical observations |
| Mar. 29, 2011 | 60 | Serum samples |
| | | Body Temperatures |
| | | Whole blood samples (virus isolation) |
| | | Nasal Swabs (virus shedding) |
| | | Clinical observations |
| Mar. 30-Apr. 4, 2011 | 61-66 | Body Temperatures |
| | | Whole blood samples (virus isolation) |
| | | Nasal Swabs (virus shedding) |
| | | Clinical observations |
| Apr. 5, 2011 | 67 | Serum samples |
| | | Body Temperatures |
| | | Whole blood samples (virus isolation) |
| | | Nasal Swabs (virus shedding) |
| | | Clinical observations |
| | | End of Study |

3. Intranasal Challenge Inoculation of Horses a. Challenge Virus

The challenge virus Equine Rhinitis A lot 112108A was produced in tissue culture on E-Vero cells. The titer of the challenge virus was determined to be $1 \times 10^{7.3}$ TCID$_{50}$/mL on the day of challenge.

b. Intranasal Challenge Method

Sedivet® (romifidine hydrochloride), a sedative and analgesic, was administered intravenously to each horse prior to challenge at a dosage of 50 μg/kg of body weight. The challenge virus was administered intranasally as an aerosol produced by a nebulizer into an Equine AeroMask (Trudell Medical International, Ontario, Canada) by the following method: Four milliliters of $10^{7.3}$ TCID$_{50}$/mL challenge virus were placed into the nebulizer cup in the AeroMask device. A pressure hose was fitted from an air compressor to the inlet port of the nebulizer. The outlet tube was then inserted into the AeroMask attached to the head of the horse being challenged and approximately 10 psi of air pressure was applied to the inlet port for three minutes. During this time approximately two milliliters of challenge virus fluid was aerosolized directly into the nostrils of the horse being challenged. Challenge virus was administered to horses undiluted, effecting a challenge amount of $1 \times 10^{7.6}$ TCID$_{50}$ in a 2 mL dose.

C. Pre and Post Challenge Evaluation Parameters

1. Nasal Exudate Evaluation

All nasal exudate observations were made prior to collection of nasopharyngeal swabs. On the Day of Challenge (D46) and for 21 days post challenge, the nasal passages and muzzle of each of the 40 vaccinate and control horses were examined and graded using the grading and scoring description listed below.

The scoring grades of 0 through 6 were assigned on the basis of the severity of the disease indicated by each of the following classification:

| Description of Symptoms | Score Sheet Designation | Score |
|---|---|---|
| Essentially normal indicates the horse was clean and essentially free of nasal exudate | EN | 0 |
| Slight clear serous discharge that may be frequently observed in both diseased and normal horses | C-1 | 1 |
| Very slight mucopurulent discharge indicates that mucus was definitely present in small amounts in either one or both nostrils | VSM | 1.5 |
| Moderate clear serous discharge is indicative of a definite increase in volume over that normally observed/slightly mucopurulent is a discharge easily observed in one or both nostrils | C-2/SM | 2 |
| Copious clear serous discharge that is generally observed only in diseased horses | C-3 | 3 |
| Moderately mucopurulent indicates that mucoid discharges were present in large quantities in both nostrils | MM | 4 |
| Heavy mucopurulent indicates that copious amounts of a mucoid discharge filled both nostrils | HM | 6 |

2. Ocular Discharge

Ocular discharge was evaluated daily at the time of nasal exudate evaluation. Ocular discharge scores were recorded as 0=normal;
1=mild to moderate ocular discharge and 2=severe ocular discharge.

3. Temperature

Daily rectal temperatures were recorded for each of the 40 vaccinate and control horses on Day of Challenge and for 21 days post challenge by means of a calibrated, electronic thermometer (GSA Electronics) probe. The daily rectal temperatures were recorded in degrees Fahrenheit (° F.).

4. Nasopharyngeal Viral Isolation

On each observation test day each nasal passage of each vaccinated and control horse was swabbed deeply by means of a sterile WECK-CEL® surgical spear (Edward Weck and Company, Inc., Research Triangle Park, N.C. 27709) attached to an 11-inch long sterile plastic pipette. On collection, each of two surgical spears was immediately placed in a single tube containing 4 mL of chilled transport medium (E-199 supplemented with gentamicin, L-glutamine, 2× Pen/Strep, 2× Amphotericin B).

For isolation of virus, the tubes were mixed, the swabs aseptically removed, and the medium centrifuged at 1500 rpm for 10 to 15 minutes to remove particulates. Medium was filtered through a 0.2μ syringe filter prior to inoculation on tissue culture cells. After filtration, 4-6% of sterile 85% sucrose solution was added to each sample for freezing at −80° C. in order for all samples to be tested concurrently.

On the day of testing, one mL of the thawed, clarified transport medium was used to inoculate a 2 cm² two day old monolayer of E-Vero cells grown in a 24 well tissue culture plate from which the growth medium had been aseptically removed. Following inoculation, the inoculum was allowed to adsorb on the cell monolayer for at least one hour at 37° C. in a humidified incubator containing a 5% $CO_2$ atmosphere. After the adsorption period, an additional 1 mL of re-feed medium (E-199 containing 2 mM L-glutamine, Gentamicin 2× Pen-Strep and 2× Amphotericin B) was added to each well. Following addition of re-feed media the plates were then incubated at 37° C. in a $CO_2$ incubator. Each test and control tissue culture well was examined microscopically for 7 days for signs of cytopathic effect (CPE) typical of the Equine Rhinitis A challenge virus. Wells that were negative at the end of the 7 day observation period were subcultured onto fresh cells and observed for an additional 7 days.

Statistical Evaluation Methods

Horses were classified to a range of respiratory disease status, on a daily basis. The classification to disease status included combining the nasal and ocular evaluations. The algorithm used is detailed below:

| Disease Status | Nasal Score | Ocular Discharge Score |
|---|---|---|
| Normal (0) | 0 or 1 | 0 or 1 |
| Mild (1) | 0 or 1 | 2 |
| Mild (1) | 1.5 | any |
| Moderate (2) | 2 or 3 | any |
| Severe (3) | 4, 5 or 6 | any |

The influence of vaccination on the duration of disease (number of days with at least moderate disease) was evaluated using the Hodges-Lehman (exact) estimate (the NPAR1WAY procedure in SAS, SAS Institute, Cary N.C.).

Severity of disease was evaluated by comparing the maximum disease status between the vaccinated horses and the placebo horses. The mitigated fraction and 95% confidence intervals (CI, asymmetric standard error) were calculated (the FREQ procedure in SAS).

Rectal temperature and serum neutralization titers were analyzed by repeated measures analysis appropriate for continuous data (temperature and log transformed SN titers; ANOVA). SN titers were assumed to be 0 if the titer was reported as <4 and 709 if the titer was reported as >709. SN titers were log transformed prior to the analysis. Buffy coat and nasal swab results on each day were compared using Fisher's exact test.

Results

One horse, #39 (IVP group) died on Day 62 of the study. Upon necropsy at University of Missouri College of Veterinary Medicine, the diagnosis was made of chronic-active, diffuse, severe necrotizing and emphysematous submucosal esophagitis, gastritis, and pharyngitis with intralesional coccobacilli bacterial colonies and plant material, as well as a diffuse severe fibrinosuppurative pleuropneumonia of the lung. The most likely explanation of this death suggests a previous mucosal breach, such as a mucosal ulcer in the cardia of the stomach which allowed seeding of plant material in the associated connective tissues (pathology report attached).

A. Duration

The distribution of the duration of disease (number of days with moderate or severe respiratory disease) in days is summarized in Table 27. The median number of days animals in the placebo group were observed with disease was 14. In the vaccinated group, the median number of days with disease was 1. The duration of disease was significantly lower in the vaccinated animals as compared to the controls (Table 28; P<0.0001).

TABLE 27

Summary of the effect of vaccination on the duration of disease
(Number of days with moderate or severe respiratory disease)

| Group | Minimum | 25$^{th}$ quantile | 50$^{th}$ quantile | 75$^{th}$ quantile | Maximum |
|---|---|---|---|---|---|
| Control (N = 20) | 0 | 10 | 14 | 17 | 18 |

TABLE 27-continued

Summary of the effect of vaccination on the duration of disease
(Number of days with moderate or severe respiratory disease)

| Group | Minimum | 25th quantile | 50th quantile | 75th quantile | Maximum |
|---|---|---|---|---|---|
| Vaccinated (N = 20) | 0 | 0 | 1 | 4 | 12 |

TABLE 28

Effect of vaccination on the duration of disease (Number of days with moderate or severe respiratory disease)

| | Control | Vaccinate | Shift in days | 95% Confidence Interval |
|---|---|---|---|---|
| Duration (median days) | 14 | 1 | 11 | −14, −8 |

Severity

The distribution of the severity of disease is summarized in Table 29. The severity of disease was significantly lower in the vaccinated horses as compared to the placebo horses (Table 30; mitigated fraction=0.7550, 95% CI=0.5518, 0.9582). Individual outcomes are provided in Table 31.

In Table 31 the values for horse #39 which died on Day 62 of the study are reported as 0's from Day 62 through 67, but in the analysis only values >1 are considered, therefore not affecting the outcome. Duration is 1 day for this horse and the max score is 3.

TABLE 29

Summary of the severity of disease based on the maximum nasal discharge score

| Group | Normal | Mild | Moderate | Severe |
|---|---|---|---|---|
| Control (N = 20) | 0% (0/20) | 5% (1/20) | 20% (4/20) | 75% (15/20) |
| Vaccinated (N = 20) | 5% (1/20) | 35% (7/20) | 55% (11/20) | 5% (1/20) |

TABLE 30

Effect of vaccination on the severity of disease

| | Control n = 20 | Vaccinate n = 20 | Mitigated Fraction | 95% Confidence Interval |
|---|---|---|---|---|
| Severity (mean rank) | 28.05 | 12.95* | 0.7550 | 0.5518, 0.9582 |

*Significantly lower than the placebo group by Wilcoxon's rank sum test (P < 0.05).

TABLE 31

Results from individual animals (shaded regions denote duration of moderate to severe disease.

| Horse | Vacc | Day 46 | Day 47 | Day 48 | Day 49 | Day 50 | Day 51 | Day 52 | Day 53 | Day 54 | Day 55 | Day 56 | Day 57 | Day 58 | Day 59 | Day 60 | Day 61 | Day 62 | Day 63 | Day 64 | Day 65 | Day 66 | Day 67 |
|---|---|---|---|---|---|---|---|---|---|---|---|---|---|---|---|---|---|---|---|---|---|---|---|
| 42849285 | Combo | 0 | 0 | 0 | 0 | 0 | 0 | 0 | 0 | 0 | 1 | 0 | 0 | 0 | 0 | 1 | 0 | 1 | 1 | 0 | 0 | 0 | 0 |
| 42856642 | Combo | 0 | 0 | 0 | 0 | 0 | 1 | 0 | 0 | 0 | 0 | 0 | 0 | 0 | 1 | 0 | 0 | 0 | 2 | 0 | 0 | 0 | 0 |
| 42857074 | Combo | 0 | 0 | 0 | 0 | 0 | 0 | 1 | 0 | 0 | 2 | 2 | 2 | 2 | 2 | 2 | 2 | 0 | 0 | 0 | 0 | 0 | 0 |
| 42860382 | Combo | 0 | 0 | 0 | 0 | 0 | 0 | 2 | 2 | 2 | 2 | 2 | 2 | 0 | 0 | 1 | 0 | 0 | 0 | 0 | 0 | 1 | 0 |
| 42861051 | Combo | 0 | 0 | 0 | 0 | 0 | 1 | 1 | 0 | 0 | 0 | 0 | 0 | 0 | 0 | 0 | 0 | 1 | 0 | 0 | 0 | 0 | 0 |
| 42876062 | Combo | 0 | 0 | 0 | 0 | 0 | 0 | 1 | 1 | 0 | 0 | 1 | 0 | 0 | 1 | 0 | 0 | 0 | 0 | 0 | 0 | 0 | 0 |
| 42878629 | Combo | 0 | 0 | 0 | 0 | 0 | 1 | 0 | 0 | 0 | 2 | 2 | 1 | 2 | 2 | 2 | 2 | 2 | 2 | 2 | 0 | 0 | 1 |
| 42889377 | Combo | 0 | 0 | 0 | 0 | 0 | 0 | 0 | 0 | 0 | 0 | 1 | 0 | 0 | 0 | 0 | 0 | 0 | 0 | 2 | 0 | 0 | 1 |
| 42889622 | Combo | 0 | 0 | 0 | 0 | 0 | 1 | 0 | 1 | 0 | 0 | 2 | 2 | 0 | 0 | 0 | 0 | 0 | 0 | 0 | 0 | 0 | 0 |
| 42890836 | Combo | 0 | 0 | 0 | 0 | 0 | 0 | 0 | 0 | 0 | 0 | 0 | 0 | 1 | 0 | 0 | 0 | 0 | 0 | 0 | 0 | 0 | 0 |
| 43315773 | Combo | 0 | 0 | 0 | 0 | 0 | 0 | 0 | 0 | 0 | 0 | 2 | 0 | 0 | 0 | 0 | 0 | 0 | 0 | 0 | 0 | 0 | 0 |
| 108356559 | Combo | 0 | 0 | 0 | 0 | 0 | 0 | 0 | 0 | 2 | 1 | 2 | 2 | 2 | 2 | 2 | 2 | 2 | 2 | 2 | 0 | 0 | 0 |
| 108357033 | Combo | 0 | 0 | 0 | 0 | 0 | 1 | 0 | 0 | 1 | 0 | 0 | 0 | 0 | 0 | 0 | 0 | 0 | 1 | 0 | 0 | 0 | 0 |
| 108361284 | Combo | 0 | 0 | 0 | 0 | 0 | 0 | 0 | 0 | 0 | 0 | 0 | 0 | 0 | 0 | 0 | 1 | 0 | 0 | 0 | 0 | 0 | 0 |
| 108363552 | Combo | 0 | 0 | 0 | 0 | 1 | 0 | 0 | 1 | 0 | 0 | 2 | 0 | 0 | 0 | 0 | 0 | 0 | 0 | 0 | 0 | 0 | 0 |
| 108366283 | Combo | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 108368584 | Combo | 0 | 0 | 0 | 0 | 0 | 0 | 0 | 0 | 0 | 0 | 2 | 0 | 0 | 0 | 0 | 0 | 0 | 0 | 0 | 0 | 0 | 0 |

TABLE 31-continued

| Horse | Vacc | Day 0 | Day 1 | Day 2 | Day 3 | Day 4 | Day 5 | Day 6 | Day 7 | Day 8 | Day 9 | Day 10 | Day 11 | Day 12 | Day 13 | Day 14 | Day 15 | Day 16 | Day 17 | Day 18 | Day 19 | Day 20 | Day 21 |
|---|---|---|---|---|---|---|---|---|---|---|---|---|---|---|---|---|---|---|---|---|---|---|---|
| 108512267 | Combo | 0 | 0 | 0 | 0 | 0 | 0 | 0 | 0 | 0 | 0 | 2 | ▓ | ▓ | 0 | ▓ | ▓ | ▓ | ▓ | ▓ | ▓ | ▓ | ▓ |
| 108513075 | Combo | 0 | 0 | 0 | 0 | 0 | 0 | 0 | 0 | 0 | 0 | 0 | 0 | 3 | 1 | 0 | 0 | 0 | 0 | 0 | 0 | 0 | 0 |
| 108522069 | Combo | 0 | 0 | 0 | 0 | 0 | 0 | 0 | 0 | 0 | 0 | 0 | 0 | 0 | 1 | 1 | 1 | 0 | 0 | 0 | 0 | 0 | 0 |
| 18605089 | Placebo | 0 | 0 | 0 | 1 | 0 | 1 | 0 | 0 | 1 | 2 | 0 | ▓ | 0 | 0 | ▓ | 2 | 2 | ▓ | 2 | 2 | 1 | 0 |
| 42849558 | Placebo | 0 | 1 | 0 | 0 | 0 | 1 | 1 | 2 | 0 | 0 | 1 | ▓ | ▓ | 0 | ▓ | 3 | 2 | 0 | 0 | 0 | 0 | 1 |
| 42850873 | Placebo | 0 | 0 | 1 | 0 | 0 | 2 | ▓ | 1 | 1 | 2 | 1 | ▓ | 0 | 1 | ▓ | 0 | 3 | 2 | 0 | 2 | 2 | 2 |
| 42861315 | Placebo | 0 | 0 | 0 | 1 | 1 | 1 | 1 | 0 | 0 | 2 | 3 | ▓ | 3 | ▓ | 0 | 3 | 0 | 2 | 3 | 0 | 1 | 0 |
| 42865808 | Placebo | 0 | 0 | 0 | 1 | 2 | ▓ | 2 | 2 | ▓ | 2 | ▓ | 2 | 2 | 2 | 0 | 0 | 0 | 2 | 0 | 2 | 1 | 0 |
| 42867036 | Placebo | 0 | 0 | 0 | 1 | 2 | ▓ | 1 | 2 | 2 | 2 | ▓ | ▓ | 0 | 3 | ▓ | 0 | 2 | 1 | 1 | 1 | 1 | 0 |
| 42867892 | Placebo | 0 | 0 | 0 | 1 | 2 | 0 | 2 | ▓ | 2 | 2 | 0 | 0 | 2 | 0 | 0 | 0 | 2 | 0 | 2 | 2 | 0 | 0 |
| 42869592 | Placebo | 0 | 1 | 1 | ▓ | 2 | ▓ | 2 | 2 | 2 | 2 | 2 | ▓ | 2 | 2 | ▓ | 1 | 2 | 1 | 2 | 0 | 1 | 0 |
| 42870316 | Placebo | 0 | 0 | 0 | 1 | 1 | 1 | 1 | 2 | 3 | 3 | 3 | 2 | 0 | 2 | ▓ | 1 | 2 | 1 | 0 | 0 | 0 | 0 |
| 42874866 | Placebo | 0 | 0 | 1 | 1 | 0 | 0 | 1 | 0 | 0 | 2 | 0 | 2 | 2 | 2 | 0 | 1 | 0 | 1 | 0 | 1 | 0 | 0 |
| 42876021 | Placebo | 0 | 0 | 0 | 0 | 0 | 0 | 0 | 0 | 0 | 2 | 0 | ▓ | 0 | 0 | 0 | 2 | 2 | 0 | 0 | 1 | 0 | 0 |
| 42879094 | Placebo | 0 | 0 | 0 | 0 | 0 | 0 | 1 | 0 | 0 | 2 | 0 | ▓ | 0 | 3 | 0 | 0 | 0 | 0 | 0 | 1 | 0 | 0 |
| 42879533 | Placebo | 0 | 0 | 0 | 1 | 0 | 1 | 1 | 1 | 2 | 2 | ▓ | 2 | 1 | 1 | 0 | 2 | 0 | 3 | 0 | 0 | 0 | 0 |
| 42889258 | Placebo | 0 | 0 | 0 | 0 | 0 | 0 | 0 | 0 | 0 | 0 | 1 | 0 | 0 | 0 | 0 | 0 | 0 | 0 | 0 | 0 | 0 | 0 |

TABLE 31-continued

B. Rectal Temperature

The results of the statistical analysis are summarized in Table 32. The vaccine by day interaction was statistically significant. Within day analyses are provided in Table 33 (appendix). On Days 3, 4, and 5, horses in the vaccinated group had statistically significantly lower temperatures than those in the placebo group. On Day 20, horses in the vaccinated group had significantly higher temperatures than those in the placebo group. However, on all days any differences between treatment groups were not clinically meaningful and only one horse (#39) had a rectal temperature greater than 102° F. (39° C.) on any challenge study day.

TABLE 32

Summary of the effect of vaccination on rectal temperature and serum neutralization titers

| | P-Value | | |
|---|---|---|---|
| Outcome | Vaccine | Day | Vaccine * Day |
| Temperature | 0.5754 | <0.0001 | 0.0006 |
| SN titer | <0.0001 | <0.0001 | <0.0001 |

1. Serum Neutralization Titers

The results of the statistical analysis are summarized in Table 32. On Days 46 and 53, horses in the vaccinated group had significantly higher titers than those in the placebo group. On Day 67, horses in the vaccinated group had significantly lower than those in the placebo group.

Discussion

This study was conducted to demonstrate efficacy of the Equine Rhinitis A virus component of an inactivated Equine Rhinitis A virus vaccine in combination with inactivated Equine Herpesvirus types 1 and 4 and Equine Influenza Viruses. Vaccination was given in a 2-dose format, and challenge of virulent Equine Rhinitis A virus was performed 25 days post-booster vaccination. Vaccinated and placebo treated control horses were evaluated to assess effect of vaccination on reduction of severity and duration of clinical respiratory disease. Clinical signs, nasal swabs and buffy coats were evaluated daily for evidence of Equine Rhinitis A disease and presence of the virus in the challenged horses.

Results from this challenge study show a statistically significant and clinically important reduction of both the severity and of the duration of respiratory disease in vaccinates following challenge. As confirmed by mitigated fraction analysis of respiratory disease scores in horses vaccinated with the IVP as compared to horses vaccinated with the control product, moderate/severe signs of respiratory disease were reduced 75.5% (95% confidence interval 96% to 55%). Duration of moderate/severe disease was also significantly reduced by 11 days in vaccinated horses as compared to control horses (95% confidence interval 14 days to 8 days shorter disease duration). In addition, vaccination significantly reduced nasal virus shedding throughout the successive 5 days of peak viral shedding, and viremia also was significantly reduced during the 4 days of peak viremia within the challenge period. Importantly, virus was recovered from buffy coat samples of control horses a total of 54 times over 5 study days in comparison to only 8 total days of viremia over 4 study days in vaccinated horses.

CONCLUSIONS

Data from this study clearly demonstrate that 2×1 mL intramuscular doses of Equine Rhinitis A/Rhinopneumonitis/Influenza Killed Virus Vaccine (Product Code TBD, unlicensed), administered at 21 day intervals between doses to horses, significantly reduced severity and duration of respiratory disease caused by Equine Rhinitis A virulent challenge.

The study results illustrate the use of this vaccine for the immunization of horses six months of age or older against respiratory disease caused by Equine Rhinitis A virus. These data also establish Vaccine Lot 122110 as an acceptable reference vaccine for potency testing of subsequent serials of Equine Rhinitis A/Rhinopneumonitis/Influenza Vaccine, Killed Virus and of Equine Rhinitis A Vaccine, Killed Virus (Product Code 1522.21, unlicensed).

What is claimed is:

1. An immunogenic composition comprising one or more strains of inactivated or live, attenuated Equine Rhinitis A Virus (ERAV), wherein:

(a) said ERAV strain, prior to inactivation or attenuation, causes detectable respiratory disease in at least 50% of seronegative horses exposed to ERAV or ERBV, or grows in a Vero cell culture to 106 TCID50/mL or higher, or, when used as a vaccine in equines at a dose of 106 TCID50 or higher results in a serum titer of at least 1:112; and (b) said ERAV strain comprising a genomic sequence whose reverse transcript has a nucleotide sequence comprising SEQ ID NO: 2 or encodes a polyprotein with an amino acid sequence comprising SEQ ID NO: 3, said ERAV strain, prior to inactivation or attenuation, is active to infect and replicate in host cells.

2. An immunogenic composition according to claim 1, wherein an ERAV strain having an ATCC Accession No PTA-11828 and/or an ERBV strain having ATCC Accession No. PTA-11829 and Amphotericin B, gentamicin sulfate, formaldehyde, and HRA-5.

3. The immunogenic composition according to claim 1, further comprising an ERBV strain comprising a genomic sequence that is the genomic sequence of the ERBV strain having ATCC Accession no. PTA-11829 or encodes a polyprotein that has the amino acid sequence of the polyprotein encoded by the genome of the ERBV strain having ATCC Accession no. PTA-11829.

4. The immunogenic composition according to claim 1, in which the strain of ERAV is inactivated.

5. The immunogenic composition according to claim 1 in which the strain of ERAV is a live, attenuated strain.

6. The immunogenic composition of claim 1 in which the strain, prior to inactivation or attenuation, causes detectable respiratory disease in 100% of seronegative horses upon exposure to ERAV or ERBV.

7. The immunogenic composition of claim 1 in which the strain, prior to inactivation, grows in cell culture to at least $10^8$ $TCID_{50}$/mL.

8. The immunogenic composition of claim 1 in which the strain results in a serum titer of at least 1:1000.

9. The immunogenic composition of claim 1 in which the strain of ERAV or ERBV is ERAV/ON/05 (ATCC Accession No. PTA-11828) or ERBV strain 07-103042 (ATCC Accession PTA-11829).

10. The immunogenic composition of claim 3 in which said ERBV strain comprises a genomic sequence whose reverse transcript of the genomic sequence of the ERBV strain having ATCC Accession no. PTA-11829 or encodes a polyprotein with an amino acid sequence to the polyprotein encoded by the genome of the ERBV strain having ATCC Accession no. PTA-11829, wherein said ERBV strain, prior to inactivation or attenuation, is active to infect and replicate in host cells.

11. The immunogenic composition according to claim 10, wherein the ERBV strain comprises a genomic sequence that is the genomic sequence of the ERBV strain having ATCC Accession no. PTA-11829 or encodes a polyprotein that has the amino acid sequence of the polyprotein encoded by the genome of the ERBV strain having ATCC Accession no. PTA-11829.

12. The immunogenic composition according to claim 1, comprising ERAV and ERBV, wherein the ERAV strain is (ATCC Accession No. PTA-11828) and the ERBV strain has ATCC Accession No. PTA-11829.

13. The immunogenic composition according to claim 1, wherein said immunogenic composition comprises at least one antigen or one inactivated or live, attenuated strain of Equine Herpes Virus.

14. The immunogenic composition according to claim 13, wherein said Equine Herpes Virus is selected from the group consisting of EHV-1 and EHV-4, and a combination thereof.

15. The immunogenic composition according to claim 13, wherein said Equine Herpes Virus is selected from the group consisting of: EHV-1, EHV-4, strains deposited with the ATCC under accession Nos. PTA-9525 and PTA-9526, and a combination thereof.

16. The immunogenic composition according to claim 13, comprising at least one antigen of Equine Herpes Virus.

17. The immunogenic composition according to claim 1, wherein said immunogenic composition comprises at least one antigen or one inactivated or live, attenuated strain of Equine Influenza Virus.

18. The immunogenic composition according to claim 17, wherein said Equine Influenza Virus is selected from the group consisting of Clade 1 viruses, Clade 2 viruses, strains deposited with the ATCC under accession Nos. PTA-9522, PTA-9523, and PTA-9524, and combinations thereof.

19. The immunogenic composition according to claim 17, comprising at least one antigen of Equine Influenza Virus.

20. The immunogenic composition according to claim 1, wherein said immunogenic composition comprises at least one antigen or one inactivated or live, attenuated strain of Equine Herpes Virus and at least one antigen or one inactivated or live, attenuated strain of Equine Influenza Virus.

21. The immunogenic composition according to claim 20, wherein the Equine Herpes Virus is EHV-1 or EHV-4 or a combination thereof.

22. The immunogenic composition according to claim 1, wherein said immunogenic composition further comprises at least one antigen of one or more strains selected from the group consisting of West Nile Virus, Eastern Equine Encephalomyelitis Virus, Western Equine Encephalomyelitis Virus, Venezuelan Equine Encephalomyelitis Virus, and Tetanus Toxoid, and combinations thereof.

23. The immunogenic composition according to claim 1, wherein said immunogenic composition further comprises at least one inactivated or live, attenuated strain selected from the group consisting of West Nile Virus, Eastern Equine Encephalomyelitis Virus, Western Equine Encephalomyelitis Virus, Venezuelan Equine Encephalomyelitis Virus, and Tetanus Toxoid, and combinations thereof.

24. The immunogenic composition according to claim 1, wherein said immunogenic composition further comprises one or more inactivated or live, attenuated strains of Eastern Equine Encephalomyelitis, Western Equine Encephalomyelitis, Venezuelan Equine Encephalomyelitis Virus, and Tetanus Toxoid.

25. The immunogenic composition according to claim 1, wherein said immunogenic composition further comprises one or more inactivated or live, attenuated strains of Eastern Equine Encephalomyelitis Virus, Western Equine Encephalomyelitis Virus, Venezuelan Equine Encephalomyelitis Virus, Equine Influenza Virus, Equine Herpes Virus, and Tetanus Toxoid.

26. The immunogenic composition according to claim 22, wherein said West Nile Virus is the strain deposited with the ATCC under accession number deposited with the ATCC under accession number PTA-9409.

27. The immunogenic composition according to claim 22, wherein said Western Equine Encephalomyelitis Virus is the strain deposited with the ATCC under accession number PTA-9410.

28. The immunogenic composition according to claim 22, wherein said Venezuelan Equine Encephalomyelitis Virus is the strain deposited with the ATCC under accession number PTA-9411.

29. The immunogenic composition according to claim 22, wherein said Eastern Equine Encephalomyelitis Virus is the strain deposited with the ATCC under accession number PTA-9412.

30. The immunogenic composition according to claim 24, wherein said Equine Herpes Virus is selected from the group consisting of the strains deposited with the ATCC under accession Nos. PTA-9525 or PTA-9526, and combinations thereof.

31. The immunogenic composition according to claim 1, wherein any of the strains are present in an amount from about $10^{2.0}$ TCID$_{50}$/mL-$10^{10.0}$ TCID$_{50}$/mL per dose.

32. The immunogenic composition according to claim 1, wherein said immunogenic composition further comprises a suitable pharmaceutical carrier.

33. The immunogenic composition according to claim 32, wherein said suitable pharmaceutical carrier is selected from the group consisting of a diluent, adjuvant, antimicrobial agent, preservative, inactivating agent, and combinations thereof.

34. The immunogenic composition according to claim 33, wherein said adjuvant is HRA-5.

35. A method for reducing the incidence or lessening the severity of clinical symptoms associated with or caused by ERAV or ERBV in an animal or a herd of animals comprising the step of administering the immunogenic composition according to claim 1 to an animal in need thereof.

36. The method according to claim 35, wherein the incidence of clinical symptoms caused by one or more of said pathogens in a herd of animals is reduced as compared to a herd not receiving said immunogenic composition.

37. The method according to claim 35, wherein the administration of at least one dose of said immunogenic composition provides a duration of immunity of at least 12 months against one or more of said pathogens.

38. The method according to claim 35, wherein said animal is a horse.

39. The method according to claim 35, wherein any of the strains are present in an amount from about $10^{2.0}$ TCID$_{50}$/mL-$10^{10.0}$ TCID$_{50}$/mL per dose.

40. The method according to claim 35, wherein said immunogenic composition further comprises a suitable pharmaceutical carrier.

41. The method according to claim 40, wherein said suitable pharmaceutical carrier is selected from the group consisting of a diluent, adjuvant, antimicrobial agent, preservative, inactivating agent, and combinations thereof.

42. The method according to claim 41, wherein said adjuvant is HRA-5.

43. The method according to claim 35, wherein said immunogenic composition is administered in one or more doses.

44. The method according to claim 35, wherein one dose of said immunogenic composition is formulated in a dosage form of 0.5 mL to 2.5 mL.

45. The method according to claim 35, wherein said immunogenic composition is safe for use in foals or horses 4 months of age or older.

* * * * *

SEQUENCE LISTING

```
<160> NUMBER OF SEQ ID NOS: 14

<210> SEQ ID NO 1
<211> LENGTH: 353
<212> TYPE: DNA
<213> ORGANISM: Equine rhinitis A virus

<400> SEQUENCE: 1
atgcctgtag cgtcagtaaa acgcggtaaa cataggcttt gactgtagcg tcagtaaaac      60
gcaacaacca tacgctgttg tgcctgtagc gtcagtaaaa cgcggcaaac gcaagcatta     120
actgtagcgt cagtaaaacg caacaaccat acgctaatgt gcctgaggcg tcagtaaacg     180
catacagcaa accagagctt cccggcttta agggttactg ctcgtaatga gagcacttgg     240
caatttgtca ggatttcctg gtggttgtca cgggagagag gagcccgttt tcgggcactg     300
ttcccaacaa acatttgtgc gcttcggcgc acaccccgct cagccccctg tca            353

<210> SEQ ID NO 2
<211> LENGTH: 7839
<212> TYPE: DNA
<213> ORGANISM: Equine rhinitis A virus
```

```
<400> SEQUENCE: 2
ttcttttttt ttcccttccc tcgatcaccg acgttggggg ggggggggtt gaaaaagttt    60
atgcctgtag cgtcagtaaa acgcggtaaa cataggcttt gactgtagcg tcagtaaaac   120
gcaacaacca tacgctgttg tgcctgtagc gtcagtaaaa cgcggcaaac gcaagcatta   180
actgtagcgt cagtaaaacg caacaaccat acgctaatgt gcctgaggcg tcagtaaacg   240
catacagcaa accagagctt cccggcttta agggttactg ctcgtaatga gagcacttgg   300
caatttgtca ggatttcctg gtggttgtca cgggagagag gagcccgttt tcgggcactg   360
ttcccaacaa acatttgtgc gcttcggcgc acaccccgct cagcccctg tcattgactg    420 gtcgaaggcg ctcgcaataa gactggtcgt cacttggctt ttctatccgt tcaggcttta   480
gcgcgccctc gcgcggcggg ttgtcaggcc cgtgtgctgt acagcaccag gtaaccggac   540
agcagcttgc tggattttcc cggtgccatt gctctggatg tgtcaccaa gctggtggat    600 gaagagtgaa cctgatgaag caacacactt gtggtagcgc tgcccaaaag ggagcggaat   660 tccccgccg cgaggcggtc ctctctggcc aaaagcccag cgttaatagc gccttttggg    720
atgcaggtac cccacctgcc aagtgtgaag tggaatcagc ggatctctga ttcggcctgt   780
actgaactac accatctacc gctgtgaaga atgtcctgaa ggcaagctgg ttacagccct   840
gatcaggagc cccatccatg actctcgatt ggcatggggt caaaaattgt ctaagcagcg   900
gcagggacgc gggagcgttt cctttccatt ttgatttgca tgatggcggc gtctaaagtg   960
tacagggttt gcgagcagac tcttctcgct ggcgccgtgc gcatgatgga caagttttg    1020 cagaagagag ttgttttttgt gccacaccta gataaacagg tacgcctgac aggtcttcac  1080
aactatgaca acacatgttg gcttaatgcc ttgactcagt tgactcagat tcttggaatt   1140 cggcttttg atgaacactt tggaaacaga ggtttgttca ctcggaaaac aattgattgg    1200
gtgagtgacc aaactggaat aaaggattta aaatcaggag cgccacccct cgtggtggtt   1260
tacaagctct ggcaacacgg ccatttggat gtcggcacca tggaaaagcc cagaccaatc   1320
acgctttggt ctgggcccaa agtgtgtctg tctgacatgt gggcgtgtgt ttctgccaag   1380
cctggacacg cagtgttcta tctcttgact gatgaaggat ggatttgcat tgatgacaag   1440
aaaatttatt atgaaacacc agagcccgac gatgtcttgg tcttcgcacc ctatgatttt   1500
gagtcactcg gaaagatcc tcctaggctg caccaaagat acgaaaaggc tttcaaaaag   1560
ttgtcaggag ctgggacctc tactccgaca accgggaatc agaatatgtc gggcaatagt   1620
gggtccattg tccaaaattt ttacatgcaa caataccaaa attcaattga tgcagacctg   1680
ggcgataatg tcatcagtcc tgaaggccaa ggcagcaaca ctagtagctc tacctcctca   1740
agccagtcgt ctggtttagg tggatggttc tctagtctgc tcaacctagg taccaagcta   1800
ctggctgaca aaaagacaga agaaaccaca acattgagg acaggattga gacaacagtt     1860
gtgggagtga cgattatcaa ttcacaaggg tcagttggca caacctattg ttactccaag   1920
cctgacagca agcgccctc cacagtgtct gacccggtca cccggctggg gccaactctt    1980
tctagacact acaccttcaa ggttggagag tggccacact cacaatccca tgggcacgcc   2040
tggatttgcc cactgcccgg ggacaaactt aaaaagatgg gcagtttcca cgaggtggtg   2100
aaggcacacc acttggtgaa gaatggatgg gatgtggttg ttcaggtgaa tgcctctttt   2160
gcccactcgg gagctctttg cgttgcagca gttcctgagt atgaacacac ccatgagaag   2220
gctctaaaat ggtctgagct tgaagaacct gcttatacat atcagcagct ttcagtgttt   2280
ccacatcaat tgttaaattt gagaacaaat tcttctgtac acttggttat gccctatatt   2340
```

```
ggacctgggc caaccacgaa tttgacactt cataacccct ggaccattgt aatcttgatt    2400
ttgtctgaac tgacagggcc tggccagact gtgcccgtca ccatgtcggt ggctcctatt    2460
gacgccatgg tgaatgggcc tctcccaaac ccagaggcac caattagagt ggtttcagta    2520
cctgagtcag attcgttcat gtcttctgtg ccagacaatt ctaccccgct ttatccaaag    2580
gttgtggtcc ccctcggca agtcccaggg aggttcacga attttattga tgtggctaaa    2640
cagacttact cattttgctc catctctggc aagccctatt ttgaggtgac aaatacttca    2700
ggagacgagc ctctgtttca gatggatgtc tccctcagtg ctgctgagtt gcacgggaca    2760
tatgttgcaa gcttgtcatc tttctttgca cagtacaggg gttcactaaa cttcaatttc    2820
atcttcactg gagctgcggc aaccaaagct aaattcttgg tcgccttcgt tcctccccac    2880
acagccgcgc taaaacgcg ggatgaagcc atggcgtgta cacgcagt gtgggatgtc    2940 ggcttgaatt ctgccttttc tttcaatgtg ccttattcat ctccagctga ctttatggcc    3000
gtttactcgg cagaggcaac ggttgtgaat gtgtctggct ggctacaagt ttatgccttg    3060
actgctctca cttcaactga cattgctgtg aatagcaagg gccgtgtttt ggtggccgtt    3120
tctgctgggc cagatttctc acttcgacac cccgtggatc tgcctgacaa gcaggtcaca    3180
aatgtgggcg aggacgggga accaggtgaa actgagcccc gttatgctct gtctccagtg    3240
gacatgcatg ttcatacgga tgtcagcttc ctgctagaca gatttttga tgttgaaaca    3300 attgagcttt caaatttgac tgggtcacca accactcata ttttgaaccc atttggctcc    3360
accgctcagt tggcatgggc taggctgttg aacacctgca catatttctt ttcaaatttg    3420
gagttgtcta taacaattcaa atttacaaca atgccctctt ccgttgaaaa aggcttcgtc    3480
tgggttaagt ggttcccggt tggagcacca acaaaaacaa cagatgcatg gcagcttgaa    3540
ggcggaggca actccgtcag aattcaaaaa ctggctgtgg ctggcctctc acccaccgtt    3600
atttttaaaa ttgctggctc gcggtcgcag gcatgtggct tcaatgtgcc ctacacttca    3660
atgtggcggg ttgtgccagt cttttacaac ggttggggcg cgcccacaaa agagaaagca    3720
acctacaatt ggcttccggg cgcacatttt gggtcgatac ttttgacttc tgatgcacac    3780
gacaagggtg gctgttacct gcggtatcga ttcccgcggg ctagcatgta ctgcccaaga    3840
cctattccgc ccgcattcac ccggccggcg gataagacta ggcacaaatt ccctacaaac    3900
attaacaaac agtgcactaa ttatgccctt cttaaattgg caggtgatgt agagagtaat    3960
cctggcccca ctattttttc taaagcttct gctgatttga acgccctgtc cacctctctt    4020
ggtgagttga ctggtatgct taaggatttg aaagctaagg ctgaaactta ttccccctttt    4080 tataaaatgg caaaaatgtt gtttaaattg gccactctag cggttgccgc tatgagaaca    4140
aaagacccag ttgtagtggt gatgttgata gctgattttg gattggaagt ttttgatacg    4200
ggtttcttct tctcgtattt tcaagagaaa ctgcagcctt atatgaagac cattcccggc    4260
aaagtttctg atttggttac agacgcagct actgctgcag ctcaaattcc aaaaggggtg    4320
tattcttttg tgtcatcttt ctttgagaca ccagaaggtg tggttgagaa acaggtttct    4380
cttaggacta tcaatgatat ttttactctc ttgaaaaatt cggactggtt tattaagacg    4440
ctggttgctc tcaaaaagtg gctggtgtcg tggttcaaac aggaacagca agcagatgat    4500 gcccttatt ctgaattgga aaaataccct ttgtataaat tgaaattgaa ggaaccagac    4560
actcaggagg aggcccgcca gtggttcaaa gacatgcagc agagagcctt ggcagtgaag    4620
gataagggtt tattctctct gttgcaaatc cctcttgtga acttgcctac atcacgtcct    4680
```

```
gaacccgttg tgtgtgtgct gagaggcgcg tccggacagg gcaagtccta tttagcaaac    4740
atgatggctc aggctatttc tcttctccta actgggaaac agaacagtgt gtggagttgc    4800
ccacccgacc ccacatactt tgatggttat aacggacaag ctgttgtcat aatggatgac    4860
ttgggccaaa accctaacgg agcagatttc aagtatttct gtcagatggt gtcaactaca    4920
gcctttgttc caccaatggc ccacttggat gacaagggaa ttccctttac ctctcctgtt    4980
gttatttgta ctacaaattt gcattcctct ttcaccccaa ttactgtgtc atgtcctgag    5040
gctctgaaaa gaaggttccg gtttgacgtg actgtttctg ctaagcctgg ttttgtgagg    5100
actgtggggt cgtctcagct tttgaacttg cctcttgctt tgaagcctgc tggtcttcca    5160
cctcatccta ttttttgagaa tgacatgccc attttgaatg gtcaggctgt gaaattggct    5220
ttgtcaggtg ttgaagtgac cgcctttgag ttaattgaga tgattttgtc tgaggtgcag    5280
aatagacagg acacacacaa gatgcctatt tttaaacagt cctggtctga tttgttcaag    5340
aagtgtacaa gtgatgagga acagaagatg ttgcagtttc tgattgatca caaggattct    5400
gaaattttga aggcgtttgt ttcagagcgc tctattatgc tgcatgaaga gtacatgaaa    5460
tgggagtctt atatgaccag aagggccaag tatcatcgct tggcggcaga ttttgctatg    5520
ttcttgtcta ttcttacatc attgattgtt attttttgct tggtgtattc tatgtatcag    5580
cttttcaaaa ctccagatga gcattcggct tatgacccag caaccaaacc aaagcccaag    5640
acacaggaaa ttaagacact aaagattcgc acagaaacag gcgtgcctgc cacagacctg    5700
cagcagtccg tgatgaaaaa tgttcagcca attgagttgt actgtgaggg taatctggtt    5760
actgactgct cagcactggg tgtttatgac aactcctact tggtaccttt acatttgttt    5820
gagtttgatt ttgacaccat tgtgctgggc gggcgccagt atagcaaggc agactgtgag    5880
aaggttgagt ttgagctcag cgtcggaggg gacatggtgt cgtctgatgc ctgtctgctt    5940
cgactccctt cgggtcccaa agttagaaac atacttcatt tgtttaccaa tgaaattgag    6000
ctcaaaaaga tgacccaaat tacaggaatt atgaattctc cacaccaagc acgtactgtg    6060
tttttttggca gttttttgac agttaagaaa tccattctta catctgatgg gactgtaatg    6120
cctaatgttt tgtcctatgc ggcccagacc tcacggggtt actgtggagc tgcaattgtg    6180
gccgggtctc cggctcgcat tataggcata cattccgctg gaactggctc agttgctttt    6240
tgttctctgg tgtccagaga cgcttttgga cggaccctgc tcagaaaaca aggaaatgtg    6300
gtccgtttgg atgatgatgt aagagtgtct gttccgcgcc gtaccaaatt ggttaaatca    6360
ttggcctacc ccattttcaa acccgatttt gggccagcac ctctgtccca gtttgacaaa    6420
agattggcag acggcgtgaa acttgatgaa gttgtgtttg ctaagcacac aggagacaag    6480
gagatctctg cacctgacca aaagtggctg ctccgcgcag ctcatgttta tgcccagaaa    6540
gtcttctccc gcattgggtt tgataaccag gcattgaccg aggaggaggc catttgcggc    6600
attcctggac ttgacaaaat ggaacaagac actgctccgg gcttacccta tgcacagcag    6660
aacaagagaa gaaaagacat ttgtgacttt gagaaaggcc agttaaaggg ggctgctaag    6720
ctccagaaag agcggtttct taaaggagac tactccgatt tggtctatca atcatttcta    6780
aaggatgaaa ttcggccact tgaaaaagtt agggctggca agaccggct gatcgatgtg    6840
cccccgatgc cccatgtggt tgtcgggcgg caactcctcg gccggtttgt ctccaaattc    6900
cacgaagcaa atggatttga gattggttct gcaataggat gtgaccctga tgtggattgg    6960
actcggtttg gccttgagct cgagcggtat aggtatgttt atgcctgtga ctattctcgg    7020
tttgatgcca accacgctgc tgatgctatg agagttgttc tcaactattt cttctctgag    7080
```

-continued

```
gaccacgggt tcgaccctgg tgtacccgcc ttcatcgagt ctcttattga ctcggtgcat   7140
gcttatgaag agaagagata taatatttat ggaggtttac cctctgggtg ttcttgcacc   7200
tcaattttga atactgtttt gaataatgtt tacattcttg cagcaatgat gaaggctttt   7260
gaaaattttg agcctgatga tattttggtt ttatgctatg gggatgattg cctcatagcc   7320
tctgatttgg aaattgattt tcagaaactt gtccctgtct ttgcagattt tgggcaagtt   7380
attactactg ctgacaagac tgactttttt aaacttacca cgctttctga ggttactttt   7440
ttgaagcgtg cttttgttcc tgacggggcg ctttacaagc cagttatgga tgtgaagacc   7500
ctggaagcaa tcctcagttt cgttcgccct ggtacacagg ctgagaagct cctctctgtt   7560
gcgcagttgg ccggccactg cgaaccggat gagtatgagc acctgtttca gccgtttgag   7620
gggatgtatt acgtccctac ttggcgtgac ttgcgcctcc agtggttgat gaagcttgga   7680
tgctaaactt ttttttggtt ttgttttttct ttgttttttct tttaatctgt agagttaaga   7740
tttttagatt aagagttttt tggaattaga taagagttta gtgagtagtt ttgagcaaaa   7800
aaaaaaaaaa aaaaaaaaaa aaaaaaaaaa aaaaaaaa                           7839
```

<210> SEQ ID NO 3
<211> LENGTH: 2248
<212> TYPE: PRT
<213> ORGANISM: Equine rhinitis A virus

<400> SEQUENCE: 3

```
Met Met Ala Ala Ser Lys Val Tyr Arg Val Cys Glu Gln Thr Leu Leu
1               5                   10                  15

Ala Gly Ala Val Arg Met Met Asp Lys Phe Leu Gln Lys Arg Val Val
            20                  25                  30

Phe Val Pro His Leu Asp Lys Gln Val Arg Leu Thr Gly Leu His Asn
        35                  40                  45

Tyr Asp Asn Thr Cys Trp Leu Asn Ala Leu Thr Gln Leu Thr Gln Ile
    50                  55                  60

Leu Gly Ile Arg Leu Phe Asp Glu His Phe Gly Asn Arg Gly Leu Phe
65                  70                  75                  80

Thr Arg Lys Thr Ile Asp Trp Val Ser Asp Gln Thr Gly Ile Lys Asp
                85                  90                  95

Leu Lys Ser Gly Ala Pro Pro Leu Val Val Tyr Lys Leu Trp Gln
            100                 105                 110

His Gly His Leu Asp Val Gly Thr Met Glu Lys Pro Arg Pro Ile Thr
        115                 120                 125

Leu Trp Ser Gly Pro Lys Val Cys Leu Ser Asp Met Trp Ala Cys Val
    130                 135                 140

Ser Ala Lys Pro Gly His Ala Val Phe Tyr Leu Leu Thr Asp Glu Gly
145                 150                 155                 160

Trp Ile Cys Ile Asp Asp Lys Lys Ile Tyr Tyr Glu Thr Pro Glu Pro
                165                 170                 175

Asp Asp Val Leu Val Phe Ala Pro Tyr Asp Phe Glu Ser Leu Gly Lys
            180                 185                 190

Asp Pro Pro Arg Leu His Gln Arg Tyr Glu Lys Ala Phe Lys Lys Leu
        195                 200                 205

Ser Gly Ala Gly Thr Ser Thr Pro Thr Thr Gly Asn Gln Asn Met Ser
    210                 215                 220

Gly Asn Ser Gly Ser Ile Val Gln Asn Phe Tyr Met Gln Gln Tyr Gln
225                 230                 235                 240
```

-continued

```
Asn Ser Ile Asp Ala Asp Leu Gly Asp Asn Val Ile Ser Pro Glu Gly
                245                 250                 255
Gln Gly Ser Asn Thr Ser Ser Thr Ser Ser Ser Gln Ser Ser Ser Gly
            260                 265                 270
Leu Gly Gly Trp Phe Ser Ser Leu Leu Asn Leu Gly Thr Lys Leu Leu
        275                 280                 285
Ala Asp Lys Lys Thr Glu Glu Thr Thr Asn Ile Glu Asp Arg Ile Glu
    290                 295                 300
Thr Thr Val Val Gly Val Thr Ile Ile Asn Ser Gln Gly Ser Val Gly
305                 310                 315                 320
Thr Thr Tyr Cys Tyr Ser Lys Pro Asp Ser Lys Ala Pro Ser Thr Val
                325                 330                 335
Ser Asp Pro Val Thr Arg Leu Gly Pro Thr Leu Ser Arg His Tyr Thr
            340                 345                 350
Phe Lys Val Gly Glu Trp Pro His Ser Gln Ser His Gly His Ala Trp
        355                 360                 365
Ile Cys Pro Leu Pro Gly Asp Lys Leu Lys Lys Met Gly Ser Phe His
    370                 375                 380
Glu Val Val Lys Ala His His Leu Val Lys Asn Gly Trp Asp Val Val
385                 390                 395                 400
Val Gln Val Asn Ala Ser Phe Ala His Ser Gly Ala Leu Cys Val Ala
                405                 410                 415
Ala Val Pro Glu Tyr Glu His Thr His Glu Lys Ala Leu Lys Trp Ser
            420                 425                 430
Glu Leu Glu Glu Pro Ala Tyr Thr Tyr Gln Gln Leu Ser Val Phe Pro
        435                 440                 445
His Gln Leu Leu Asn Leu Arg Thr Asn Ser Ser Val His Leu Val Met
    450                 455                 460
Pro Tyr Ile Gly Pro Gly Pro Thr Thr Asn Leu Thr Leu His Asn Pro
465                 470                 475                 480
Trp Thr Ile Val Ile Leu Ile Leu Ser Glu Leu Thr Gly Pro Gly Gln
                485                 490                 495
Thr Val Pro Val Thr Met Ser Val Ala Pro Ile Asp Ala Met Val Asn
            500                 505                 510
Gly Pro Leu Pro Asn Pro Glu Ala Pro Ile Arg Val Val Ser Val Pro
        515                 520                 525
Glu Ser Asp Ser Phe Met Ser Ser Val Pro Asn Ser Thr Pro Leu
    530                 535                 540
Tyr Pro Lys Val Val Val Pro Pro Arg Gln Val Pro Gly Arg Phe Thr
545                 550                 555                 560
Asn Phe Ile Asp Val Ala Lys Gln Thr Tyr Ser Phe Cys Ser Ile Ser
                565                 570                 575
Gly Lys Pro Tyr Phe Glu Val Thr Asn Thr Ser Gly Asp Glu Pro Leu
            580                 585                 590
Phe Gln Met Asp Val Ser Leu Ser Ala Ala Glu Leu His Gly Thr Tyr
        595                 600                 605
Val Ala Ser Leu Ser Ser Phe Phe Ala Gln Tyr Arg Gly Ser Leu Asn
    610                 615                 620
Phe Asn Phe Ile Phe Thr Gly Ala Ala Thr Lys Ala Lys Phe Leu
625                 630                 635                 640
Val Ala Phe Val Pro Pro His Thr Ala Ala Pro Lys Thr Arg Asp Glu
                645                 650                 655
```

Ala Met Ala Cys Ile His Ala Val Trp Asp Val Gly Leu Asn Ser Ala
            660                 665                 670

Phe Ser Phe Asn Val Pro Tyr Ser Ser Pro Ala Asp Phe Met Ala Val
    675                 680                 685

Tyr Ser Ala Glu Ala Thr Val Val Asn Val Ser Gly Trp Leu Gln Val
    690                 695                 700

Tyr Ala Leu Thr Ala Leu Thr Ser Thr Asp Ile Ala Val Asn Ser Lys
705                 710                 715                 720

Gly Arg Val Leu Val Ala Val Ser Ala Gly Pro Asp Phe Ser Leu Arg
                725                 730                 735

His Pro Val Asp Leu Pro Asp Lys Gln Val Thr Asn Val Gly Glu Asp
            740                 745                 750

Gly Glu Pro Gly Glu Thr Glu Pro Arg Tyr Ala Leu Ser Pro Val Asp
        755                 760                 765

Met His Val His Thr Asp Val Ser Phe Leu Leu Asp Arg Phe Phe Asp
    770                 775                 780

Val Glu Thr Ile Glu Leu Ser Asn Leu Thr Gly Ser Pro Thr Thr His
785                 790                 795                 800

Ile Leu Asn Pro Phe Gly Ser Thr Ala Gln Leu Ala Trp Ala Arg Leu
                805                 810                 815

Leu Asn Thr Cys Thr Tyr Phe Phe Ser Asn Leu Glu Leu Ser Ile Gln
            820                 825                 830

Phe Lys Phe Thr Thr Met Pro Ser Ser Val Glu Lys Gly Phe Val Trp
        835                 840                 845

Val Lys Trp Phe Pro Val Gly Ala Pro Thr Lys Thr Thr Asp Ala Trp
850                 855                 860

Gln Leu Glu Gly Gly Gly Asn Ser Val Arg Ile Gln Lys Leu Ala Val
865                 870                 875                 880

Ala Gly Leu Ser Pro Thr Val Ile Phe Lys Ile Ala Gly Ser Arg Ser
                885                 890                 895

Gln Ala Cys Gly Phe Asn Val Pro Tyr Thr Ser Met Trp Arg Val Val
            900                 905                 910

Pro Val Phe Tyr Asn Gly Trp Gly Ala Pro Thr Lys Glu Lys Ala Thr
        915                 920                 925

Tyr Asn Trp Leu Pro Gly Ala His Phe Gly Ser Ile Leu Leu Thr Ser
    930                 935                 940

Asp Ala His Asp Lys Gly Gly Cys Tyr Leu Arg Tyr Arg Phe Pro Arg
945                 950                 955                 960

Ala Ser Met Tyr Cys Pro Arg Pro Ile Pro Pro Ala Phe Thr Arg Pro
                965                 970                 975

Ala Asp Lys Thr Arg His Lys Phe Pro Thr Asn Ile Asn Lys Gln Cys
            980                 985                 990

Thr Asn Tyr Ala Leu Leu Lys Leu Ala Gly Asp Val Glu Ser Asn Pro
        995                 1000                1005

Gly Pro Thr Ile Phe Ser Lys Ala Ser Ala Asp Leu Asn Ala Leu
    1010                1015                1020

Ser Thr Ser Leu Gly Glu Leu Thr Gly Met Leu Lys Asp Leu Lys
    1025                1030                1035

Ala Lys Ala Glu Thr Tyr Ser Pro Phe Tyr Lys Met Ala Lys Met
    1040                1045                1050

Leu Phe Lys Leu Ala Thr Leu Ala Val Ala Ala Met Arg Thr Lys
    1055                1060                1065

Asp Pro Val Val Val Val Met Leu Ile Ala Asp Phe Gly Leu Glu

```
            1070                1075                1080
Val Phe Asp Thr Gly Phe Phe Phe Ser Tyr Phe Gln Glu Lys Leu
        1085                1090                1095

Gln Pro Tyr Met Lys Thr Ile Pro Gly Lys Val Ser Asp Leu Val
        1100                1105                1110

Thr Asp Ala Ala Thr Ala Ala Ala Gln Ile Pro Lys Gly Val Tyr
        1115                1120                1125

Ser Phe Val Ser Ser Phe Phe Glu Thr Pro Glu Gly Val Val Glu
        1130                1135                1140

Lys Gln Val Ser Leu Arg Thr Ile Asn Asp Ile Phe Thr Leu Leu
        1145                1150                1155

Lys Asn Ser Asp Trp Phe Ile Lys Thr Leu Val Ala Leu Lys Lys
        1160                1165                1170

Trp Leu Val Ser Trp Phe Lys Gln Glu Gln Ala Asp Asp Ala
        1175                1180                1185

Leu Tyr Ser Glu Leu Glu Lys Tyr Pro Leu Tyr Lys Leu Lys Leu
        1190                1195                1200

Lys Glu Pro Asp Thr Gln Glu Glu Ala Arg Gln Trp Phe Lys Asp
        1205                1210                1215

Met Gln Gln Arg Ala Leu Ala Val Lys Asp Lys Gly Leu Phe Ser
        1220                1225                1230

Leu Leu Gln Ile Pro Leu Val Asn Leu Pro Thr Ser Arg Pro Glu
        1235                1240                1245

Pro Val Val Cys Val Leu Arg Gly Ala Ser Gly Gln Gly Lys Ser
        1250                1255                1260

Tyr Leu Ala Asn Met Met Ala Gln Ala Ile Ser Leu Leu Leu Thr
        1265                1270                1275

Gly Lys Gln Asn Ser Val Trp Ser Cys Pro Pro Asp Pro Thr Tyr
        1280                1285                1290

Phe Asp Gly Tyr Asn Gly Gln Ala Val Val Ile Met Asp Asp Leu
        1295                1300                1305

Gly Gln Asn Pro Asn Gly Ala Asp Phe Lys Tyr Phe Cys Gln Met
        1310                1315                1320

Val Ser Thr Thr Ala Phe Val Pro Pro Met Ala His Leu Asp Asp
        1325                1330                1335

Lys Gly Ile Pro Phe Thr Ser Pro Val Val Ile Cys Thr Thr Asn
        1340                1345                1350

Leu His Ser Ser Phe Thr Pro Ile Thr Val Ser Cys Pro Glu Ala
        1355                1360                1365

Leu Lys Arg Arg Phe Arg Phe Asp Val Thr Val Ser Ala Lys Pro
        1370                1375                1380

Gly Phe Val Arg Thr Val Gly Ser Ser Gln Leu Leu Asn Leu Pro
        1385                1390                1395

Leu Ala Leu Lys Pro Ala Gly Leu Pro Pro His Pro Ile Phe Glu
        1400                1405                1410

Asn Asp Met Pro Ile Leu Asn Gly Gln Ala Val Lys Leu Ala Leu
        1415                1420                1425

Ser Gly Val Glu Val Thr Ala Phe Glu Leu Ile Glu Met Ile Leu
        1430                1435                1440

Ser Glu Val Gln Asn Arg Gln Asp Thr His Lys Met Pro Ile Phe
        1445                1450                1455

Lys Gln Ser Trp Ser Asp Leu Phe Lys Lys Cys Thr Ser Asp Glu
        1460                1465                1470
```

```
Glu Gln Lys Met Leu Gln Phe Leu Ile Asp His Lys Asp Ser Glu
    1475                1480                1485

Ile Leu Lys Ala Phe Val Ser Glu Arg Ser Ile Met Leu His Glu
    1490                1495                1500

Glu Tyr Met Lys Trp Glu Ser Tyr Met Thr Arg Arg Ala Lys Tyr
    1505                1510                1515

His Arg Leu Ala Ala Asp Phe Ala Met Phe Leu Ser Ile Leu Thr
    1520                1525                1530

Ser Leu Ile Val Ile Phe Cys Leu Val Tyr Ser Met Tyr Gln Leu
    1535                1540                1545

Phe Lys Thr Pro Asp Glu His Ser Ala Tyr Asp Pro Ala Thr Lys
    1550                1555                1560

Pro Lys Pro Lys Thr Gln Glu Ile Lys Thr Leu Lys Ile Arg Thr
    1565                1570                1575

Glu Thr Gly Val Pro Ala Thr Asp Leu Gln Gln Ser Val Met Lys
    1580                1585                1590

Asn Val Gln Pro Ile Glu Leu Tyr Cys Glu Gly Asn Leu Val Thr
    1595                1600                1605

Asp Cys Ser Ala Leu Gly Val Tyr Asp Asn Ser Tyr Leu Val Pro
    1610                1615                1620

Leu His Leu Phe Glu Phe Asp Phe Asp Thr Ile Val Leu Gly Gly
    1625                1630                1635

Arg Gln Tyr Ser Lys Ala Asp Cys Glu Lys Val Glu Phe Glu Leu
    1640                1645                1650

Ser Val Gly Gly Asp Met Val Ser Ser Asp Ala Cys Leu Leu Arg
    1655                1660                1665

Leu Pro Ser Gly Pro Lys Val Arg Asn Ile Leu His Leu Phe Thr
    1670                1675                1680

Asn Glu Ile Glu Leu Lys Lys Met Thr Gln Ile Thr Gly Ile Met
    1685                1690                1695

Asn Ser Pro His Gln Ala Arg Thr Val Phe Phe Gly Ser Phe Leu
    1700                1705                1710

Thr Val Lys Lys Ser Ile Leu Thr Ser Asp Gly Thr Val Met Pro
    1715                1720                1725

Asn Val Leu Ser Tyr Ala Ala Gln Thr Ser Arg Gly Tyr Cys Gly
    1730                1735                1740

Ala Ala Ile Val Ala Gly Ser Pro Ala Arg Ile Ile Gly Ile His
    1745                1750                1755

Ser Ala Gly Thr Gly Ser Val Ala Phe Cys Ser Leu Val Ser Arg
    1760                1765                1770

Asp Ala Leu Glu Arg Thr Leu Pro Gln Lys Gln Gly Asn Val Val
    1775                1780                1785

Arg Leu Asp Asp Asp Val Arg Val Ser Val Pro Arg Arg Thr Lys
    1790                1795                1800

Leu Val Lys Ser Leu Ala Tyr Pro Ile Phe Lys Pro Asp Phe Gly
    1805                1810                1815

Pro Ala Pro Leu Ser Gln Phe Asp Lys Arg Leu Ala Asp Gly Val
    1820                1825                1830

Lys Leu Asp Glu Val Val Phe Ala Lys His Thr Gly Asp Lys Glu
    1835                1840                1845

Ile Ser Ala Pro Asp Gln Lys Trp Leu Leu Arg Ala Ala His Val
    1850                1855                1860
```

-continued

```
Tyr Ala Gln Lys Val Phe Ser Arg Ile Gly Phe Asp Asn Gln Ala
    1865                1870                1875

Leu Thr Glu Glu Ala Ile Cys Gly Ile Pro Gly Leu Asp Lys
    1880                1885                1890

Met Glu Gln Asp Thr Ala Pro Gly Leu Pro Tyr Ala Gln Gln Asn
    1895                1900                1905

Lys Arg Arg Lys Asp Ile Cys Asp Phe Glu Lys Gly Gln Leu Lys
    1910                1915                1920

Gly Ala Ala Lys Leu Gln Lys Glu Arg Phe Leu Lys Gly Asp Tyr
    1925                1930                1935

Ser Asp Leu Val Tyr Gln Ser Phe Leu Lys Asp Glu Ile Arg Pro
    1940                1945                1950

Leu Glu Lys Val Arg Ala Gly Lys Thr Arg Leu Ile Asp Val Pro
    1955                1960                1965

Pro Met Pro His Val Val Gly Arg Gln Leu Leu Gly Arg Phe
    1970            1975                1980

Val Ser Lys Phe His Glu Ala Asn Gly Phe Glu Ile Gly Ser Ala
    1985                1990                1995

Ile Gly Cys Asp Pro Asp Val Asp Trp Thr Arg Phe Gly Leu Glu
    2000                2005                2010

Leu Glu Arg Tyr Arg Tyr Val Tyr Ala Cys Asp Tyr Ser Arg Phe
    2015                2020                2025

Asp Ala Asn His Ala Ala Asp Ala Met Arg Val Val Leu Asn Tyr
    2030                2035                2040

Phe Phe Ser Glu Asp His Gly Phe Asp Pro Gly Val Pro Ala Phe
    2045                2050                2055

Ile Glu Ser Leu Ile Asp Ser Val His Ala Tyr Glu Glu Lys Arg
    2060                2065                2070

Tyr Asn Ile Tyr Gly Gly Leu Pro Ser Gly Cys Ser Cys Thr Ser
    2075                2080                2085

Ile Leu Asn Thr Val Leu Asn Asn Val Tyr Ile Leu Ala Ala Met
    2090                2095                2100

Met Lys Ala Phe Glu Asn Phe Glu Pro Asp Asp Ile Leu Val Leu
    2105                2110                2115

Cys Tyr Gly Asp Asp Cys Leu Ile Ala Ser Asp Leu Glu Ile Asp
    2120                2125                2130

Phe Gln Lys Leu Val Pro Val Phe Ala Asp Phe Gly Gln Val Ile
    2135                2140                2145

Thr Thr Ala Asp Lys Thr Asp Phe Phe Lys Leu Thr Thr Leu Ser
    2150                2155                2160

Glu Val Thr Phe Leu Lys Arg Ala Phe Val Pro Asp Gly Ala Leu
    2165                2170                2175

Tyr Lys Pro Val Met Asp Val Lys Thr Leu Glu Ala Ile Leu Ser
    2180                2185                2190

Phe Val Arg Pro Gly Thr Gln Ala Glu Lys Leu Leu Ser Val Ala
    2195                2200                2205

Gln Leu Ala Gly His Cys Glu Pro Asp Glu Tyr Glu His Leu Phe
    2210                2215                2220

Gln Pro Phe Glu Gly Met Tyr Tyr Val Pro Thr Trp Arg Asp Leu
    2225                2230                2235

Arg Leu Gln Trp Leu Met Lys Leu Gly Cys
    2240                2245
```

```
<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgaatagcaa gggccgtgtt                                                   20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
accgttgtaa aagactggca ca                                                22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtcagtaaaa cgcaacaacc at                                                22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgtgaagaat gtcctgaagg ca                                                22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
accatccacc taaaccagac ga                                                22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
attggctttg tcaggtgttg aa                                                22

<210> SEQ ID NO 10
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtttctaact ttgggacccg aa                                            22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tggatttgag attggttctg ca                                            22

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcgaacgaaa ctgaggattg                                               20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ctgtagcgtc agtaaaacgc                                               20

<210> SEQ ID NO 14
<211> LENGTH: 340
<212> TYPE: DNA
<213> ORGANISM: Equine rhinitis A virus

<400> SEQUENCE: 14
acttttagga gatgaccaaa cgcagtaacc gcaagcaatt gcctgtagcg tcagtaaaac    60
gcaatacaca agatttgagc ctgtagcgtc agtaaaacgc tgcaaccaca agctattgac   120
tgtagcgtca gtaaaacgca acattcttg tggcgctcgc gtagcgctca agtgcagagc    180
ttcccggctt taagggttac tgctcgtaat gagagcacat gacattttgc caagatttcc   240
tggcaattgt cacgggagag aggagcccgt tctcgggcac ttttctctca aacaatgttg   300
gcgcgcctcg gcgcgccccc ccttttttcag ccccctgtca                        340
```